US012268587B2

(12) United States Patent
Morrison et al.

(10) Patent No.: US 12,268,587 B2
(45) Date of Patent: Apr. 8, 2025

(54) INTRA VASCULAR GUIDEWIRE FILTER SYSTEM FOR PULMONARY EMBOLISM PROTECTION AND EMBOLISM REMOVAL OR MACERATION

(71) Applicant: Surmodics MD, LLC, Eden Prairie, MN (US)

(72) Inventors: Samuel Morrison, Eden Prairie, MN (US); Chad Stark, Eden Prairie, MN (US)

(73) Assignee: Surmodics MD, LLC, Eden Prairie, MN (US)

( * ) Notice: Subject to any disclaimer, the term of this patent is extended or adjusted under 35 U.S.C. 154(b) by 806 days.

(21) Appl. No.: 16/742,662

(22) Filed: Jan. 14, 2020

(65) Prior Publication Data

US 2020/0155293 A1    May 21, 2020

Related U.S. Application Data

(63) Continuation-in-part of application No. 15/093,916, filed on Apr. 8, 2016, now Pat. No. 10,806,559,
(Continued)

(51) Int. Cl.
*A61F 2/01* (2006.01)
*A61B 17/22* (2006.01)
(Continued)

(52) U.S. Cl.
CPC ........ *A61F 2/013* (2013.01); *A61B 17/22012* (2013.01); *A61B 17/22032* (2013.01);
(Continued)

(58) Field of Classification Search
CPC .......... A61F 2/013; A61F 2/012; A61F 2/011; A61F 2002/016; A61F 2210/0014;
(Continued)

(56) References Cited

U.S. PATENT DOCUMENTS 4,425,908 A    1/1984  Simon
4,611,594 A    9/1986  Grayhack et al.
(Continued)

FOREIGN PATENT DOCUMENTS

DE    2211972 A1    9/1972
EP    0655228 A1    5/1995
(Continued)

OTHER PUBLICATIONS

"Alligator Retrieval Device (ARD), Instructions for Use", Chestnut Medical Technologies, Inc., (Accessed 2010), 1 pg.
(Continued)

*Primary Examiner* — Ashley L Fishback
*Assistant Examiner* — Chima U Igboko
(74) *Attorney, Agent, or Firm* — Schwegman Lundberg & Woessner, P.A.

(57) ABSTRACT

An intravascular emboli capture and retrieval system for intravascular embolism protection and embolism removal or maceration. Guidewire mounted proximally and distally located multiple opening filters are deployed within the vasculature and used to part, divide and macerate embolic debris and to capture such embolic debris within the confines thereof. A deployable flexible preformed memory shaped capture sleeve is alternatively used to collapse one or more filters and embolic debris therein for subsequent proximal withdrawal from the vasculature.

19 Claims, 58 Drawing Sheets

Related U.S. Application Data which is a continuation of application No. 12/738,702, filed as application No. PCT/US2008/081310 on Oct. 27, 2008, now Pat. No. 9,827,084.

(60) Provisional application No. 61/000,465, filed on Oct. 26, 2007.

(51) Int. Cl.
*A61B 17/221* (2006.01)
*A61B 17/00* (2006.01)

(52) U.S. Cl.
CPC ............ *A61B 17/221* (2013.01); *A61F 2/012* (2020.05); *A61B 2017/00778* (2013.01); *A61B 2017/00867* (2013.01); *A61B 2017/22001* (2013.01); *A61B 2017/22035* (2013.01); *A61B 2017/22038* (2013.01); *A61B 2017/22042* (2013.01); *A61B 2017/22054* (2013.01); *A61B 2017/2212* (2013.01); *A61F 2/011* (2020.05); *A61F 2002/016* (2013.01); *A61F 2210/0014* (2013.01); *A61F 2210/0057* (2013.01); *A61F 2210/0061* (2013.01); *A61F 2230/0008* (2013.01); *A61F 2230/0069* (2013.01); *A61F 2230/008* (2013.01); *A61F 2230/0086* (2013.01); *A61F 2230/0093* (2013.01); *A61F 2230/0097* (2013.01); *A61F 2250/0036* (2013.01); *A61F 2250/004* (2013.01); *A61F 2250/0042* (2013.01)

(58) Field of Classification Search
CPC ...... A61F 2210/0057; A61F 2210/0061; A61F 2230/0008; A61F 2230/0069; A61F 2230/008; A61F 2230/0086; A61F 2230/0093; A61F 2230/0097; A61F 2250/0036; A61F 2250/004; A61F 2250/0042; A61F 2/0108; A61F 2002/018; A61B 17/22012; A61B 17/22032; A61B 17/221; A61B 2017/00778; A61B 2017/00867; A61B 2017/22001; A61B 2017/22035; A61B 2017/22038; A61B 2017/22042; A61B 2017/22054; A61B 2017/2212; A61B 2090/3966

See application file for complete search history.

(56) References Cited

U.S. PATENT DOCUMENTS

| | | |
|---|---|---|
| 4,643,184 A | 2/1987 | Mobin-Uddin |
| 4,690,672 A | 9/1987 | Veltrup |
| 4,832,055 A * | 5/1989 | Palestrant ............. A61F 2/0105 128/899 |
| 5,011,488 A | 4/1991 | Ginsburg |
| 5,074,871 A | 12/1991 | Groshong |
| 5,102,415 A | 4/1992 | Guenther et al. |
| 5,370,609 A | 12/1994 | Drasler et al. |
| 5,419,774 A | 5/1995 | Willard et al. |
| 5,688,234 A | 11/1997 | Frisbie |
| 5,785,675 A | 7/1998 | Drasler et al. |
| 5,814,064 A | 9/1998 | Daniel et al. |
| 5,908,435 A | 6/1999 | Samuels |
| 5,941,871 A | 8/1999 | Adams et al. |
| 5,968,057 A | 10/1999 | Taheri |
| 5,971,938 A | 10/1999 | Hart et al. |
| 5,989,271 A | 11/1999 | Bonnette et al. |
| 6,001,118 A | 12/1999 | Daniel et al. |
| 6,059,814 A | 5/2000 | Ladd |
| 6,066,149 A | 5/2000 | Samson et al. |
| 6,080,170 A | 6/2000 | Nash et al. |
| 6,096,001 A | 8/2000 | Drasler et al. |
| 6,135,977 A | 10/2000 | Drasler et al. |
| 6,171,327 B1 | 1/2001 | Daniel et al. |
| 6,176,844 B1 | 1/2001 | Lee |
| 6,203,561 B1 | 3/2001 | Ramee et al. |
| 6,206,868 B1 | 3/2001 | Parodi |
| 6,221,006 B1 | 4/2001 | Dubrul et al. |
| 6,238,412 B1 | 5/2001 | Dubrul et al. |
| 6,245,089 B1 | 6/2001 | Daniel et al. |
| 6,258,061 B1 | 7/2001 | Drasler et al. |
| 6,258,115 B1 | 7/2001 | Dubrul |
| 6,277,139 B1 | 8/2001 | Levinson et al. |
| 6,290,710 B1 | 9/2001 | Cryer et al. |
| 6,325,815 B1 | 12/2001 | Kusleika et al. |
| 6,325,816 B1 | 12/2001 | Fulton et al. |
| 6,338,735 B1 | 1/2002 | Stevens |
| 6,346,116 B1 | 2/2002 | Brooks et al. |
| 6,361,546 B1 | 3/2002 | Khosravi |
| 6,371,969 B1 | 4/2002 | Tsugita et al. |
| 6,436,120 B1 | 8/2002 | Meglin |
| 6,443,972 B1 | 9/2002 | Bosma et al. |
| 6,447,531 B1 | 9/2002 | Amplatz |
| 6,450,989 B2 | 9/2002 | Dubrul et al. |
| 6,458,139 B1 * | 10/2002 | Palmer ................. A61B 17/221 606/113 |
| 6,485,500 B1 | 11/2002 | Kokish et al. |
| 6,485,502 B2 | 11/2002 | Green |
| 6,491,660 B2 | 12/2002 | Guo et al. |
| 6,511,492 B1 | 1/2003 | Rosenbluth et al. |
| 6,517,551 B1 | 2/2003 | Driskill |
| 6,524,323 B1 | 2/2003 | Nash et al. |
| 6,527,746 B1 | 3/2003 | Oslund et al. |
| 6,544,209 B1 | 4/2003 | Drasler et al. |
| 6,575,996 B1 | 6/2003 | Denison et al. |
| 6,605,102 B1 | 8/2003 | Mazzocchi et al. |
| 6,635,070 B2 | 10/2003 | Leeflang et al. |
| 6,652,548 B2 | 11/2003 | Evans et al. |
| 6,676,637 B1 | 1/2004 | Bonnette et al. |
| 6,679,893 B1 | 1/2004 | Tran |
| 6,682,546 B2 | 1/2004 | Amplatz |
| 6,695,813 B1 | 2/2004 | Boyle et al. |
| 6,695,858 B1 | 2/2004 | Dubrul et al. |
| 6,712,835 B2 | 3/2004 | Mazzocchi et al. |
| 6,726,701 B2 | 4/2004 | Gilson et al. |
| 6,740,061 B1 | 5/2004 | Oslund et al. |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,805,864 B1 | 10/2004 | Vinson et al. |
| 6,814,740 B2 | 11/2004 | Mcalister |
| 6,887,256 B2 | 5/2005 | Gilson et al. |
| 6,989,019 B2 | 1/2006 | Mazzocchi et al. |
| 7,011,654 B2 | 3/2006 | Dubrul et al. |
| 7,163,550 B2 | 1/2007 | Boismier |
| 7,169,154 B1 | 1/2007 | Que et al. |
| 7,220,269 B1 | 5/2007 | Ansel et al. |
| 7,241,304 B2 | 7/2007 | Boyle et al. |
| 7,241,305 B2 | 7/2007 | Ladd |
| 7,252,675 B2 | 8/2007 | Denison et al. |
| 7,344,549 B2 | 3/2008 | Boyle et al. |
| 7,491,210 B2 | 2/2009 | Dubrul et al. |
| 7,537,601 B2 | 5/2009 | Cano et al. |
| 7,717,936 B2 | 5/2010 | Keating et al. |
| 7,766,936 B2 | 8/2010 | Ladd |
| 7,780,694 B2 | 8/2010 | Palmer et al. |
| 7,785,345 B2 | 8/2010 | Ladd |
| 9,149,609 B2 | 10/2015 | Ansel et al. |
| 9,387,313 B2 | 7/2016 | Culbert et al. |
| 9,700,332 B2 | 7/2017 | Marchand et al. |
| 9,827,084 B2 | 11/2017 | Bonnette et al. |
| 9,943,397 B2 | 4/2018 | Bonnette et al. |
| 10,512,478 B2 | 12/2019 | Greenhalgh et al. |
| 10,806,559 B2 | 10/2020 | Bonnette et al. |
| 2001/0012951 A1 | 8/2001 | Bates et al. |
| 2001/0041908 A1 | 11/2001 | Levinson et al. |
| 2002/0022859 A1 * | 2/2002 | Hogendijk ............. A61B 17/22 606/200 |
| 2002/0026203 A1 | 2/2002 | Bates et al. |
| 2002/0026211 A1 | 2/2002 | Khosravi et al. |

(56) References Cited

U.S. PATENT DOCUMENTS

| | | |
|---|---|---|
| 2002/0068954 A1 | 6/2002 | Foster |
| 2002/0095172 A1 | 7/2002 | Mazzocchi et al. |
| 2002/0123765 A1 | 9/2002 | Sepetka et al. |
| 2003/0065355 A1* | 4/2003 | Weber .................. A61L 29/126 606/200 |
| 2003/0083693 A1 | 5/2003 | Daniel et al. |
| 2003/0114879 A1 | 6/2003 | Euteneuer et al. |
| 2003/0144686 A1 | 7/2003 | Martinez et al. |
| 2003/0187475 A1 | 10/2003 | Tsugita et al. |
| 2003/0187495 A1 | 10/2003 | Cully et al. |
| 2003/0229374 A1 | 12/2003 | Brady et al. |
| 2004/0133232 A1 | 7/2004 | Rosenbluth et al. |
| 2004/0153117 A1 | 8/2004 | Clubb et al. |
| 2004/0153118 A1 | 8/2004 | Clubb et al. |
| 2004/0215230 A1 | 10/2004 | Frazier et al. |
| 2005/0119668 A1 | 6/2005 | Teague et al. |
| 2005/0159772 A1 | 7/2005 | Lowe et al. |
| 2005/0192620 A1 | 9/2005 | Cully et al. |
| 2006/0030877 A1 | 2/2006 | Martinez et al. |
| 2006/0135987 A1 | 6/2006 | Jones et al. |
| 2006/0241676 A1 | 10/2006 | Johnson et al. |
| 2006/0253145 A1 | 11/2006 | Lucas |
| 2007/0060942 A2 | 3/2007 | Zadno-azizi |
| 2007/0088383 A1 | 4/2007 | Pal et al. |
| 2007/0167974 A1 | 7/2007 | Cully et al. |
| 2007/0191878 A1 | 8/2007 | Segner et al. |
| 2007/0198051 A1 | 8/2007 | Clubb et al. |
| 2007/0208351 A1 | 9/2007 | Turner et al. |
| 2007/0233175 A1 | 10/2007 | Zaver et al. |
| 2008/0234722 A1 | 9/2008 | Bonnette et al. |
| 2008/0269798 A1* | 10/2008 | Ramzipoor .......... A61B 17/221 604/35 |
| 2008/0312681 A1 | 12/2008 | Ansel et al. |
| 2009/0069828 A1 | 3/2009 | Martin et al. |
| 2010/0268264 A1* | 10/2010 | Bonnette ............... A61F 2/0108 606/200 |
| 2011/0282379 A1 | 11/2011 | Lee et al. |
| 2012/0059356 A1* | 3/2012 | di Palma .......... A61B 17/12186 604/509 |
| 2012/0150211 A1* | 6/2012 | Galdonik ......... A61B 17/12109 606/200 |
| 2014/0005712 A1* | 1/2014 | Martin .................. A61B 17/221 606/200 |
| 2014/0276922 A1* | 9/2014 | McLain ............. A61B 17/3207 606/127 |
| 2016/0143721 A1* | 5/2016 | Rosenbluth .... A61B 17/320725 600/200 |
| 2016/0220346 A1 | 8/2016 | Bonnette et al. |
| 2016/0367285 A1 | 12/2016 | Sos |
| 2017/0035445 A1 | 2/2017 | Nguyen et al. |
| 2017/0035455 A1 | 2/2017 | Wilson et al. |
| 2017/0143938 A1 | 5/2017 | Ogle et al. |
| 2017/0224375 A1 | 8/2017 | Robertson et al. |
| 2017/0325931 A1 | 11/2017 | Bonnette et al. |
| 2018/0132873 A1* | 5/2018 | Sirivong ............. A61B 17/221 |
| 2018/0200489 A1 | 7/2018 | Gianotti et al. |
| 2018/0311029 A1* | 11/2018 | Hocking ................. A61F 2/012 |
| 2019/0125513 A1 | 5/2019 | Purcell et al. |
| 2019/0298395 A1 | 10/2019 | Krolik et al. |
| 2020/0390457 A1* | 12/2020 | Nageswaran ......... A61M 25/09 |
| 2021/0137667 A1 | 5/2021 | Bonnette et al. |
| 2023/0063821 A1 | 3/2023 | Ganske et al. |
| 2023/0389909 A1 | 12/2023 | Marine et al. |
| 2024/0285389 A1 | 8/2024 | Bonnette et al. |

FOREIGN PATENT DOCUMENTS

| | | |
|---|---|---|
| EP | 1545388 B1 | 8/2009 |
| EP | 2211972 A1 | 8/2010 |
| EP | 2211972 B1 | 12/2015 |
| FR | 2580504 A1 | 10/1986 |
| FR | 2694687 A1 | 2/1994 |
| GB | 2211972 A | 7/1989 |
| GB | 2211972 B | 10/1991 |
| JP | 8187294 | 7/1996 |
| WO | WO-9922673 A1 | 5/1999 |
| WO | WO-0115629 A1 | 3/2001 |
| WO | WO-0117602 A1 | 3/2001 |
| WO | WO-0145590 A2 | 6/2001 |
| WO | WO-0145592 A1 * | 6/2001 ............ A61F 2/013 |
| WO | WO-0167989 A2 | 9/2001 |
| WO | WO-2008036156 A1 | 3/2008 |
| WO | WO-2008157202 A1 | 12/2008 |
| WO | WO-2009055782 A1 | 4/2009 |
| WO | 2017060901 | 4/2017 |
| WO | WO-2021146404 A1 | 7/2021 |
| WO | WO-2023028308 A2 | 3/2023 |
| WO | WO-2023028308 A3 | 4/2023 |
| WO | 2025038886 | 2/2025 |

OTHER PUBLICATIONS

U.S. Appl. No. 12/152,367, Examiner Interview Summary mailed Nov. 15, 2012, 3 pgs.

"U.S. Appl. No. 12/152,367, Final Office Action mailed Aug. 28, 2014", 10 pgs.

"U.S. Appl. No. 12/152,367, Final Office Action mailed Dec. 6, 2011", 11 pgs.

"U.S. Appl. No. 12/152,367, Final Office Action mailed Dec. 6, 2012", 10 pgs.

"U.S. Appl. No. 12/152,367, Non Final Office Action mailed Mar. 13, 2015", 10 pgs.

"U.S. Appl. No. 12/152,367, Non Final Office Action mailed Apr. 1, 2011", 12 pgs.

"U.S. Appl. No. 12/152,367, Non Final Office Action mailed Jun. 18, 2012", 10 pgs.

"U.S. Appl. No. 12/152,367, Notice of Allowance mailed Jun. 17, 2015", 7 pgs.

"U.S. Appl. No. 12/152,367, Response filed Apr. 24, 2015 to Non Final Office Action mailed Mar. 13, 2015", 16 pgs.

"U.S. Appl. No. 12/152,367, Response filed May 6, 2013 to Final Office Action mailed Dec. 6, 2012", 11 pgs.

"U.S. Appl. No. 12/152,367, Response filed May 7, 2012 to Final Office Action mailed Dec. 6, 2011", 7 pgs.

"U.S. Appl. No. 12/152,367, Response filed Sep. 26, 2011 to Non Final Office Action mailed Apr. 1, 2011", 11 pgs.

"U.S. Appl. No. 12/152,367, Response filed Nov. 19, 2012 to Non Final Office Action mailed Jun. 18, 2012", 12 pgs.

"U.S. Appl. No. 12/152,367, Response filed Nov. 19, 2014 Final Office Action mailed Aug. 28, 2014", 10 pgs.

"U.S. Appl. No. 12/738,702, Examiner Interview Summary mailed Mar. 6, 2015", 3 pgs.

"U.S. Appl. No. 12/738,702, Examiner Interview Summary mailed Mar. 9, 2016", 3 pgs.

"U.S. Appl. No. 12/738,702, Examiner Interview Summary mailed Aug. 9, 2017", 3 pgs.

"U.S. Appl. No. 12/738,702, Final Office Action mailed May 17, 2017", 17 pgs.

"U.S. Appl. No. 12/738,702, Final Office Action mailed Aug. 15, 2013", 12 pgs.

"U.S. Appl. No. 12/738,702, Final Office Action mailed Dec. 19, 2014", 14 pgs.

"U.S. Appl. No. 12/738,702, Non Final Office Action mailed Apr. 23, 2015", (9 pgs).

"U.S. Appl. No. 12/738,702, Non Final Office Action mailed Jul. 7, 2016", 8 pgs.

"U.S. Appl. No. 12/738,702, Non Final Office Action mailed Oct. 3, 2014", 11 pgs.

"U.S. Appl. No. 12/738,702, Non Final Office Action mailed Nov. 6, 2012", 11 pgs.

"U.S. Appl. No. 12/738,702, Non Final Office Action mailed Dec. 1, 2015", 9 pgs.

"U.S. Appl. No. 12/738,702, Notice of Allowance mailed Oct. 18, 2017", 12 pgs.

"U.S. Appl. No. 12/738,702, Response filed Mar. 9, 2016 to Non Final Office Action mailed Dec. 1, 2015", 17 pgs.

(56) References Cited

OTHER PUBLICATIONS

"U.S. Appl. No. 12/738,702, Response filed Mar. 13, 2015 to Final Office Action mailed Dec. 19, 2014", 11 pgs.
"U.S. Appl. No. 12/738,702, Response filed May 6, 2013 to Non Final Office Action mailed Nov. 6, 2012", 9 pgs.
"U.S. Appl. No. 12/738,702, Response filed Jun. 1, 2015 to Non Final Office Action mailed Apr. 23, 2015", 5 pgs.
"U.S. Appl. No. 12/738,702, Response filed Aug. 2, 2017 to Final Office Action mailed May 17, 2017", 12 pgs.
"U.S. Appl. No. 12/738,702, Response filed Aug. 24, 2016 to Non Final Office Action mailed Jul. 7, 2016", (14 pgs).
"U.S. Appl. No. 12/738,702, Response filed Sep. 28, 2012 to Restriction Requirement mailed Jun. 28, 2012", 9 pgs.
"U.S. Appl. No. 12/738,702, Response filed Nov. 11, 2014 to Non Final Office Action mailed Oct. 3, 2014", 10 pgs.
"U.S. Appl. No. 12/738,702, Response filed Nov. 14, 2013 to Final Office Action mailed Aug. 15, 2013", 7 pgs.
"U.S. Appl. No. 12/738,702, Restriction Requirement mailed Jun. 28, 2012", 8 pgs.
"U.S. Appl. No. 15/093,916, Examiner Interview Summary mailed Mar. 5, 2019", 4 pgs.
"U.S. Appl. No. 15/093,916, Final Office Action mailed Oct. 18, 2018", 14 pgs.
"U.S. Appl. No. 15/093,916, Non Final Office Action mailed Mar. 20, 2018", 9 pgs.
"U.S. Appl. No. 15/093,916, Non Final Office Action mailed Jul. 18, 2019", 14 pgs.
"U.S. Appl. No. 15/093,916, Response filed Mar. 18, 2019 to Final Office Action mailed Oct. 18, 2018", 15 pgs.
"U.S. Appl. No. 15/093,916, Response to Non Final Office Action mailed Mar. 20, 2018 filed Jun. 20, 2018", 10 pgs.
"U.S. Appl. No. 15/667,984, Non Final Office Action mailed Oct. 19, 2017", 11 pgs.
"U.S. Appl. No. 15/667,984, Notice of Allowance mailed Dec. 6, 2017", 11 pgs.
"U.S. Appl. No. 15/667,984, Response filed Oct. 23, 2017 to Non Final Office Action mailed Oct. 19, 2017", 7 pgs.
"European Application Serial No. 08840818.2, Communication Pursuant to Article 94(3) EPC Nov. 22, 2011", 4 pgs.
"European Application Serial No. 08840818.2, Extended European Search Report mailed Mar. 4, 2011", 6 pgs.
"European Application Serial No. 08840818.2, Intention to Grant mailed Mar. 26, 2015", 101 pgs.
"European Application Serial No. 08840818.2, Response filed May 18, 2012 to Communication Pursuant to Article 94(3) EPC Nov. 22, 2011", 11 pgs.
"European Application Serial No. 08840818.2, Response filed Jul. 6, 2010 to Communication pursuant to Rules 161(2) and 162 EPC mailed Jun. 4, 2010", 3 pgs.
"European Application Serial No. 08840818.2, Response filed Sep. 29, 2011 to Extended European Search Report mailed Mar. 4, 2011", 17 pgs.
"International Application Serial No. PCT/US2004/036451, International Search Report mailed Aug. 26, 2005", 1 pg.
"International Application Serial No. PCT/US2008/081310, International Preliminary Report on Patentability mailed Apr. 27, 2010", 10 pgs.
"International Application Serial No. PCT/US2008/081310, International Search Report mailed Jan. 6, 2009", 1 pg.
"International Application Serial No. PCT/US2008/081310, Written Opinion mailed Jan. 6, 2009", 9 pgs.
"International Application Serial PCT/US2008/066644, International Preliminary Report on Patentability mailed Dec. 17, 2009", 6 pgs.
"International Application Serial PCT/US2008/066644, International Search Report mailed Oct. 9, 2008", 1 pg.
"International Application Serial PCT/US2008/066644, Written Opinion mailed Oct. 9, 2008", 5 pgs.

Henkes, H., et al., "A New Device for Endovascular Coil Retrieval from Intracranial Vessels: Alligator Retrieval Device", American Journal of Neuroradiology, vol. 27, Issue 2, (Feb. 2006), 327-329.
U.S. Appl. No. 12/738,702 U.S. Pat. No. 9,827,084, filed Apr. 19, 2010, Intravascular Guideware Filter System for Pulmonary Embolism Protection and Embolism Removal or Maceration.
U.S. Appl. No. 15/093,916, filed Apr. 8, 2016, Intravascular Guideware Filter System for Pulmonary Embolism Protection and Embolism Removal or Maceration.
U.S. Appl. No. 15/667,984 U.S. Pat. No. 9,943,397, filed Aug. 3, 2017, Intravascular Guideware Filter System for Pulmonary Embolism Protection and Embolism Removal or Maceration.
U.S. Appl. No. 12/152,367 U.S. Pat. No. 9,149,609, filed May 14, 2008, Catheter for Removal of an Organized Embolic Thrombus.
"U.S. Appl. No. 15/093,916, Response filed Jan. 21, 2020 to Non Final Office Action mailed Jul. 18, 2019", 16 pages.
"U.S. Appl. No. 15/093,916, Notice of Allowance mailed May 15, 2020", 12 pages.
"U.S. Appl. No. 15/093,916, 312 Amendment filed Aug. 15, 2020", 12 pgs.
"U.S. Appl. No. 15/093,916, Corrected Notice of Allowability mailed Sep. 25, 2020", 4 pgs.
"U.S. Appl. No. 15/093,916, PTO Response to Rule 312 Communication mailed Sep. 1, 2020", 3 pgs.
"U.S. Appl. No. 17/000,074, Preliminary Amendment filed Feb. 2, 2021", 9 pgs.
"International Application Serial No. PCT/US2021/013410, International Preliminary Report on Patentability mailed May 10, 2022", 9 pgs.
"International Application Serial No. PCT/US2021/013410, International Search Report mailed May 18, 2021", 4 pgs.
"International Application Serial No. PCT/US2021/013410, Invitation to Pay Additional Fees and Partial Search Report mailed Mar. 23, 2021", 2 pgs.
"International Application Serial No. PCT/US2021/013410, Response filed Nov. 12, 2021 to Written Opinion mailed May 18, 2021", 7 pgs.
"International Application Serial No. PCT/US2021/013410, Written Opinion mailed May 18, 2021", 8 pgs.
"International Application Serial No. PCT/US2022/034507, Invitation to Pay Additional Fees mailed Nov. 1, 2022", 2 pgs.
"International Application Serial No. PCT/US2022/041672, International Search Report mailed Feb. 6, 2023", 4 pgs.
"International Application Serial No. PCT/US2022/041672, Written Opinion mailed Feb. 6, 2023", 10 pgs.
"U.S. Appl. No. 17/000,074, Examiner Interview Summary filed Feb. 20, 2023", 2 pgs.
"U.S. Appl. No. 17/000,074, Non Final Office Action mailed Mar. 22, 2023", 14 pgs.
"U.S. Appl. No. 17/000,074, Final Office Action mailed Oct. 26, 2023", 13 pgs.
"U.S. Appl. No. 17/000,074, Response filed Mar. 26, 2024 to Final Office Action mailed Oct. 26, 2023", 17 pgs.
"U.S. Appl. No. 17/000,074, Response filed Jul. 24, 2023 to Non Final Office Action mailed Mar. 22, 2023", 17 pgs.
"U.S. Appl. No. 18/410,989, Preliminary Amendment filed Feb. 1, 2024", 10 pgs.
"European Application Serial No. 21741545.4, Extended European Search Report mailed Mar. 18, 2024", 9 pgs.
"International Application Serial No. PCT/US2022/041672, International Preliminary Report on Patentability mailed Mar. 7, 2024", 12 pgs.
"U.S. Appl. No. 17/000,074, Non Final Office Action mailed Jun. 18, 2024", 17 pgs.
"U.S. Appl. No. 17/000,074, Examiner Interview Summary mailed Sep. 12, 2024", 2 pgs.
"U.S. Appl. No. 17/000,074, Final Office Action mailed Dec. 2, 2024", 17 pgs.
"U.S. Appl. No. 17/896,589, Response filed Feb. 2, 2025 to Non Final Office Action mailed Oct. 4, 2024", 12 pgs.
"U.S. Appl. No. 17/000,074, Response filed Feb. 3, 2025 to Final Office Action mailed Dec. 2, 2024", 15 pgs.

(56) References Cited

OTHER PUBLICATIONS

"U.S. Appl. No. 17/000,074, Non Final Office Action mailed Feb. 20, 2025", 17 pgs.
"European Application Serial No. 22862135.5, Extended European Search Report mailed Dec. 3, 2024", 9 pgs.
"International Application Serial No. PCT US2024 042567, International Search Report mailed Jan. 21, 2025", 4 pgs.
"International Application Serial No. PCT US2024 042567, Written Opinion mailed Jan. 21, 2025", 11 pgs.

* cited by examiner

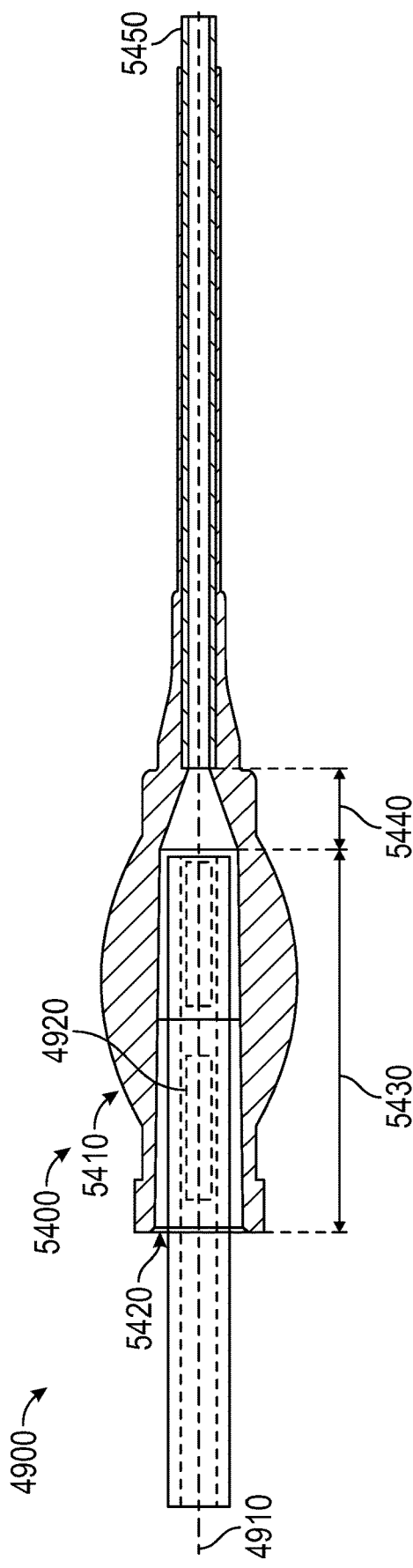
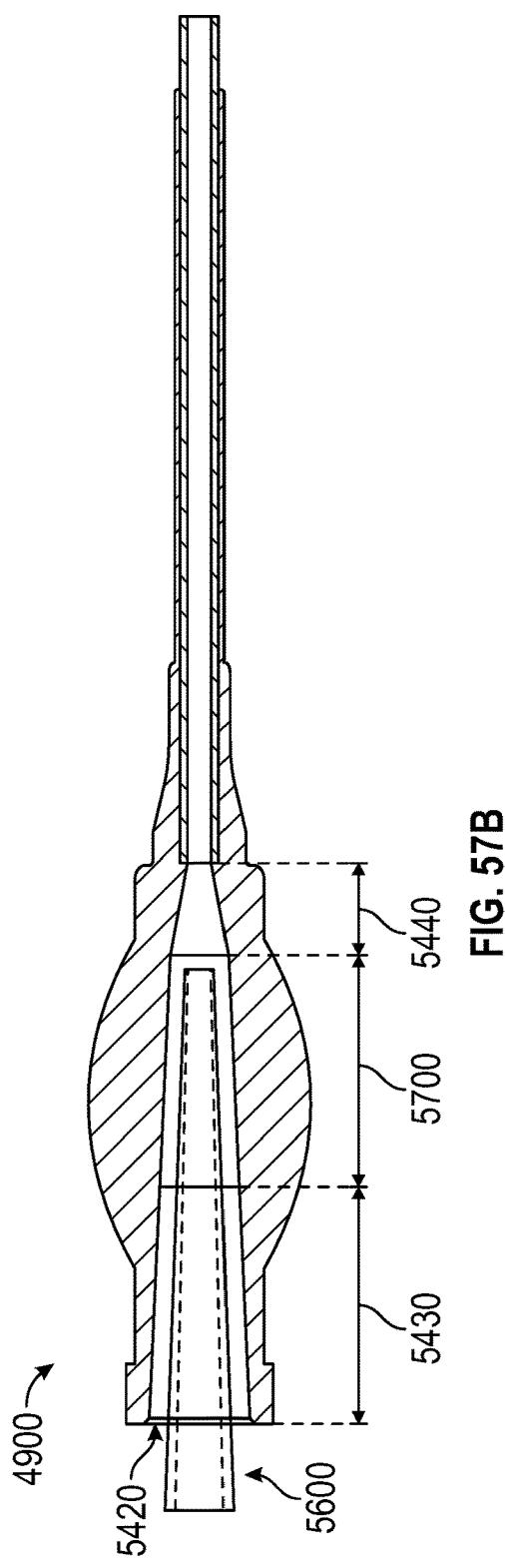
FIG. 57A
FIG. 57B

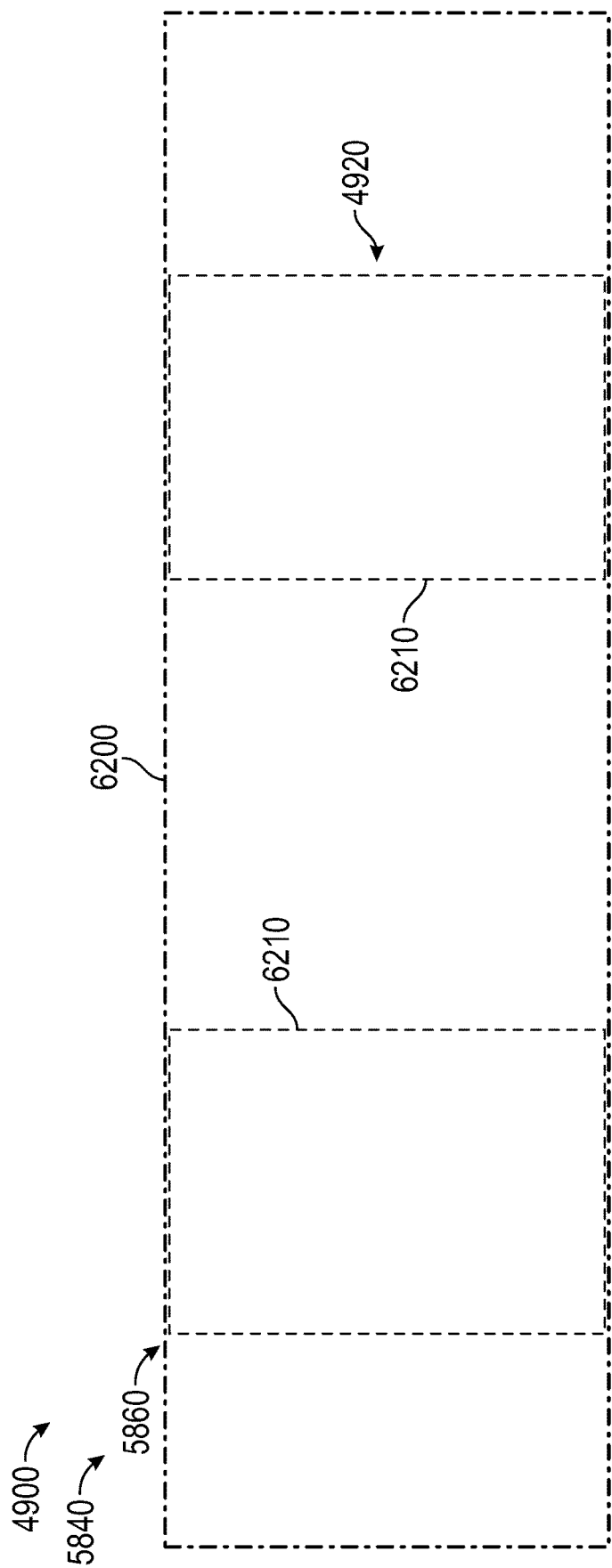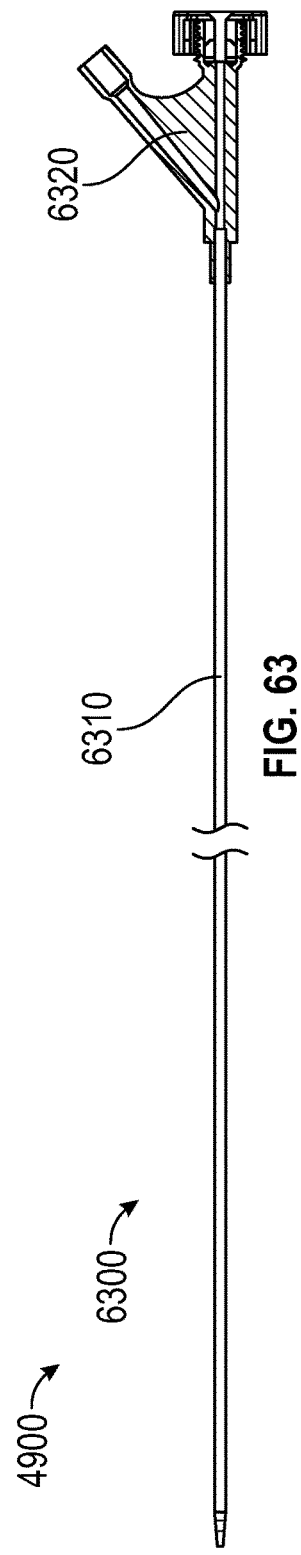

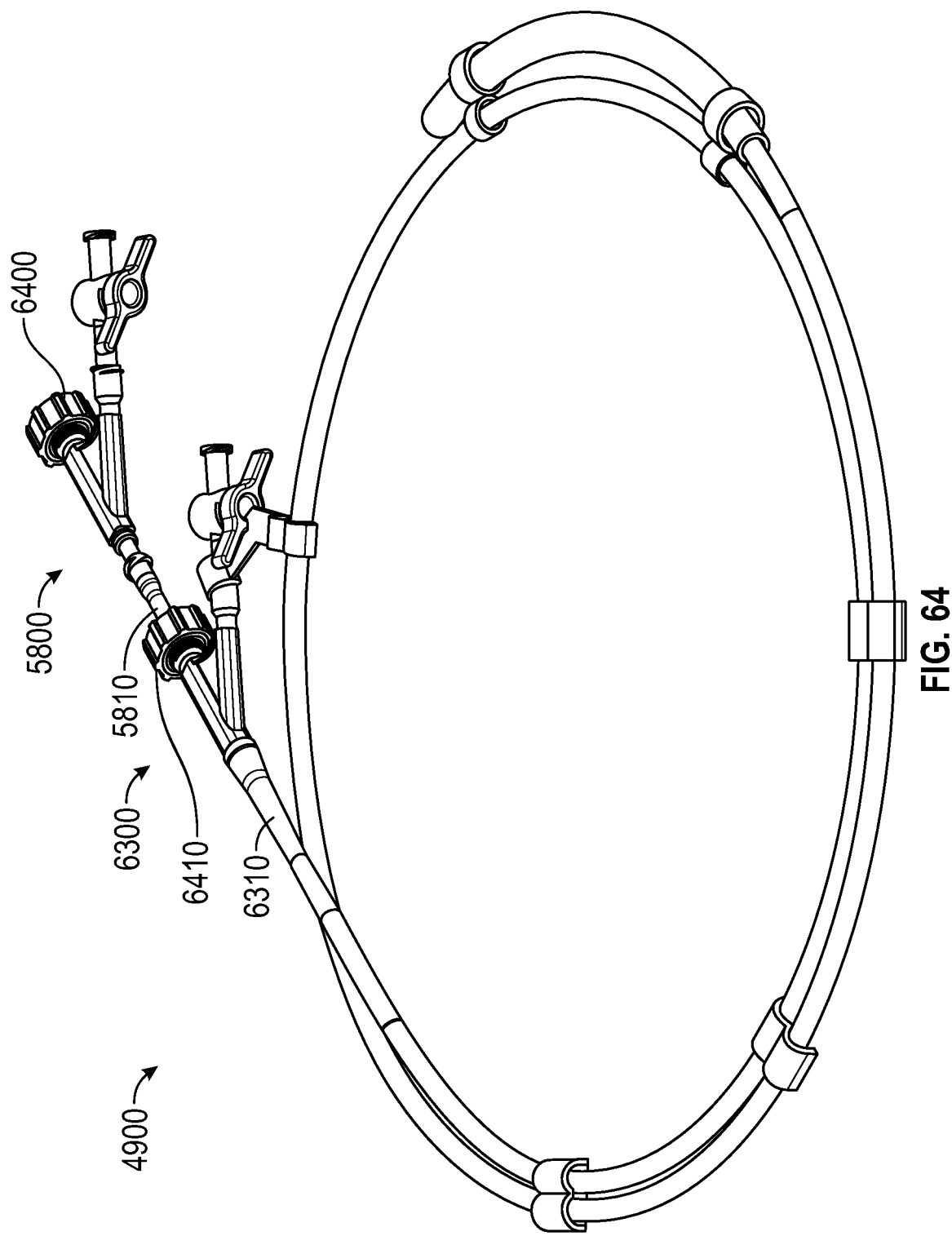

INTRA VASCULAR GUIDEWIRE FILTER SYSTEM FOR PULMONARY EMBOLISM PROTECTION AND EMBOLISM REMOVAL OR MACERATION

CLAIM OF PRIORITY

This application is a continuation-in-part of U.S. patent application Ser. No. 15/093,916, filed Apr. 8, 2016, titled "INTRA VASCULAR GUIDEWIRE FILTER SYSTEM FOR PULMONARY EMBOLISM PROTECTION AND EMBOLISM REMOVAL OR MACERATION," which is a continuation of U.S. patent application Ser. No. 12/738,702, filed on Apr. 19, 2010, which is a 371 national phase application of PCT International Application No. PCT/US2008/81310, filed on Oct. 27, 2008, and designating the United States of America, which claims the benefit from the earlier filed U.S. Provisional Application No. 61/000,465 filed Oct. 26, 2007, entitled "Intravascular Macerating Filter," and is hereby incorporated into this application by reference as if fully set forth herein.

CROSS REFERENCE TO RELATED APPLICATIONS

This patent application is related to patent application Ser. No. 12/152,367 filed on May 14, 2008, entitled "Catheter for Removal of an Organized Embolic Thrombus."

BACKGROUND

The present disclosure relates to a guidewire system and, more particularly, is for an intravascular guidewire filter system for pulmonary embolism protection and embolism removal or maceration.

DESCRIPTION OF THE PRIOR ART

Prior art devices have been used for embolization protection during treatment involving an intravascular intervention where it is not uncommon for large pieces of embolic debris to become dislodged during the debulking of vessels. In the case of deep vein thrombosis (DVT), the interventional treatment of deep vein thrombosis is accomplished by various methods. Historically, deep vein thrombosis has been treated with heparin since it was shown to reduce the occurrence of pulmonary embolism (PE). However, this modality of treatment often leaves the patient with long term debilitations since the underlying deep vein thrombosis is not treated, such debilitations including open sores, swelling, and continuous leg pain. Some physicians aggressively treat deep vein thrombosis by using either thrombectomy devices or fibrinolytics. In either case, such deep vein thrombosis treatment can result in pieces of thrombus debris being dislodged and which pieces can move to the lungs. If the thrombus debris is large enough to effectively inhibit a pulmonary function, it is classified as a pulmonary embolism. Institutions and physician practice for preventing pulmonary embolisms while performing deep vein thrombosis interventions vary. The current option for preventing a pulmonary embolism while performing a deep vein thrombosis intervention is to place a filter in the inferior vena cava (IVC). However, IVC filters come with their own set of shortcomings. IVC filters have been associated with thrombosis (they clot up on their own), filter migration, perforation of the and the like. IVC filters have been associated with increased mortality. Currently, some IVC filters are available as a removable type filter. Typically, a patient would come in a short time after the intervention for removal of the filter. However, if the patient neglects to make the follow-up visit in time, the filter can become difficult or impossible to remove. Furthermore, there is the expense of these filters. Given this choice of an IVC filter versus the risk of pulmonary embolism with no filter, some physicians view the treatment of deep vein thrombosis as problematic.

The purpose of the devices set forth in the present disclosure is to remove some of the obstacles for providing embolic protection during the treatment of deep vein thrombosis. The devices of the present disclosure do not have the hooks that penetrate the wall of the IVC. For a permanent or removable IVC filter, these hooks are needed to prevent filter migration. However, with a filter on a guidewire as used in the devices of the present disclosure, the risk of migration is mitigated by the fact that the physician can monitor the filter location throughout the intravascular procedure. The lack of hooks reduces the risk of injury or perforation of the IVC. Furthermore, the filter of the present disclosure is on a guidewire that must be removed at the end of the intravascular procedure. Therefore, there is considerably less risk that the filter of the present disclosure would become thrombosed since it is in the body while the patient is under a large amount of anti-thrombotics. Finally, the ease of installation and removal of the filter of the present disclosure is viewed as superior to implantable IVC filters. Extreme caution must be used when implanting a permanent or removable IVC filter since many of the IVC filters are not effective unless placed precisely. The removal of an IVC filter involves snaring the IVC filter and pulling it away from the wall of the IVC. Both are difficult. In the case of the devices set forth in the present disclosure, the filters of the device are merely unsheathed, the position of which can be proximal to the IVC if that is desired. The placement of the filter of the present disclosure is not as critical since it is only used throughout the intervention. The removal of the filter of the present disclosure is simpler since there is no snaring needed and the device has no hooks or ingrowth to the vessel.

One purpose of the devices set forth in the present disclosure is to provide easily deployed pulmonary embolism protection during a deep vein thrombosis intervention while simultaneously avoiding the need for long debulking times in the IVC with an AngioJet® thrombectomy device and catheter, thereby resulting in a lower hemolysis. The devices set forth in the present disclosure accomplish the same level of filter protection as a removable IVC filter during the procedure. The devices of the present disclosure overcome some of the associated risks with using IVC filters since it does not have the same migration prevention design features and does not have the complexity associated with snaring a filter device for retrieval. The filter device of the present disclosure is simpler to manufacture and easier to deploy than other marketed IVC filters. Furthermore the macerating aspect of the filter device of the present disclosure minimizes the run time of an AngioJet® thrombectomy device and catheter in the IVC. This minimization of the run time should be associated with less hemolysis. Thus, the designs set forth in the present disclosure provide a safer means for providing distal protection during a deep vein thrombosis intervention.

Another purpose of the devices of the present disclosure is to provide a nonocclusive retrieval device for pulling embolic debris proximally and removing it from the vasculature. With respect to a difficult and tough embolic debris removal, there are few or no effective interventional embolectomy tools. Sometimes, a Forgarty balloon is used via a surgical cutdown for debris removal. Some physicians try to use snares to pull tough embolic debris back into large guide catheters or even the interventional sheath. Nevertheless, bench testing reveals that large debris will be stripped off of snares as they are pulled into guides or interventional sheaths. In order to provide a successful embolectomy, the devices of the present disclosure provide for the use of a cooperatively flexible nitinol mesh as part of a capture sleeve and a means for pulling the debris into the nitinol mesh capture sleeve. In the case of some prior art embolectomy devices, the debris was brought into a nitinol mesh capture sleeve with an occlusion balloon on a wire. However, testing reveals that if the vessel diameter changes dramatically distal to the embolic debris to the mesh location, the thrombus debris may slide past the occlusion balloon since the occlusion balloon will not change in size dramatically. Furthermore, in a highly bifurcated anatomy, an occlusive balloon will encourage the embolic debris to float down alternative branches as the occlusion balloon is pulled proximally. A nitinol filter on a guidewire shown in the present disclosure is not occlusive and it changes size more dramatically than an occlusion balloon, thereby being more effective. The nitinol filters are shaped and designed for stiffness during pulling, but may be collapsed by compression interaction with a capture/delivery sheath and/or nitinol mesh capture sleeve, whereby the debris can be formed into smaller pieces (macerated) by the inwardly forced structure of the filter. The smaller pieces can then be more readily sized and compressed by the capture/delivery sheath and/or nitinol mesh capture sleeve for proximal removal through the capture/delivery sheath.

In general, the devices of the present disclosure are used to capture or trap embolic debris, either passively or actively, without the need for stopping blood flow. The trapped or pulled embolic debris is then either compressed in a simple tube sheath and/or expandable mesh sleeve and removed or can be minimized/macerated to a manageable size and treated by an AngioJet® thrombectomy device and catheter or lytics or can be of a clinically insignificant size so as to be resorbed by the body. The guidewire of the present disclosure is utilized for passage of devices over it, such as an AngioJet® thrombectomy catheter or other useful devices, in order to debulk or remove debris or to provide for the use of a stent or other devices.

SUMMARY OF THE DISCLOSURE

The general purpose of the devices set forth in the present disclosure is to provide an intravascular guidewire filter system for pulmonary embolism protection and embolism removal or maceration, i.e., the breaking down of embolic debris into smaller pieces. The primary and alternative embodiments consist of all or a plurality of basic components in combination, generally including one or more operator devices, a flexible 0.014" to 0.035" diameter guidewire, collapsible filters secured over and about the guidewire, a capture/delivery sheath, and a flexible mesh capture sleeve secured to the distal end of a capture sleeve positioning tube; many of the components are arranged telescopically.

The preferred embodiment of the present disclosure features a guidewire having a flexible proximal filter and a flexible distal filter located in tandem and proximal to a distal flexible tip. The flexible proximal filter and the flexible distal filter are constructed to provide for a gross filtration of embolic debris and are generally open in a proximal direction to accept the inflow of embolic debris and the like, whereas a filter end at the distal portion of the filter structure is structured with less porosity to capture pieces of embolic debris. The proximal ends of the proximal filter and the distal filter are fixed to the guidewire while the distal ends are free to traverse along, over and about the guidewire to facilitate the collapsing of each filter when the capture/delivery sheath or the capture/delivery sheath and the flexible mesh capture sleeve in sequence are advanced by operating devices over the proximal filter and the distal filter whereby the filters interface with and process debris in several ways. The capture/delivery sheath and the capture sleeve together can cause the filters to lengthen and cause the filters to easily collapse therein. At this conjuncture, two forms of embolic debris removal or treatment are used, one form is the direct physical engagement of the filters with the embolic debris and the other forum is the direct physical engagement of the filters with the embolic debris in combination with thrombolytics. In the first form, large embolic debris is trapped. If the embolic debris is proximal to the proximal filter, a thrombectomy catheter, such as an AngioJet® thrombectomy device or potentially an aspiration catheter may be used to remove the embolic debris. If the embolic debris resides within one or more of the filters, then, as the filters are sheathed for retrieval, soft embolic debris will be macerated by one or more of the filters as they are sheathed. The distal filter is a backup to catch any larger soft embolic debris that is not caught by the proximal filter. Thus, as both proximal and distal filters are sheathed, all soft embolic debris is macerated into smaller pieces where some debris may be trapped and some debris of inconsequential size may flow distally, if not captured. In the case where the thrombus debris in the filters is tougher and organized, sheathing will capture the thrombus debris within the filters for debris removal. Situations where this form of debris destruction is a viable means of protection involve venous interventions where the small debris is resolved by the lungs. In the other form, arterial interventions using the above mentioned method and when used in combination with thrombolytics, the soft thrombus is broken into smaller debris which is readily dissolved by thrombolytics.

According to one or more embodiments of the present disclosure, there is provided an intravascular guidewire filter system for pulmonary embolism protection and embolism removal or maceration including a flexible guidewire, a distal filter and a proximal filter each firmly and slideably affixed to the guidewire where each filter includes a proximally located open end and a distally located filter end, a capture/delivery sheath attached at its proximal end to a capture/delivery sheath operator which can be extended over a greater portion of the flexible guidewire, a flexible capture sleeve being open in a distal direction, and a capture sleeve positioning tube which is aligned within the capture/delivery sheath where the distal end of the capture sleeve positioning tube is attached to the proximal end of the capture sleeve and where the proximal end of the capture sleeve positioning tube is attached to a capture sleeve operator.

The devices of the present disclosure provide an intravascular emboli capture and retrieval system for intra vascular embolism protection and embolism removal or maceration.

One significant aspect and feature of the devices of the present disclosure is the use of an intravascular guidewire filter system for pulmonary embolism protection and embolism removal or maceration which system comprises a telescoping capture mechanism having (a) a capture/delivery sheath and a capture/delivery sheath operator; (b) a guidewire having flexible distal and proximal filters with a preformed memory shape, and (c) a flexible capture sleeve (mesh), a capture sleeve positioning tube and a capture sleeve operator.

One significant aspect and feature of the devices of the present disclosure is a device that is used to capture, trap or macerate embolic debris either passively or actively without the need for stopping blood flow.

Another significant aspect and feature of the devices of the present disclosure is a device having one or more of nitinol filters mounted on a conventional guidewire.

Another significant aspect and feature of the devices of the present disclosure is a device having one or more nitinol filters which can be used to trap embolic debris.

Another significant aspect and feature of the devices of the present disclosure is a device having one or more nitinol filters which can be used to macerate embolic debris.

Another significant aspect and feature of the devices of the present disclosure is the use of filters which are designed for stiffness during embolic debris pulling use but which filters are collapsible for removal.

Another significant aspect and feature of the devices of the present disclosure is a device having one or more nitinol filters which can be used to remove embolic debris.

Another significant aspect and feature of the devices of the present disclosure is a device that uses filters which have an expanded memory position.

Another significant aspect and feature of the devices of the present disclosure is a device where the proximal end of a nitinol filter is fixedly and directly attached to guidewire.

Another significant aspect and feature of the devices of the present disclosure is a device where the distal end of a nitinol filter slideably engages a guidewire in order to allow collapsing or expanded deployment of the nitinol filter.

Another significant aspect and feature of the devices of the present disclosure is a device that uses filters which are deployed, such as, from the lumen of a capture/delivery sheath.

Another significant aspect and feature of the devices of the present disclosure is a device that uses filters which are deployed, such as, from the lumen of a delivery sheath and then retrieved through a separate capture sheath that has been exchanged with the delivery sheath over the guidewire.

Another significant aspect and feature of the devices of the present disclosure is a device that uses filters which are compressible for proximal retraction, such as by the action of a capture/delivery sheath and/or a mesh capture sleeve.

Another significant aspect and feature of the devices of the present disclosure is a device having one or more filters generally open in a proximal direction to accept the inflow of embolic debris and a distal portion of the filter having a structure with a closer weave in order to capture pieces of embolic debris but which allows the flow of blood there through.

Another significant aspect and feature of the devices of the present disclosure is a device where proximall/distal configurations can use as many filters as needed and in any shape and size as desired.

Another significant aspect and feature of the devices of the present disclosure is the use of a flexible mesh capture sleeve which can be all nitinol or which can be nitinol with a polymer interwoven therein to interface with embolic debris.

Another significant aspect and feature of the devices of the present disclosure is a device having filter diameters from 2 mm to 48 mm.

Another significant aspect and feature of the devices of the present disclosure is a device where regular treatment devices can be passed over the proximal portion of the guidewire for use as a regular guidewire.

Another significant aspect and feature of the devices of the present disclosure is a device having the ability to capture large organized embolic debris.

Another significant aspect and feature of the devices of the present disclosure is a device having the ability to capture large and small embolic debris.

Another significant aspect and feature of the devices of the present disclosure is a device having the ability to temporarily capture debris which may later be removed by manual aspiration or by the use of an AngioJet® thrombectomy device and catheter or which may be treated by thrombolytics.

Another significant aspect and feature of the devices of the present disclosure is a device having the ability to macerate debris to a clinically insignificant size (depending on the area of the body) or to a size which can be pharmacologically treated or removed by another device, such as an AngioJet® thrombectomy device and catheter.

Another significant aspect and feature of the devices of the present disclosure is a device having the ability to macerate non-embolic debris, such as a stationary thrombus, by pulling the device through such an obstruction.

Having thus briefly described one or more embodiments of the present disclosure, and having mentioned some significant aspects and features of the devices of the present disclosure, it is the principal object of the present disclosure to provide an intravascular guidewire filter system for pulmonary embolism protection and embolism removal or maceration or for use with other medical devices.

BRIEF DESCRIPTION OF THE DRAWINGS

Other objects of the present disclosure and many of the attendant advantages of the devices set forth in the present disclosure will be readily appreciated as the same becomes better understood by reference to the following detailed description when considered in connection with the accompanying drawings, in which like reference numerals designate like parts throughout the figures thereof and wherein:

FIG. 57A illustrates an example of the catheter assembly with the installation brace of FIG. 56 received in the interior socket.

FIG. 57B illustrates an example of the catheter assembly with another example of the installation brace received in the interior socket.

FIG. 62 illustrates an example of the catheter assembly, including capture sleeve and the filters.

FIG. 63 illustrates an example of the catheter assembly including a capture sleeve delivery catheter.

FIG. 64 illustrates an example of the catheter assembly 4900.

DETAILED DESCRIPTION OF THE PREFERRED EMBODIMENTS

Figure 1:
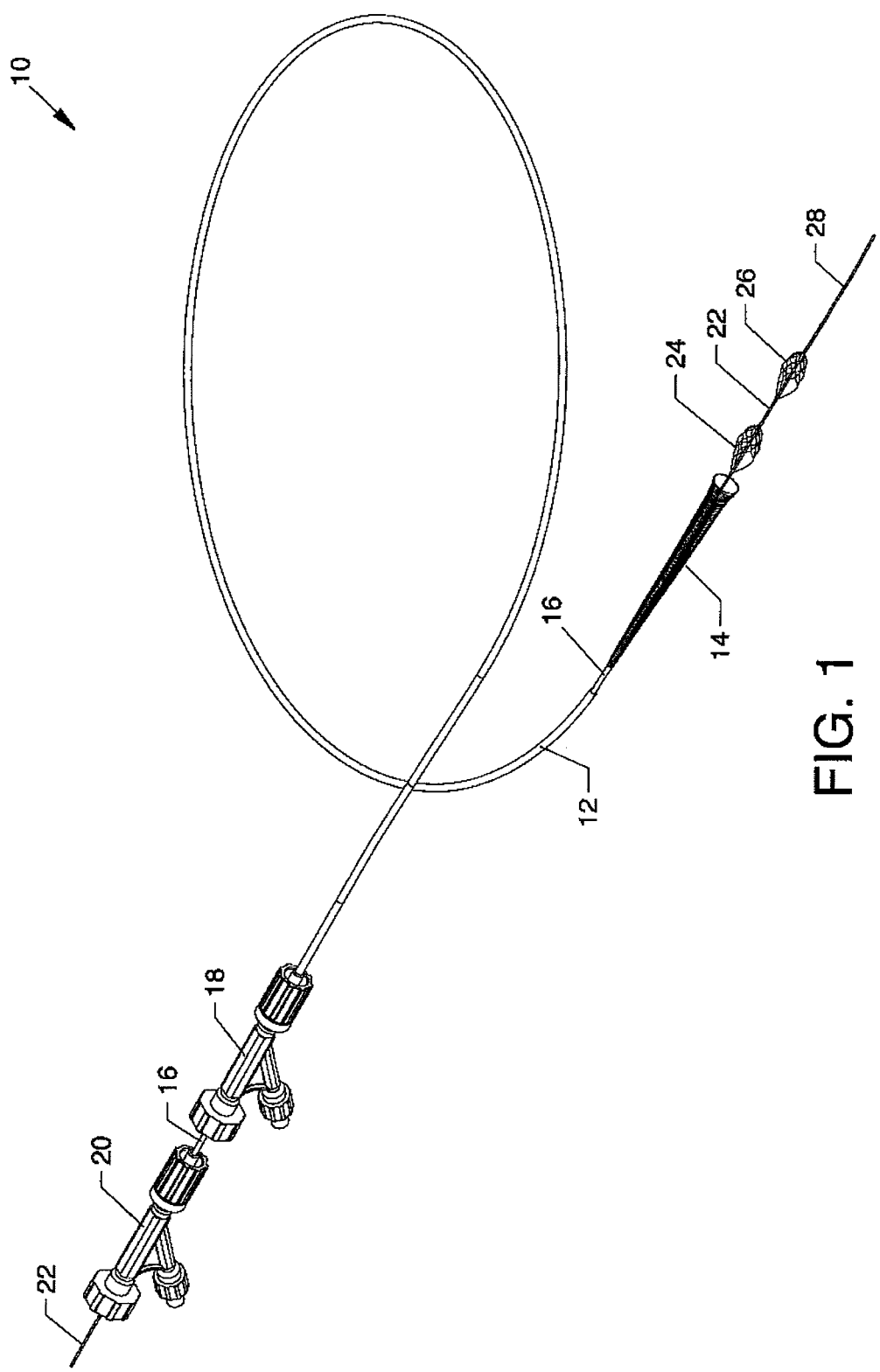
FIG. 1 is an isometric overview of the intravascular emboli capture and retrieval system for intravascular embolism protection and embolism removal or maceration.

FIG. 1 is an isometric overview of the intravascular emboli capture and retrieval system for intravascular embolism protection and embolism removal or maceration, 10. Generally, this preferred embodiment is useful in blood vessels of 8*mm* or less to capture embolic debris, although maceration of such is also associated therewith. For vessels of larger than 8 mm in size, appropriate modifications to the sizing of the components of this embodiment, as known to those of skill in the art, are able to be freely substituted in order to capture or macerate emboli as dictated by each individual patient and scenario. Fully or partially visible components of the devices set forth in the present disclosure include a multiple function flexible capture/delivery sheath 12, a flexible distally located capture sleeve 14 shown in memory shape consisting of a nitinol and polymer mesh (shown in FIG. 3) secured to the distal end of a flexible capture sleeve positioning tube 16, the latter of which is shown extending distally from within the capture/delivery sheath 1, a capture/delivery sheath operator 18 in the form of a manifold attached to the proximal end of the capture/delivery sheath 12, a capture sleeve operator 20 in the form of a manifold in general longitudinal alignment with the capture/delivery sheath operator 18, a flexible guidewire 22 aligning with and extending through the capture sleeve operator 20, the capture/delivery sheath operator 18, the capture/delivery sheath 12, the capture sleeve positioning tube 16, through the capture sleeve 14 and through a flexible preformed memory shaped proximal filter 24 and a flexible preformed memory shaped distal filter 26. The guidewire 22 also includes a distally located flexible tip 28. The guidewire 22 can also be coated with a Teflon® coating.

Multiple function capture/delivery sheath 12 is depicted here as one aspect of the present disclosure. Those of skill in the art, however, are aware of the need to have a delivery sheath as small as possible in order to place filters 24 and 26 past the embolic debris. A large sheath is then required to act as the capture sheath since it also now contains embolic debris within the filters. It is well known in the art to perform an exchange of sheaths over a guidewire in order to facilitate specific actions during the procedure. All embodiments of the present disclosure should be read as including either a combination capture/delivery sheath or separately sized capture and delivery sheaths for these purposes.

Figure 2:
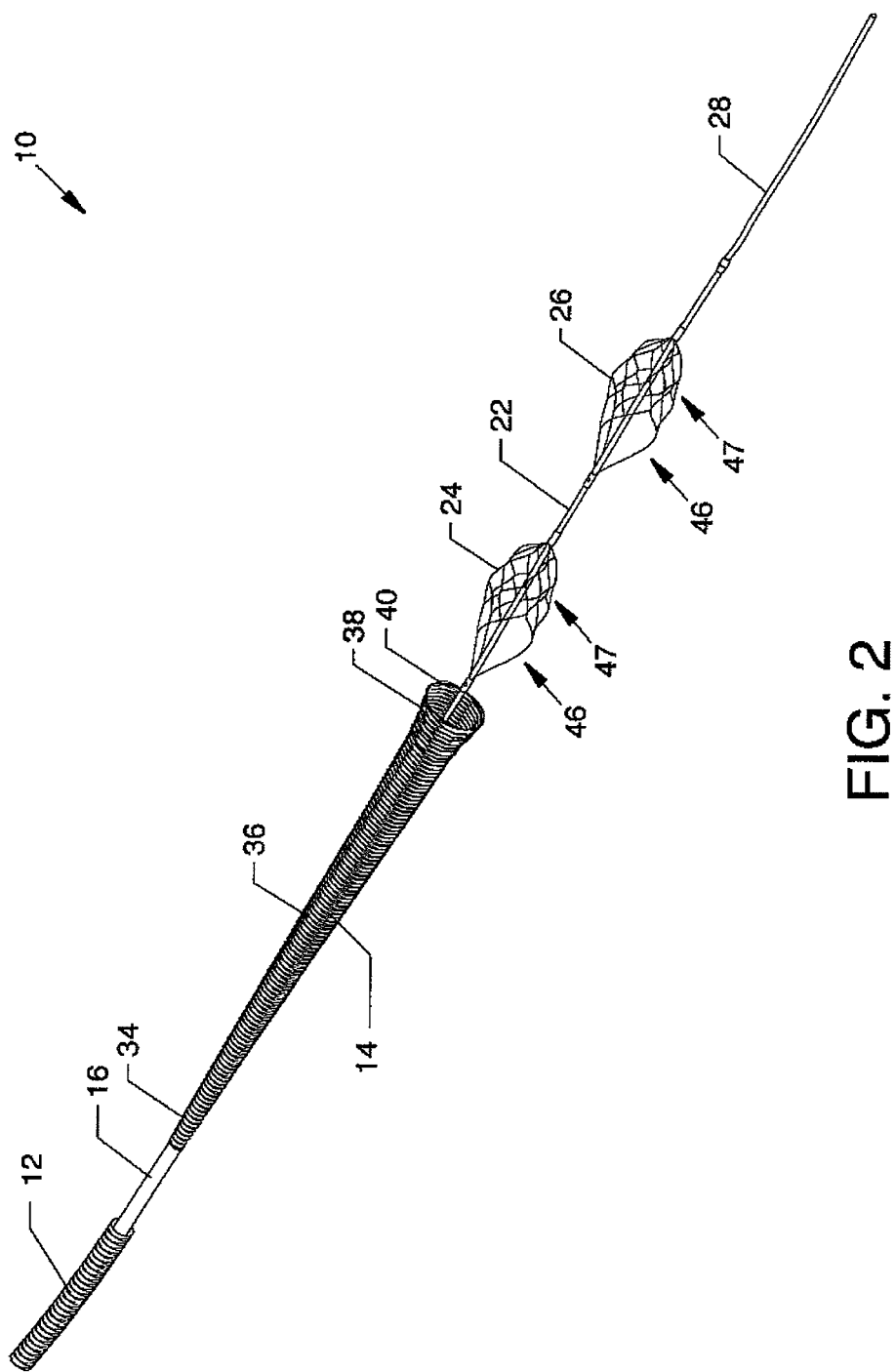
FIG. 2 is an isometric view of the components of the filter system located at the distal region of FIG. 1.

FIG. 2 is an isometric view of the components located at the distal region. The components maintain a coaxial relationship along and about the greater portion of the longitudinal axis comprising of inner, middle and outer components. The inner components consist of the guidewire 22, the proximal filter 24, the distal filter 26, and the flexible tip 28, the middle components consist of the capture sleeve 14 and the attached capture sleeve positioning tube 16, and the outer component consists of a capture/delivery sheath 12 made of a flexible spiral or woven flexible plastic material or other suitable flexible material. The inner, middle and outer components maintain a coaxial relationship. Some of the outer and middle components are also attached to the capture/delivery sheath operator 18 and the capture sleeve operator 20, respectively. More precisely, the capture sleeve 14 is attached to the capture sleeve operator 20 by a mutually attached capture sleeve positioning tube 16, and the capture/delivery sheath 12 is connected directly to the capture/delivery sheath operator 18. Preferably, the capture/delivery sheath 12 includes a hydrophilic coating to enhance deliverability along the vasculature or other structures and can be made of a flexible plastic material such as Pebax® plastic or another suitable flexible material.

Figure 3:
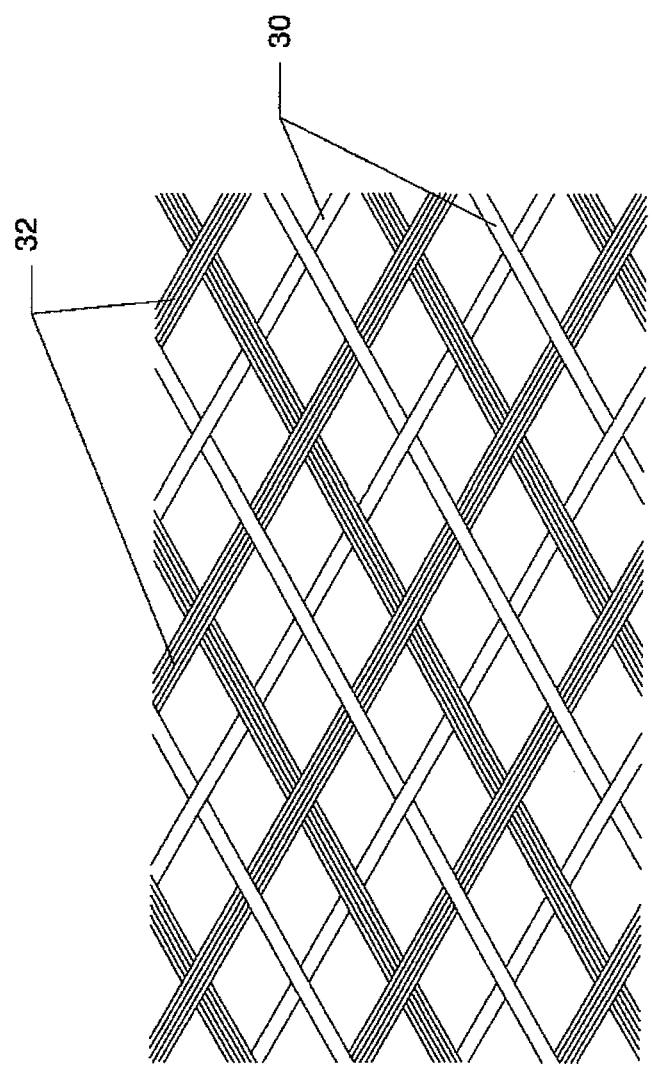
FIG. 3 is a view of the woven mesh comprising a flexible capture sleeve.

The geometrically configured flexible capture sleeve 14 is generally of a flared tubular shape and consists of a woven mesh preferably consisting of single nitinol strands 30 and multiple polymer strands 32, shown in a representative section in FIG. 3. The capture sleeve 14 is heat treated or otherwise treated to have an expanded memory shape. A substantially constant diameter proximal section 34 of the capture sleeve 14 is attached to the distal end of the flexible capture sleeve positioning tube 16 of braided polyimide, or alternatively of flexible stainless steel, by an adhesive, a welded, or other suitable method. The capture sleeve 14 also includes a flared midsection 36 extending distally from the proximal section 34 to a flared distal section 38 where, preferably, the degree of flare of the flared distal section 38 exceeds the flare of the flared midsection 36 in order to readily accommodate entry of embolic debris or of a filter into the capture sleeve 14. Preferably, the flared midsection 36 and the flared distal section 38 can assume a memory expanded flare shape, but are conformal within a confine and are expandingly conformal to embolic debris which may be urged therethrough. The distal annular edge 40 of the capture sleeve 14 is prevented from fraying by melting the ends of the polymer strands 32 with a thermal or laser source or some other suitable method. The structure of the similarly constructed proximal filter 24 and the distal filter 26 are described in FIG. 4 and other figures.

Figure 4:
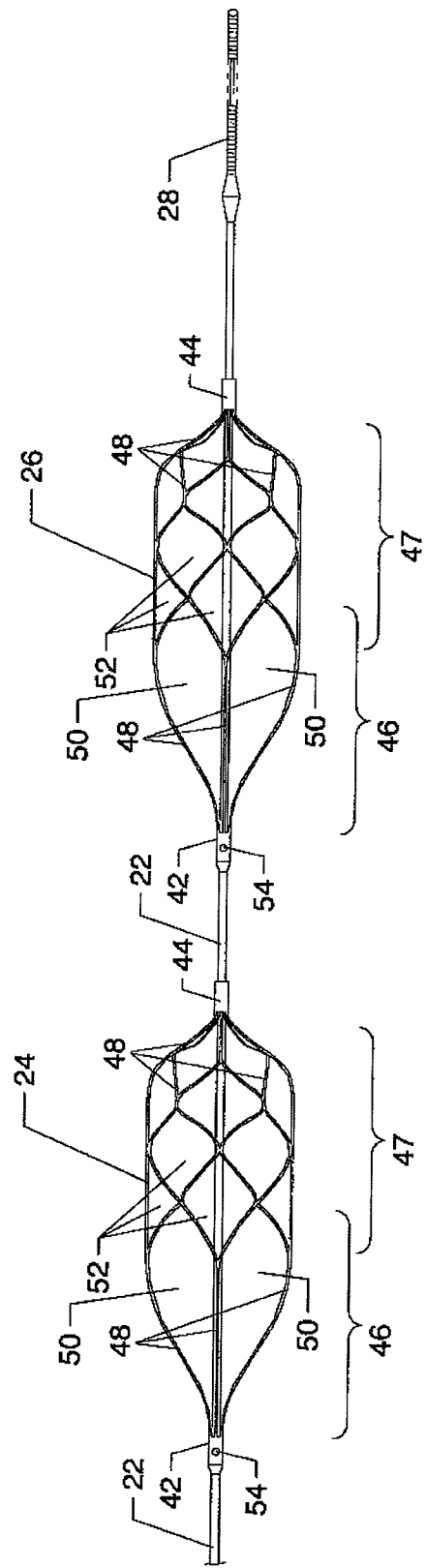
FIG. 4 is a side view of the distal end of the guidewire filter system including the similarly constructed preformed memory shaped proximal filter and distal filter.

FIG. 4 is a side view of the distal end of the guidewire 22 including the similarly constructed proximal filter 24 and distal filter 26. The preformed memory shaped proximal filter 24 and distal filter 26 are preferably formed as a one-piece structure where a configured multiply slotted nitinol tube has been expanded and heat treated in order to maintain a filter shape. The proximal tube 42 of the proximal filter 24 (and distal filter 26) is aligned over and about the guidewire 22 and is affixed and anchored thereto, preferably by the use of an adhesive which is applied through one or more holes 54 extending through the proximal tube 42 which, preferably, is or are aligned to one or more corresponding holes (not shown) in the guidewire 22. The distal tube 44 aligns over and about and slidingly engages the guidewire 22. The use of the fixed proximal tube 42 and the slideable distal tube 44 enables the proximal filter 24 and distal filter 26 to be flexibly and expandingly deployed and to be flexibly, compressingly and elongatingly collapsed along and about its longitudinal axis and along the guidewire 22, whereby a lower filter profile is provided in order to facilitate removal. Collapsing of the proximal filter 24 and distal filter 26 is assisted by engagement of the capture sleeve 14, the capture/delivery sheath 12, or both, as later described in detail. The proximal end of the proximal filter 24 (and distal filter 26) including the proximal tube 42 and the distal end of the proximal filter 24 (and distal filter 26) including the distal tube 44 have multiple strands of nitinol 48 extending therefrom and are distributed therebetween forming an angulated circumferential structure to provide openings which are substantially diamond shaped. For example, three widely spaced diverging nitinol strands 48 extend distally from the proximal tube 42 in order to form a proximally located open end 46 having multiple large openings 50. The nitinol strands 48 are further divided and then converge to form a plurality of small openings 52 in a band which are offset from and alternating with the band of the large openings 50. The division and convergence is repeated one or more times in a distal direction to create additional bands of small openings 52. The size of the small openings 52 is convergingly reduced adjacent the distal tube 44. The bands of small openings 52 forms the distally located filter end 47 which is in the shape of a tubular-like elongated web.

The large openings 50 are utilized for entry of an embolism or embolic or other debris into the proximal filter 24 and the distal filter 26. Depending on the size of the embolism or embolic debris, maceration may be partially accomplished by the initial impingement thereof on the nitinol strands 48 forming the large openings 50 at the open end 46. Subsequently, such macerated or appropriately sized embolisms or embolic or other debris can be filteringly captured by the plurality of small openings 52 forming the distally located filter end 47 to be further processed such as by compression, further macerated or a combination thereof using previously described components and features set forth herein. Although the large and small openings 50 and 52 are substantially diamond shaped, other shaped openings or configurations could also be used. The distal filter 24 and the proximal filter 26 and filters of alternative embodiments are shaped and designed for stiffness during use, but are flexible enough to be collapsed by compression during interaction with the capture/delivery sheath 12 and/or the nitinol mesh capture sleeve 14.

Figure 5:
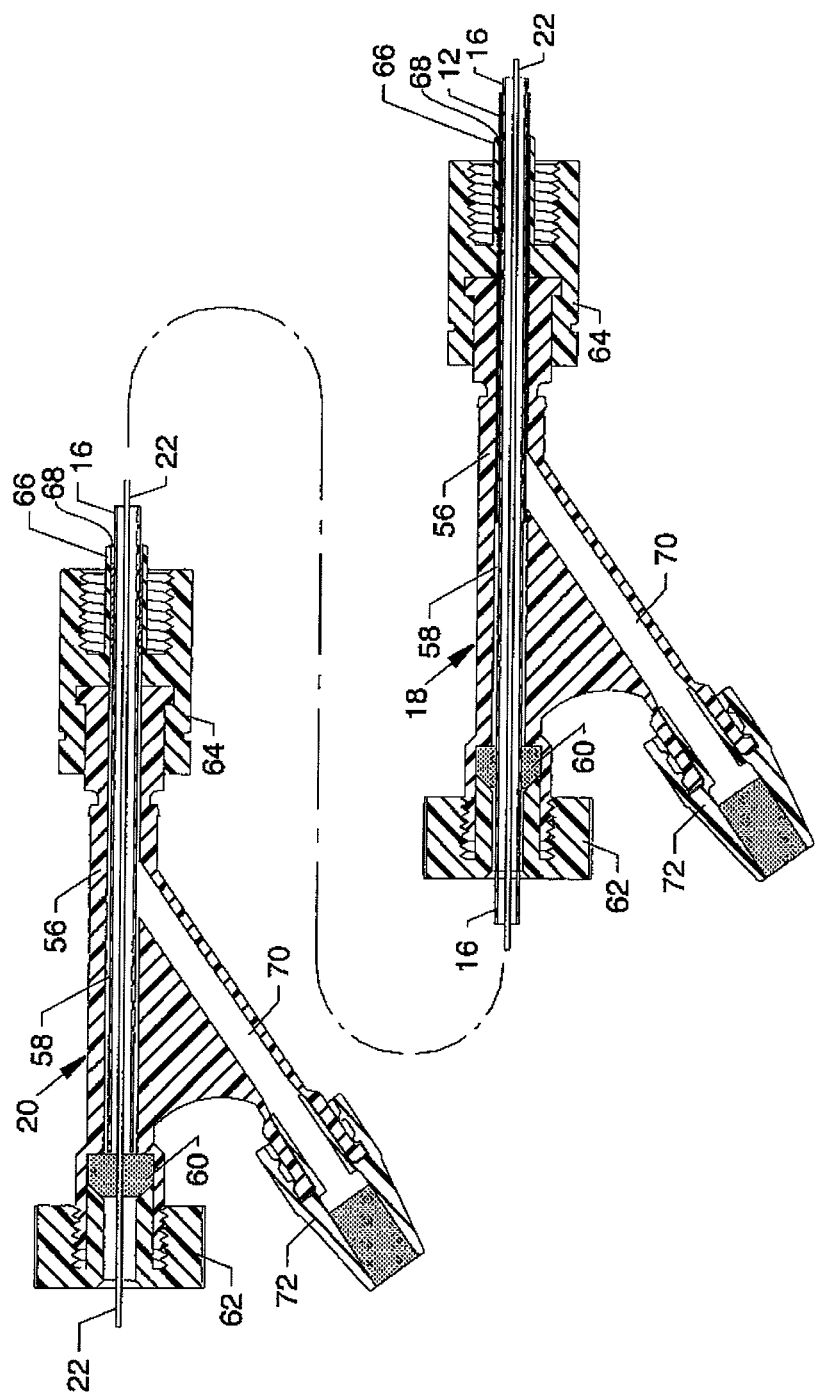
FIG. 5 is a segmented cross section view of the capture/delivery sheath operator and the capture sleeve operator.

FIG. 5 is a segmented cross section view of the capture/delivery sheath operator 18 and the capture sleeve operator 20, each in the faun of a manifold found commonly in the art. The capture/delivery sheath operator 18 and the capture sleeve operator 20 are used in a variable end-to-end alignment, such as shown in FIG. 1, and are used to telescopingly position the distally located components at the distal end using coaxially aligned tubular structures, the relationship of which is described with reference to FIG. 2. Briefly described, each operator includes a manifold body 56, a central passageway 58 extending along the manifold body 56, a seal 60, a hemostasis valve 62, a Luer connector 64, a tubular extension 66 (including a tubular passageway 68) extending through the Luer connector 64, a branch passageway 70 and a cap 72 which may be in the form of a Luer fitting.

The proximal end of the capture/delivery sheath 12 extends partially along the central passageway 58 of the capture/delivery sheath operator 18 and is positionally fixed therein by the use of an adhesive or another suitable method at the annular junction of the capture/delivery sheath 12 and the tubular extension 66 in the Luer connector 64 of the capture/delivery sheath operator 18. Generally, the capture/delivery sheath 12 can be positionably, telescopingly and variably aligned directly over, about and along portions of the capture sleeve positioning tube 16, over, about and along the connected capture sleeve 14, over, about and along the distal section of the guidewire 22, and over, about and along and the proximal filter 24 and the distal filter 26 which are located at the distal portion of the guidewire 22.

The proximal end of the capture sleeve positioning tube 16 extends partially within and along the central passageway 58 of the capture sleeve operator 20 and is fixed therein by the use of an adhesive or another suitable method at the annular junction of the capture sleeve positioning tube 16 and the tubular extension 66 in the Luer connector 64 of the capture sleeve operator 20. Additionally, the capture sleeve positioning tube 16 extends distally to enter the hemostasis valve 62, the seal 60, through the central passageway 58 of the capture/delivery sheath operator 18, and thence through the capture/delivery sheath 12 to finally connect to the distally located capture sleeve 14. The capture sleeve operator 20 can be used to slidingly position the capture sleeve positioning tube 16 (having the connected capture sleeve 14) along and within the capture/delivery sheath 12 in order to longitudinally position the capture sleeve 14 out of the influence of the capture/delivery sheath 12 or to return the capture sleeve 14 into the influence of the capture/delivery sheath 12. The seal 60 of the capture/delivery sheath operator 18 provides a slight pressure, which can easily be overcome, against the circumference of the capture sleeve positioning tube 16 in order to maintain the adjustable position of the capture sleeve positioning tube 16 with respect to the capture/delivery sheath operator 18 and to other associated telescopic components. Generally, as previously explained, the capture sleeve 14, which is connected to the capture sleeve positioning tube 16, can be positionably, telescopingly, and variably aligned directly over and about the guidewire 22 and the distal and proximal filters 24 and 26, respectively. Additionally, the seal 60 of the capture sleeve operator 20 provides a slight pressure which can be easily overcome against the circumference of the guidewire 22 in order to maintain the adjustable position of the guidewire 22 with respect to the capture sleeve operator 20 and to the other associated telescopic components.

MODE OF OPERATION

The mode of operation of the intravascular guidewire filter system 10 for the filtering and removal of various sized pieces of organized embolic debris is now described with reference to FIGS. 6-9, as well as understood reference to previously described figures in general, in this embodiment and in a closely related association with the alternative embodiments, one or more components may be preloaded prior to their use and are used in a telescopic fashion, whereby the capture/delivery sheath operator 18 and the capture sleeve operator 20 can be appropriately spaced and positioned longitudinally with respect to each other in order to change, affix, adjust or otherwise suitably influence the positional relationship of the distally located components, such as the capture/delivery sheath 12 and the capture sleeve 14 with respect to each other, as well as the closely associated and corresponding capture sleeve positioning tube 16. The guidewire 22, including the proximal filter 24 and the distal filter 26, is also positionable with respect to the components of the intravascular guidewire filter system 10 just referenced in this paragraph. The capture/delivery sheath operator 18, the capture sleeve operator 20 and the guidewire 22, including the attached proximal filter 24 and the distal filter 26 of this embodiment, can be operated independently one or more at a time in order to effect particular positional and functional relationships. The capture/delivery sheath operator 18 and the capture sleeve operator 20 associated with the capture/delivery sheath 12 and the capture sleeve 14 and associated positioning tubes, as well as the guidewire 22, can be operated individually or unitarily two or more at a time. In the alternative embodiments of the devices set forth in the present disclosure, the structure and/or use of the filters located on the guidewire 22, such as shown in use with the preferred embodiment, may be reoriented reconfigured, reversed, resized or otherwise changed or modified within the scope and teachings of the present disclosure to be used in lieu of the proximal filter 24 and/or the distal filter 26.

Figure 6:
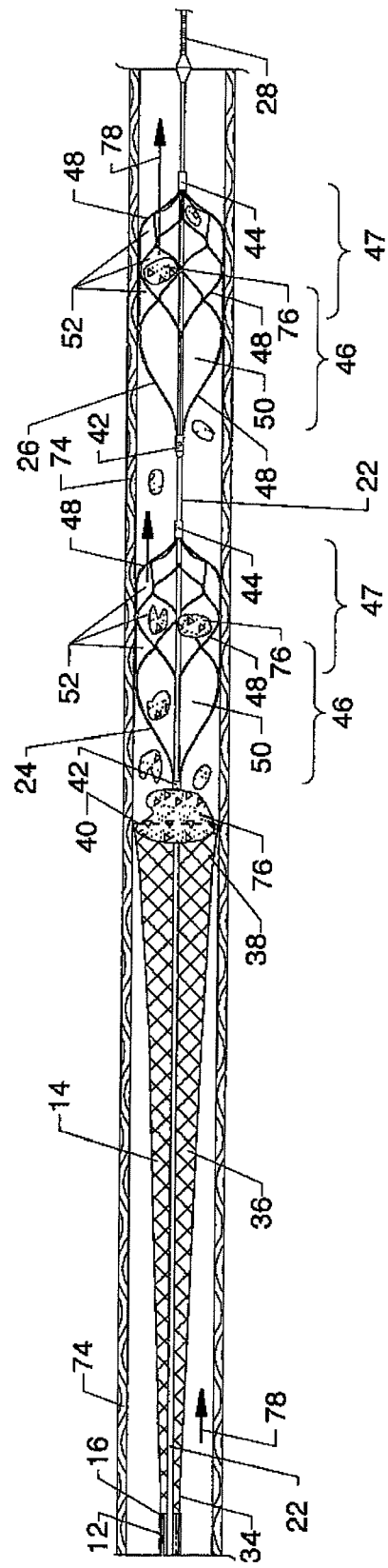
FIG. 6 is a view showing the proximal filter (in cutaway view) and the distal filter along the guidewire deployed and aligned in a blood vessel.

Use of the devices described in the present disclosure is initiated by insertion of the guidewire 22 and attached collapsed proximal filter 24 and distal filter 26 into the vasculature in cooperation with a smaller introducer sheath, such as known in the art, which is separate from the capture/delivery sheath 12. The distal end of the guidewire 22 and the proximal filter 24 and distal filter 26 are positioned through and beyond the embolic debris or area of treatment by use of the smaller introducer sheath, whereupon the smaller introducer sheath is removed in order to allow the automatic deployed expansion of the proximal filter 24 and the distal filter 26 which filters, preferably, intimately engage the inner circumference of a blood vessel 74 as shown in FIG. 6. The method of insertion into the vasculature of the guidewire 22 and attached collapsed proximal filter 24 and distal filter 26 in cooperation with a smaller introducer sheath, as set forth for this preferred embodiment, applies in general to one or more alternative embodiments on which, correspondingly, also include these or other automatically deployable, collapsible and expandable filters of various orientations, various features and various configurations. Interventional procedures or treatment, such as provided by, but not limited to, the use of an AngioJet® thrombectomy device and catheter, stenting or angioplasty could also be used at this point with protection against distally flowing embolic debris provided by the expanded proximal filter 24 and distal filter 26. Once the interventional procedure is complete, the physician could use fluoroscopy to verify that the proximal filter 24 and distal filter 26 were not occluded with embolic debris. Additionally, if there was an embolic thrombotic debris, an AngioJet® thrombectomy device and catheter could be advanced to treat any embolic debris proximal to the proximal filter 24 and the distal filter 26, as required.

Subsequent to the initial placement of the proximal filter 24 and the distal filter 26 and any interventional procedures, placement of stents, angioplasty or other treatments and trapping of the embolic debris, the capture/delivery sheath 12 including the capture sleeve 14 compressed and suitably located within the distal portion thereof, and also including the capture sleeve positioning tube 16, would engage and be delivered by simultaneous advancement distally over the guidewire 22 by distally directed positioning of the capture/delivery sheath operator 18 and the capture sleeve operator 20. Such delivery and advancement is continued until the capture sleeve 14 within the capture/delivery sheath 12 is in a position for suitable automatic expanded deployment to its memory shape proximal to the embolic debris trapped by the proximal filter 24 and the distal filter 26 by proximally directed positioning of the capture/delivery sheath 12 a short distance by manipulation of the capture/delivery sheath operator 18. The capture/delivery sheath 12, as thus distally positioned, is subsequently utilized and standing by for engagement over and about the distal filter 24 and the proximal filter 26 for capturing and removal of embolic thrombotic debris which is trapped by the proximal filter 24 and the distal filter 26, as later described in detail for this embodiment. With corresponding respect to this preferred embodiment and the alternative embodiments, delivery and positioning of the capture/delivery sheath 12 and the capture sleeve 14 is thus accomplished and such delivered components are standing by for the capture and removal of the embolic thrombotic debris which is trapped by automatically deployable, collapsible and expandable filters, such as the proximal filter 24 and the distal filter 26 of the preferred embodiment and filters of like orientation, various orientations, various features and various configurations of one or more alternative embodiments.

Thus, the initial placement of the guidewire 22, the attached proximal filter 24 and the distal filter 26, and the delivery and deployment of the capture sleeve 14, as well as the other associated structures have been described, the methods of which can generally be used with respect to both the preferred embodiment and the alternative embodiments. Capture and removal of entrapped embolic debris 76 is subsequently described with reference first to the preferred embodiment and with reference to the alternative embodiments wherein the general procedures are closely related or are the same.

In FIG. 6 and with respect to the preferred embodiment, a cutaway view is shown in partial cross section and partial cutaway view in the capture mode showing the proximal filter 24 (in cutaway view) and the distal filter 26 and the guidewire 22 deployed and aligned within a blood vessel 74 showing a large piece of embolic debris 76 located proximal to the proximal filter 24 being initially engaged by the flared distal section 38 of the capture sleeve 14. Other smaller pieces of embolic debris 76 are shown in the distally located filter end 47 of the proximal filter 24 which pieces have been deposited therein by passing through the openings 50 due to the force of blood flow as depicted by directional arrows 78. Also shown is embolic debris 76, which had not been engaged by the proximal filter 24, but which is engaged in the distally located filter end 47 of the distal filter 26. The capture sleeve 14, which has been expandingly deployed in the blood vessel 74 as previously described, is shown immediately proximal to the proximal filter 24. Each of the distal and proximal filters 26 and 24 is shown having engaged and trapped smaller embolic debris 76 of one shape or another.

Figure 7:
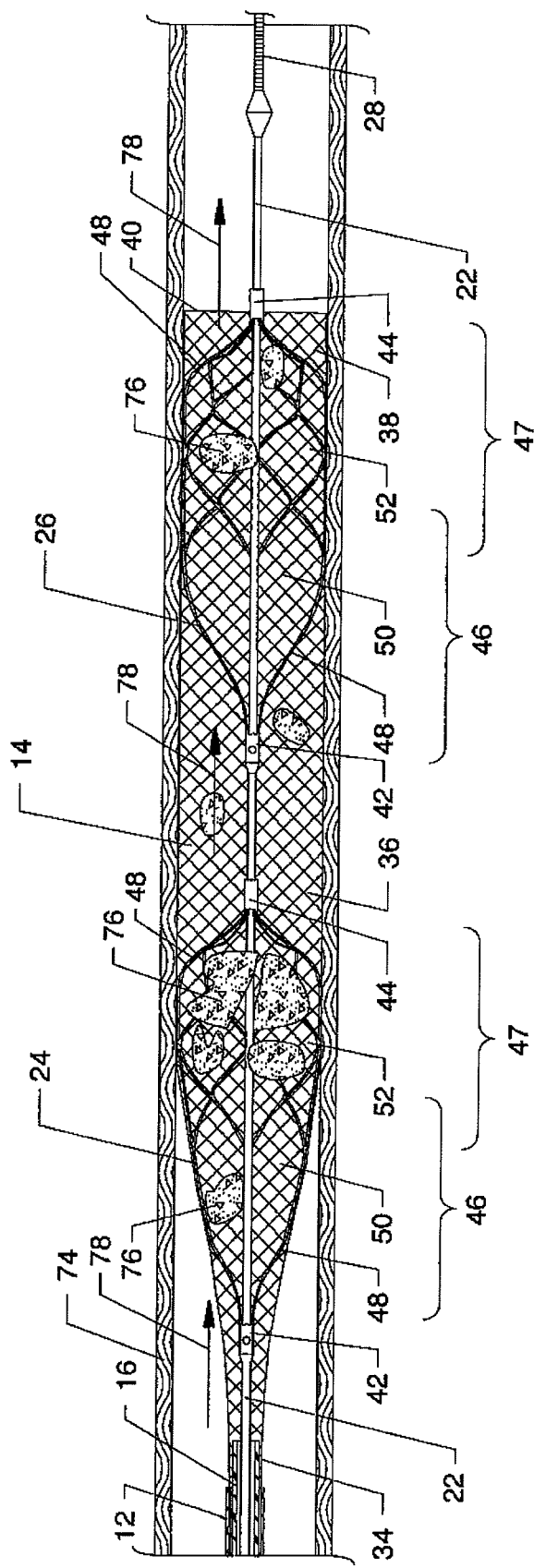
FIG. 7 is an illustration similar to FIG. 6 further showing the use of the capture sleeve in the capture mode in engagement over and about the proximal filter and the distal filter.

Engagement and entrapment of the embolic debris 76 can be accomplished either by the distal blood flow containing smaller pieces of embolic debris 76, as previously described, or by the manual forcible urging of the guidewire 22 and the connected proximal filter 24 and the distal filter 26 proximally to part, divide and macerate large pieces or collections of embolic debris 76 which are temporarily urged into and fixed in place in the capture sleeve 14 by contact caused by the proximal urging of the proximal filter 24. Some of the large pieces of embolic debris 76 can be parted, divided and macerated by forced contact with the strands 48 of the proximal filter 24 and can gain entry into the interior of the proximal filter 24 through the large openings 50 of the proximally located open end 46 during parting, dividing and macerating where entrapment is provided by the strands 48 at the small openings 52 in the distally located filter end 47, as shown in FIG. 7. Small particles of embolic debris 76 may pass directly through the large openings 50 for trapping by the strands 48 at the small openings 52 at the distally located filter end 47 of the proximal filter 24 without contacting the strands 48 of the large openings 50. To ensure more complete trapping and filtration, the embolic debris 76 which is not trapped by the proximal filter 24 can be trapped in the distal filter 26 in a similar manner just described. Preferably, blood flow as depicted by directed arrows 78 is monitored and entrapment of the embolic debris 76 within the proximal filter 24 and the distal filter 26 can be observed fluoroscopically or by other suitable methods in order to ensure blood flow through both the proximal filter 24 and the distal filter 26 during the filtering process.

FIG. 7 is an illustration similar to FIG. 6 further showing the use of the capture sleeve 14 in the capture mode by showing the engagement of the capture sleeve 14 over and about the proximal filter 24 and the distal filter 26, each of which has entrapped embolic debris 76 therein. Such engagement is accomplished by advancing the capture sleeve 14 distally toward and over the proximal filter 24 and the distal filter 26 by operation of the capture sleeve operator 20. The guidewire 22 can be cooperatively actuated proximally in order to intimately contact and pull and urge the large piece of embolic debris 76 into the capture sleeve 14 by impingement of the large piece of embolic debris 76 by the proximally directed proximal filter 24, through the flared distal section 38 and the annular edge 40 of the captive sleeve 14 and into the flared midsection 36, i.e., the confines of the capture sleeve 14. During such proximally directed urging of the large piece of embolic debris 76, the embolic debris 76 impinges upon the flared distal section 38 and the flared midsection 36 where the reduction of the flare of each capture sleeve section beneficially resists proximal movement of the impinging large piece of embolic debris 76. Such impingement and resistance to the movement temporarily fixes the position of the large piece of embolic debris 76, whereby the proximally urged strands 48 of the proximally directed proximal filter 24 forcibly part, divide and macerate the large piece of embolic debris 76 resulting in several smaller pieces, as shown, which can be subsequently trapped by the strands 48 of the small openings 52 of the distally located filter ends 47 or which can be forced through the strands 48 of the small openings 52 as smaller parted, divided and macerated pieces of embolic debris 76 which may then be trapped by the structure of the distal filter 26. Other smaller particles of embolic debris 76 can also be tilteringly trapped by the distal filter ends 47 of each of the proximal and distal filters 24 and 26. Very small particles of embolic debris 76 which pass through the located filter ends 47 of the proximal filter 24 and the distal filter 26 may be of insignificant consequence and can pass downstream.

Figure 8:
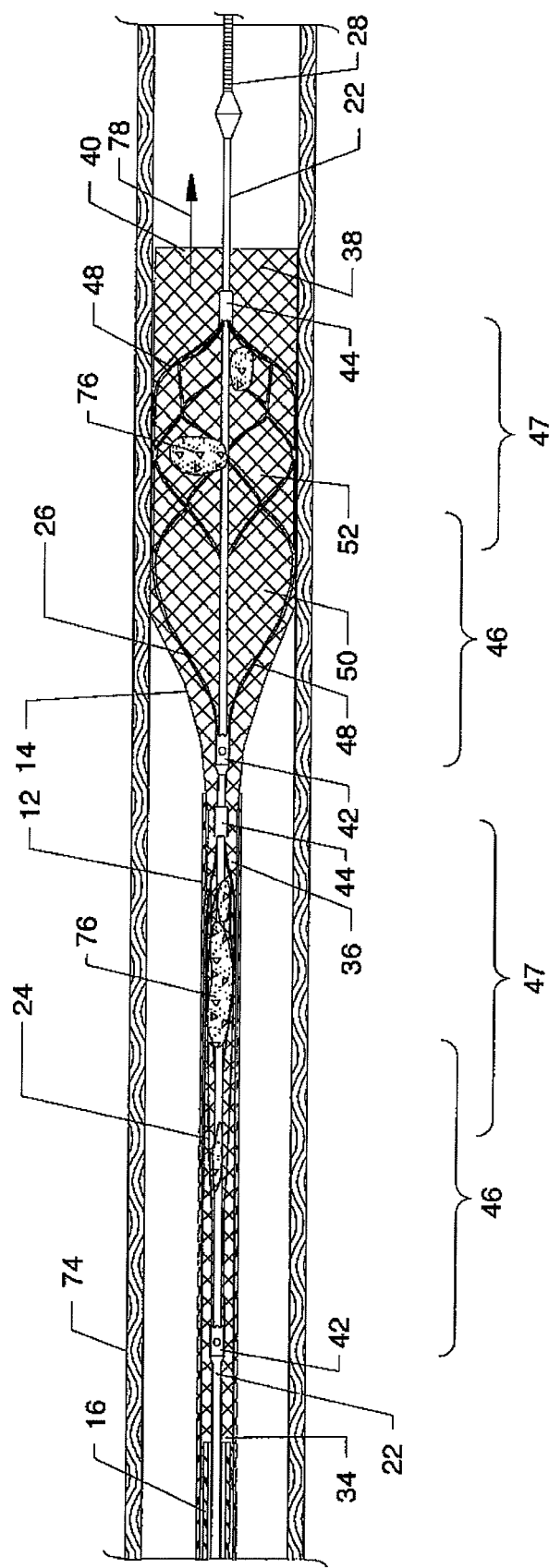
FIG. 8 is an illustration similar to FIG. 7 further showing the use of the capture sleeve and the capture/delivery sheath in the capture mode.

FIG. 8 is an illustration similar to FIG. 7 further showing the use of the capture sleeve 14 and the capture/delivery sheath 12 in the capture mode. Operation of the capture/delivery sheath operator 18 forces the capture/delivery sheath 12 distally, whereby the distal end of the capture/delivery sheath 12 is progressively positioned directly over and about the capture sleeve 14 and, simultaneously, is progressively and indirectly positioned over and about the proximal filter 24 which is coaxially aligned within the capture sleeve 14. Such distal progressive distal positioning of the capture/delivery sheath 12 forcibly compresses the capture sleeve 14, the underlying proximal filter 24 and the embolic debris 76 which has been captured within the proximal filter 24. During compression, the embolic debris 76 can also be elongated or may beneficially be further parted, divided and macerated into smaller pieces.

Figure 9:
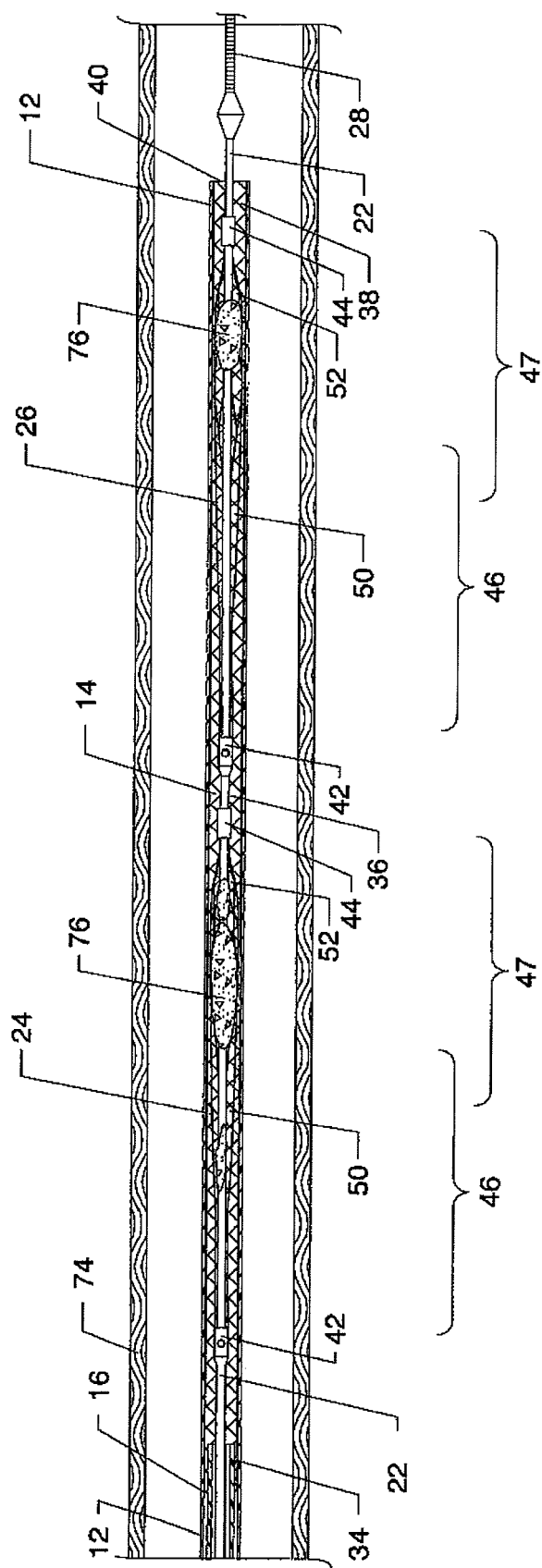
FIG. 9 is an illustration, similar to FIG. 8 further showing the use of the capture sleeve and the capture/delivery sheath in the capture mode.

FIG. 9 is an illustration similar to FIG. 8 further showing the use of the capture sleeve 14 and the capture/delivery sheath 12 in the capture mode. In this illustration, the capture/delivery sheath 12 is positioned further and fully in a distal direction to force complete compression of the capture sleeve 14 where the capture/delivery sheath 12 is in alignment directly over and about the distal portion of the capture sleeve 14 and simultaneously is indirectly and compressingly positioned over and about the distal filter 26 which is in coaxial alignment within the distal portion of the capture sleeve 14. Complete compression of the capture sleeve 14 indirectly over and about the proximal filter 24 and the embolic debris 76 captured therein and indirectly over and about the distal filter 26 and the embolic debris 76 captured therein and directly over and about the capture sleeve 14 provides a low profile structure of such components containing captured embolic debris 76. Components of such low profile structure containing captured embolic debris 76 may be readily withdrawn, preferably in simultaneous fashion, proximally through the capture/delivery sheath 12 where the capture sleeve positioning tube 16, the embolic debris laden capture sleeve 14, the guidewire 22 and the compressed embolic debris laden proximal filter 24 and distal filter 26 are withdrawn in a proximally directed removal from the capture/delivery sheath 12 by a proximal and manual directed unitary movement of the capture/delivery sheath operator 18, the capture sleeve operator 20 and attached capture sleeve positioning tube 16, and the guidewire 22. In the alternative, the capture sleeve positioning tube 16, the embolic debris laden capture sleeve 14, the guidewire 22 and proximal filter 24 and distal filter 26 and the capture/delivery sheath 12 may be entirely and unitarily withdrawn from the blood vessel 74 by the proximal and manual directed movement of the capture/delivery sheath operator 18, the capture sleeve operator 20 and the guidewire 22. Such removal is closely and generally related to or is the same for the later described alternative embodiments.

Figure 10:
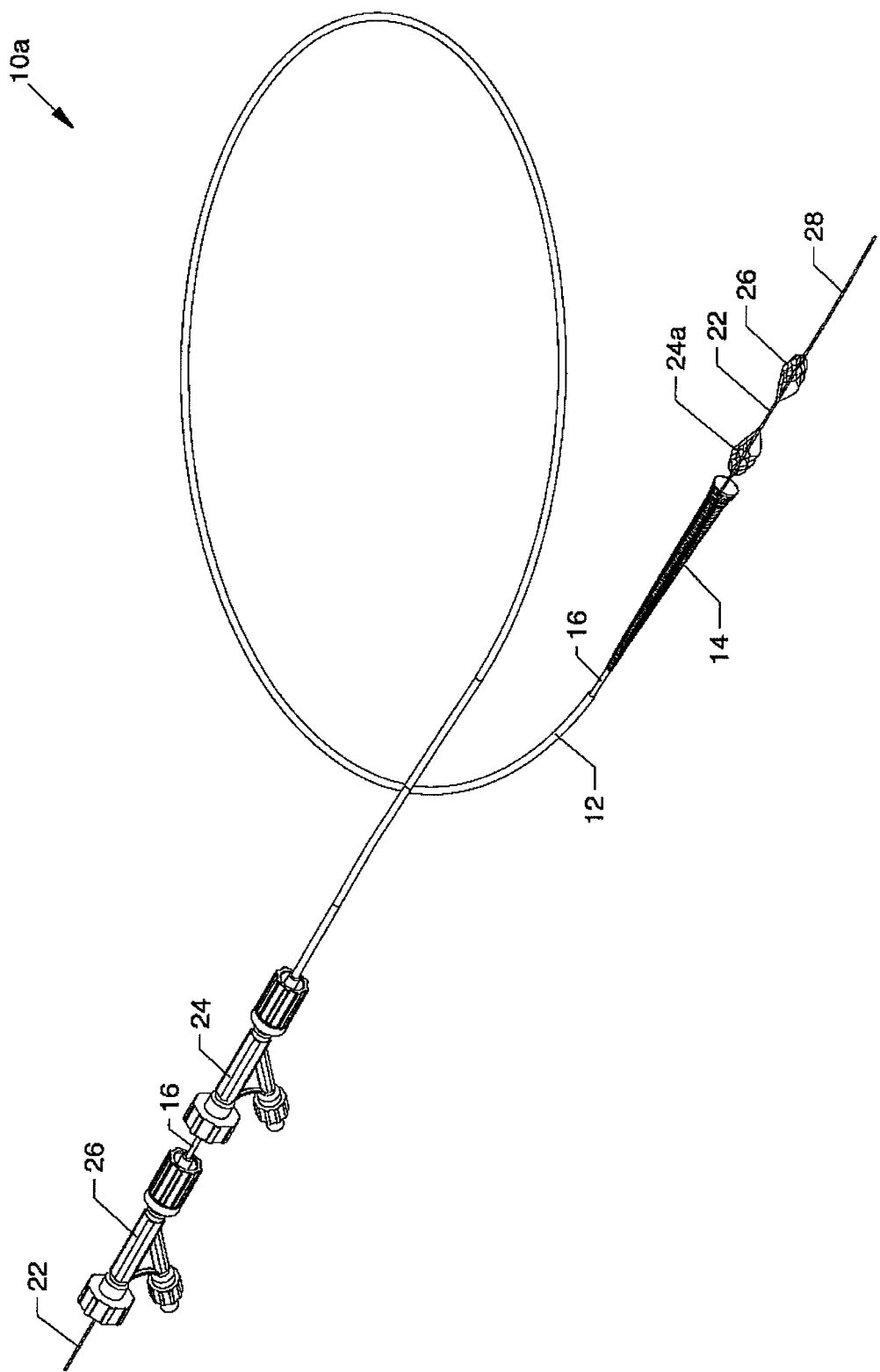
FIG. 10, a first alternative embodiment, is an isometric overview of the intravascular guidewire filter system for pulmonary embolism protection and embolism removal or maceration.

FIG. 10, a first alternative embodiment, is an isometric overview of the intravascular emboli capture and retrieval system for intravascular embolism protection and embolism removal or maceration, 10a. Generally, this alternative embodiment is useful in blood vessels of 8 mm or less to capture embolic debris although maceration of such debris is also associated therewith and is used in much the same manner as previously described for the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This first alternative embodiment is similar to the preferred embodiment of FIG. 1 with the exception of the arrangement, reorientation or modification of one or more filters and the use thereof. A flexible preformed memory shaped proximal filter 24a of this first alternative embodiment which can be deployed proximal to a large embolic debris 76 is used in lieu of the preformed memory shaped proximal filter 24 of the preferred embodiment and is located on the guidewire 22 and is generally of the same shape but with slightly modified features and is reversely oriented. Such reorientation provides for the use of a robust and close filter weave of the filter end 47 for proximally directed pulling of a large piece of organized embolic debris 76 or embolic debris collection by the proximal filter 24a. Also provided, in the alternative, is the ability to deploy the proximal filter 24a and the distal filter 26 such that the embolic debris 76 is located therebetween whereby the proximal filter 24a and the distal filter 26 could be alternately urged proximally and distally to cause an impingement of the strands 48 of the proximal filter 24a and the distal filter 26 with the embolic debris 76, as described later in detail.

Figure 11:
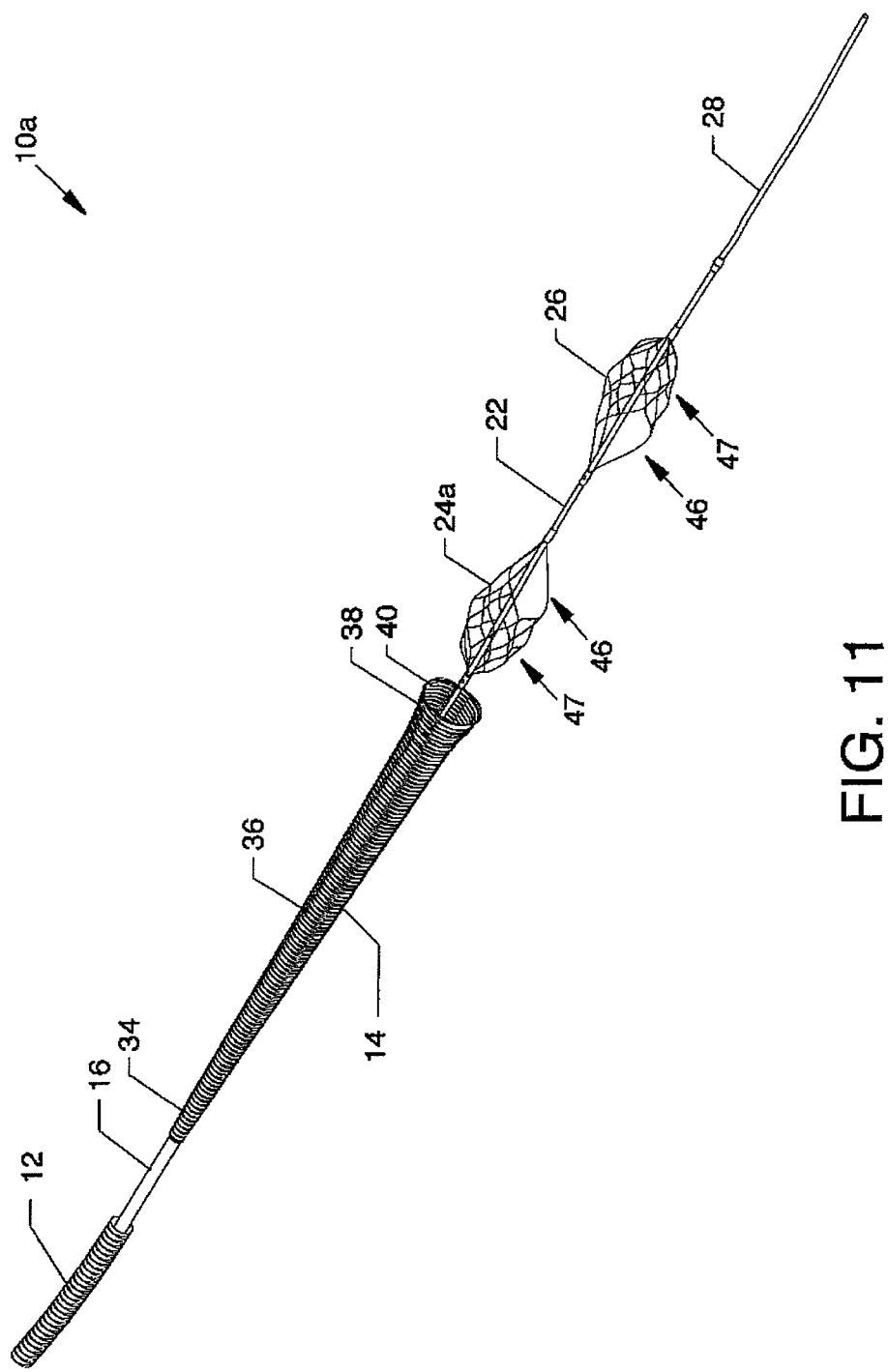
FIG. 11 is an illustration similar to FIG. 2 and is an isometric view of the components located at the distal region of a first alternative embodiment.

FIG. 11 is an illustration similar to FIG. 2 and is an isometric view of the components located at the distal region of the first alternative embodiment of the present disclosure. Shown, in particular, is the relationship of the proximal filter 24a to the capture sleeve 14 and to the distal filter 26.

Figure 12:
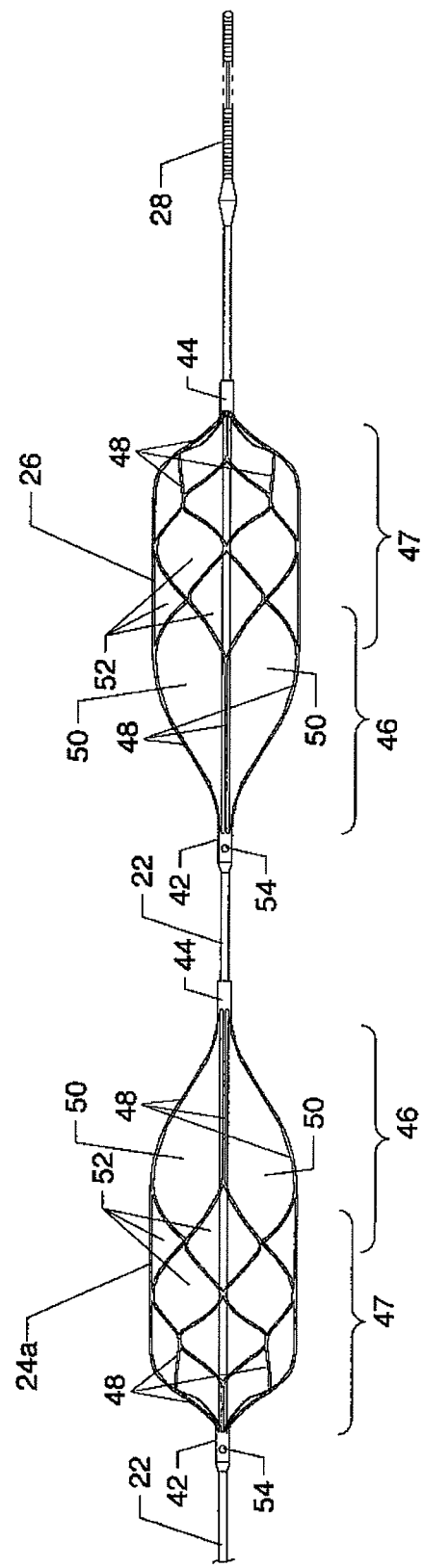
FIG. 12 is an illustration similar to FIG. 4 and is a side view of the distal end of a guidewire including a preformed memory shaped proximal filter and a preformed memory shaped distal filter.

FIG. 12 is an illustration similar to FIG. 4 and is a side view of the distal end of the guidewire 22 including the preformed memory shaped proximal filter 24a and the preformed memory shaped distal filter 26. The structure of the proximal filter 24a is similar to but differs slightly from the proximal filter 24 and the distal filter 26 of the preferred embodiment. More specifically, features of the proximal filter 24 including the strands 48, the large openings 50 and the small openings 52, are reoriented and reversed in order to form the proximal filter 24a which is located between the proximal tube 42 and the distal tube 44, as shown, whereby the open end 46 and the filter end 47 are also reoriented and reversed. The location of the proximal tube 42 and the distal tube 44 is unchanged. The distal tube 44 is aligned over and about the guidewire 22 and is in sliding engagement with the guidewire 22. The use of the fixed proximal tube 42 and the slideable distal tube 44 enables the proximal filter 24a and distal filter 26 to be flexibly and expandingly deployed and to be flexibly, compressingly and elongatingly collapsed along and about their longitudinal axis and along the guidewire 22, whereby a lower filter profile is provided.

Mode of Operation

The mode of operation of the first alternative embodiment of the intravascular guidewire filter system 10a for the filtering and removal of various sized pieces of organized embolic debris is now described with reference to FIGS. 13-15, as well as understood reference to previously described figures. The capture sleeve operator 20 and the capture/delivery sheath operator 18, used singly or together, are operated to position the capture sleeve 14 and the capture/delivery sheath 12, respectively, in cooperating operation including the movement or nonmovement of the guidewire 22 and the attached proximal filter 24a and distal filter 26 as required during various delivery and capture phases, such as previously described with reference to the preferred embodiment.

Engagement and entrapment of smaller pieces of the embolic debris 76 in the distal filter 26 can be accomplished by the distal blood flow containing smaller pieces of embolic debris 76, as previously described. Engagement and entrapment of large embolic debris 76 can be accomplished by the judicious placement of the proximal filter 24a and the distal filter 26 with respect to the large embolic debris 76. In a first scenario and with respect to the large embolic debris 76, the guidewire 22 is deployed to position the proximal filter 24a distal to a large piece of embolic debris 76, and in a second scenario, the guidewire 22 is deployed to position the proximal filter 24a proximal to the large embolic debris 76 and the distal filter 26 is deployed distal to the large embolic debris 76 and used as described herein.

Figure 13:
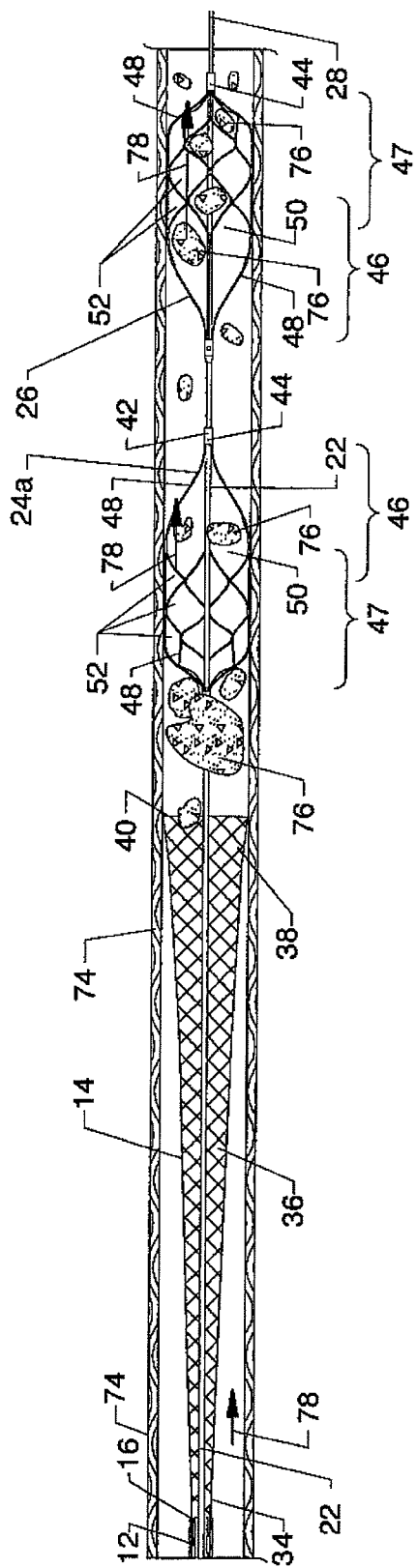
FIG. 13 is a cutaway view in partial cross section and partial cutaway view in the capture mode of the first alternative embodiment showing the proximal filter (in cutaway view), the distal filter and the guidewire deployed and aligned within a blood vessel.

In the first scenario, such as shown in FIG. 13 and with respect to the first alternative embodiment, a cutaway view is shown in partial cross section and partial cutaway view in the capture mode showing the proximal filter 24a (in cutaway view), the distal filter 26 and the guidewire 22 deployed and aligned within a blood vessel 74 showing a large piece of embolic debris 76 located proximal to the proximal filter 24a prior to initial engagement of the proximal and distal filters 24a and 26 by the flared distal section 38 of the capture sleeve 14. The capture sleeve 14 which has been expandingly deployed in the blood vessel 74, as previously described in the preferred embodiment, is shown immediately proximal to the proximal filter 24a. Manual positioning of the guidewire 22 in a proximal direction causes the deployed filter end 47 of the proximal filter 24a to engage and urge the large piece of embolic debris 76 proximally into the flared distal section 38 of the capture sleeve 14, the latter of which may be urged distally to cooperatively accommodate the large piece of embolic debris 76. The large piece of embolic debris 76 does not contact the strands 48 of the large openings 52 for parting, dividing and macerating, but instead encounters the relatively fine weave of the strands 48 at the filter end 47 located on the proximal filter 24a which filter end 47 wholly engages the large piece of embolic debris 76 with minimum, if any, parting, dividing or macerating. Also shown in the illustration is an embolic debris 76 of smaller size which had not been engaged by the proximal filter 24a, but which is engaged in the distally located filter end 47 of the distal filter 26. Each of the distal and proximal filters 26 and 24a is shown having engaged and trapped smaller embolic debris 76 of one shape or another.

Figure 14:
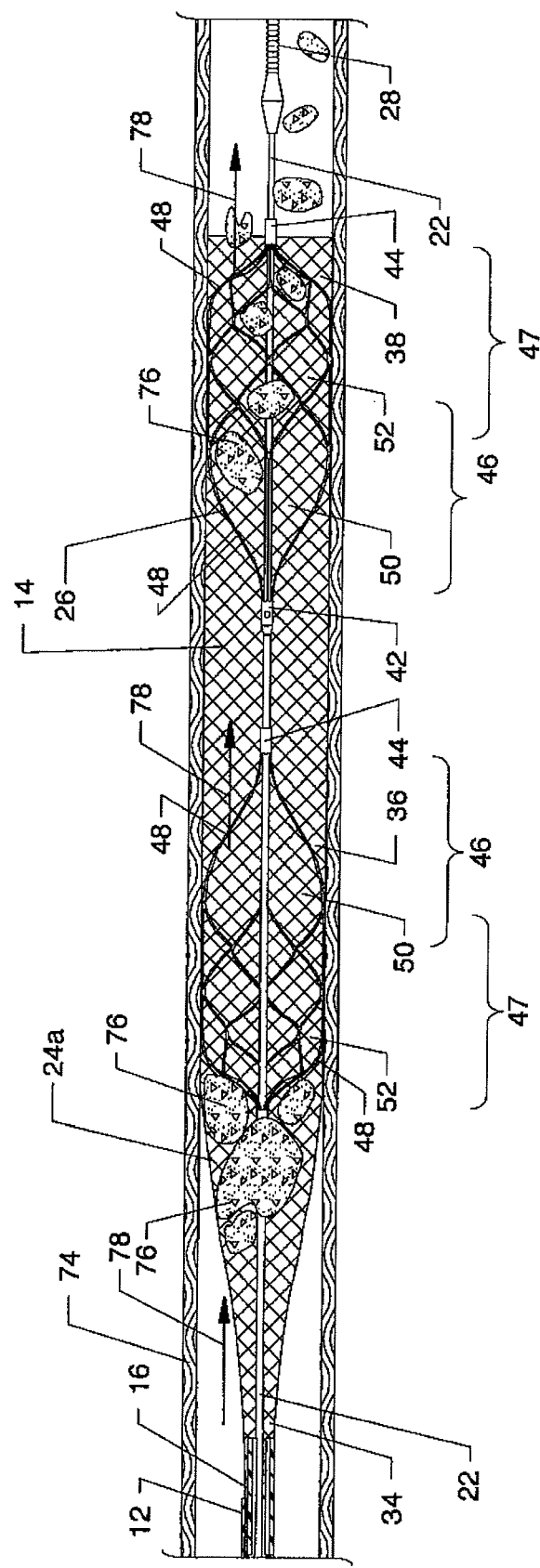
FIG. 14 is an illustration similar to FIG. 13 further showing the capture mode and demonstrating the engagement of the capture sleeve over and about the proximal filter, the distal filter, and large pieces of embolic debris.

FIG. 14 is an illustration similar to FIG. 13 further showing the capture mode and demonstrating the engagement of the capture sleeve 14 over and about the proximal filter 24a and the distal filter 26 and of a large piece of embolic debris 76, the latter of which has been urged into the interior of the capture sleeve 14. Operation of the capture sleeve operator 20 and the capture/delivery sheath operator 18 is used to position the capture sleeve 14 and the capture/delivery sheath 12, respectively, in concert with the movement of the guidewire 22 and the attached proximal filter 24a and distal filter 26 during various delivery and capture phases, such as previously described with reference to the preferred embodiment.

Figure 15:
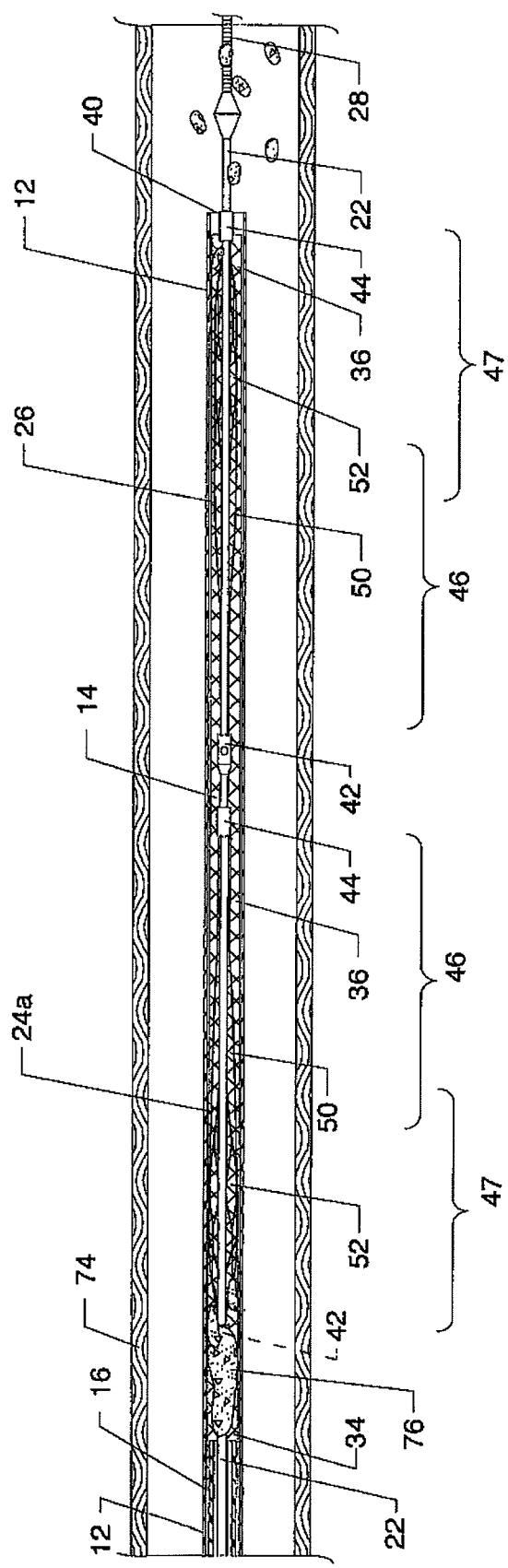
FIG. 15 is an illustration further showing and demonstrating the use of the capture sleeve and the capture/delivery sheath in the capture mode.

FIG. 15 is an illustration showing and demonstrating the use of the capture sleeve 14 and the capture/delivery sheath 12 in the capture mode. More specifically, collapsing of the proximal filter 24a and the distal filter 26 is assisted by engagement of the capture sleeve 14, the capture/delivery sheath 12, or both, in a manner as previously described in detail. In this illustration, the capture/delivery sheath 12 is positioned directly over and about the capture sleeve 14 in order to provide complete compression of the capture sleeve 14 and indirectly and compressingly over and about the proximal filter 24a and the embolic debris 76 captured therein and indirectly and compressingly over and about the distal filter 26 and any embolic debris 76 captured therein to enable a low profile structure of such components containing captured large or small embolic debris 76. Such a low profile structure of such components containing captured embolic debris 76 may be readily withdrawn, preferably in a manner and fashion as previously described with respect to the preferred embodiment.

Figure 16:
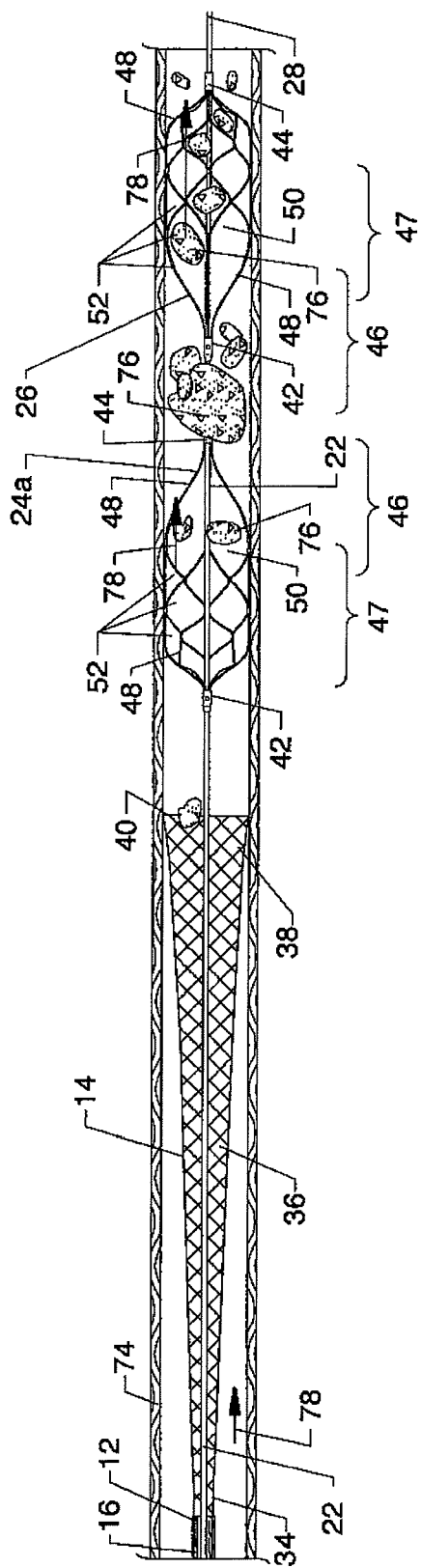
FIG. 16 shows the guidewire deployed to position an expanded proximal filter proximal to a large embolic debris with an expanded distal filter deployed and positioned distal to the large embolic debris.

In the second scenario, such as shown in FIG. 16, the guidewire 22 is deployed to expandingly position the proximal filter 24a proximal to the large embolic debris 76 and the distal filter 26 is deployed and expandingly positioned distal to the large embolic debris 76. The guidewire 22 is alternately positioned distally and proximally to cause the proximal filter 24a and the distal filter 26 to impinge opposing ends of the large embolic debris 76, whereupon urging of the guidewire 22 distally causes the engagement of the strands 48 at the open end 46 of the proximal filter 24a with the large embolic debris 76 which is parted, divided and macerated and which debris enters the large openings 50 for capture in the filter end 47 formed by the strands 48, and whereupon urging of the guidewire 22 proximally causes engagement of the strands 48 at the open end 46 of the distal filter 26 with the large embolic debris 76 which is parted, divided and macerated and which enters the large openings 50 for capture in the filter end 47 formed by the strands 48.

Figure 17:
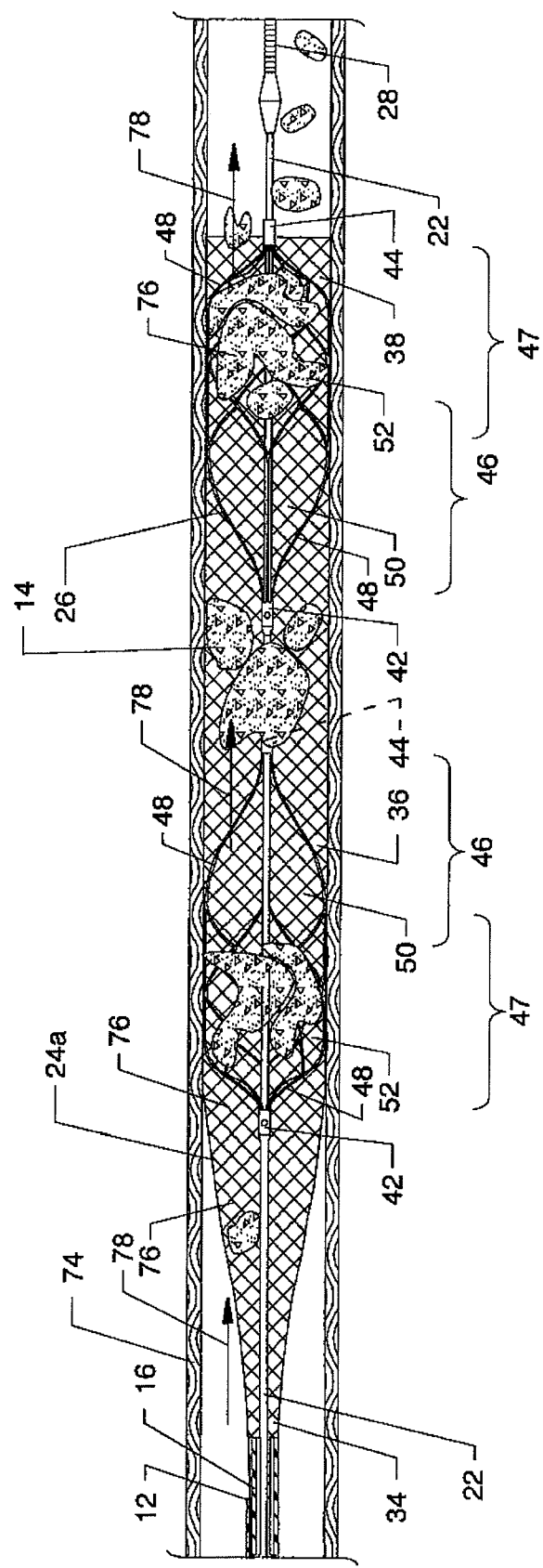
FIG. 17 is similar to FIG. 14 further showing the capture mode and demonstrating the engagement of the capture sleeve over and about the proximal filter and the distal filter and parts of one or more pieces of the large piece of embolic debris.

FIG. 17 is similar to FIG. 14 further showing the capture mode and demonstrating engagement of the capture sleeve 14 over and about the proximal filter 24a and the distal filter 26 and of parts of one or more pieces of the large embolic debris 76, the latter of which has been parted, divided and macerated and deposited into either or both proximal filter 24a and distal filter 26, such as described with reference to FIG. 16, and which await withdrawal of a low profile configuration wherein the capture/delivery sheath 12 and other components are utilized for compression and withdrawal of the capture sleeve 14, the proximal filter 24b, the distal filter 26 and the embolic debris 76 associated therewith in a manner as previously described and shown in FIG. 15.

Figure 18:
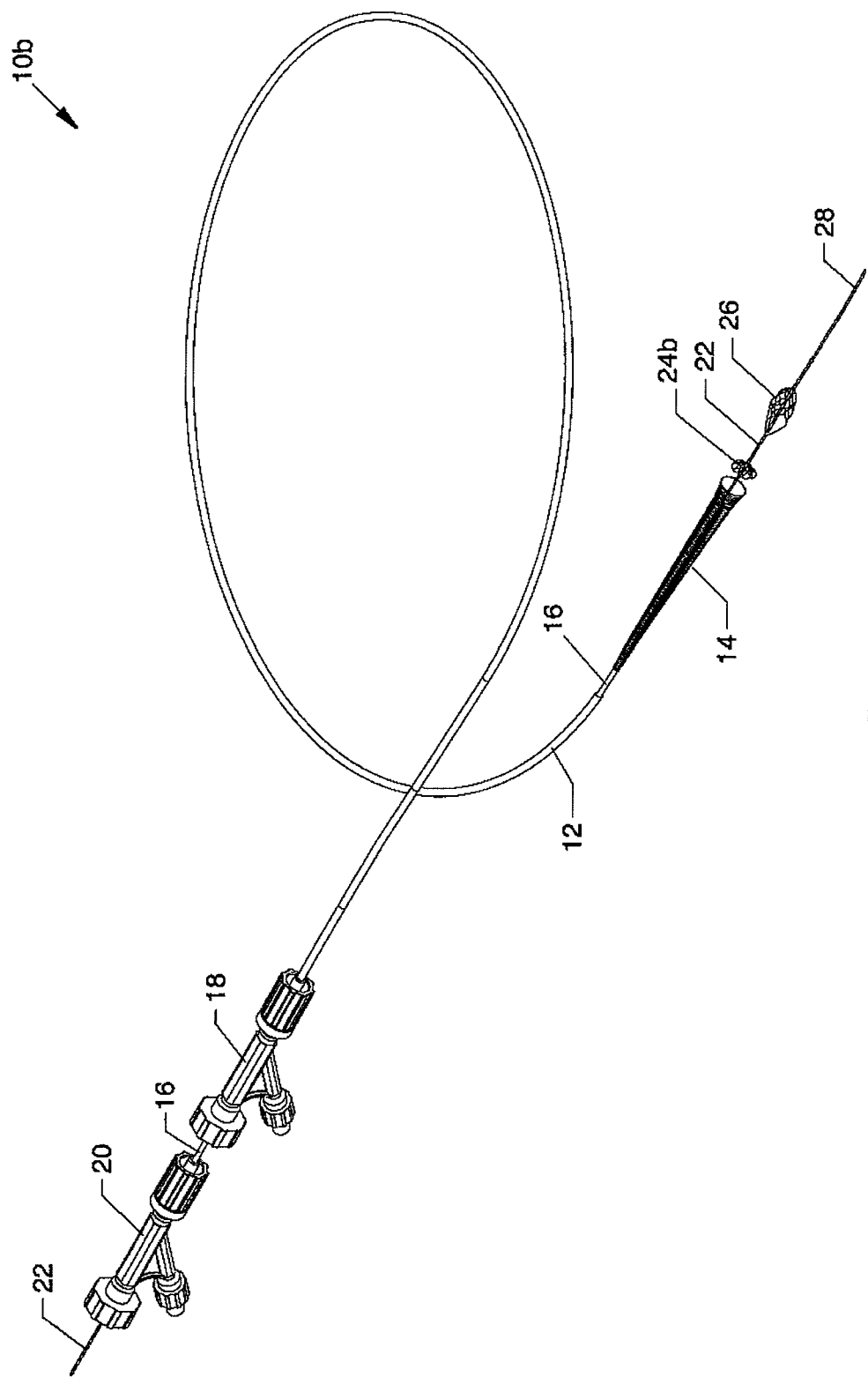
FIG. 18, a second alternative embodiment, is an isometric overview of the intravascular emboli capture, and retrieval system for intravascular embolism protection and embolism removal or maceration.

FIG. 18, a second alternative embodiment, is an isometric overview of the intravascular emboli capture and retrieval system for intravascular embolism protection and embolism removal or maceration, 10b. Generally, this alternative embodiment is useful in blood vessels of 8 mm or less to capture embolic debris, although maceration of such is also associated therewith and is used much in the same manner as described for use in the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This second alternative embodiment is similar to the preferred embodiment of FIG. 1 with the exception of the arrangement, reorientation or modification of one or more filters and use thereof. A flexible preformed memory shaped proximal filter 24b of this second alternative embodiment, which can be deployed distal to a large embolic debris 76, is used in lieu of the preformed memory shaped proximal filter 24 of the preferred embodiment and is located on the guidewire 22 and, in general, is of an alternate shape and configuration. The concave basket-like flexible preformed memory shaped proximal filter 24b is open in a proximal facing direction to present its concave shaped side to the blood flow and to a proximally located large piece of embolic debris 76. The proximal filter 24b provides a robust and suitable filter weave for pulling a large piece of organized embolic debris 76 or embolic debris collection in a proximal direction.

Figure 19:
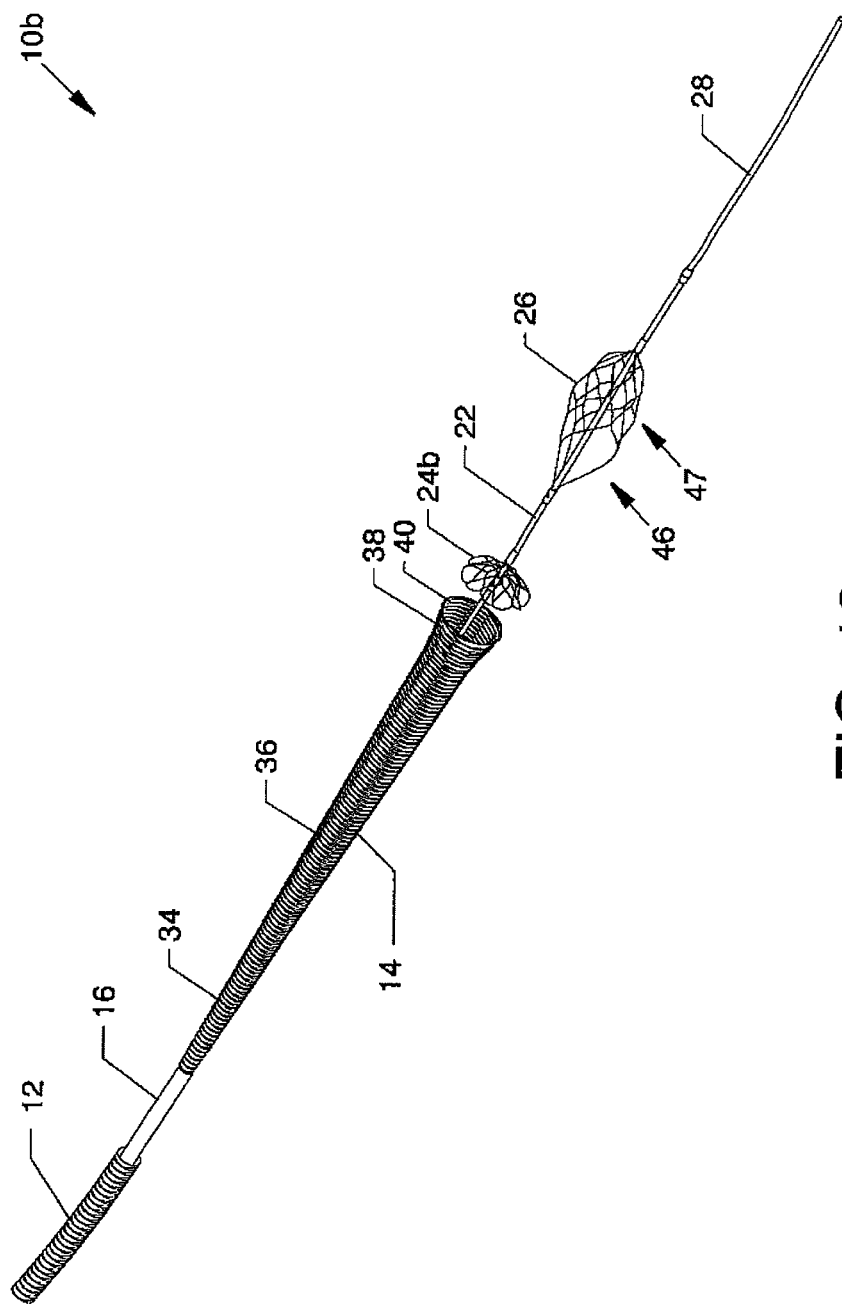
FIG. 19 is an illustration similar to FIG. 2 and is an isometric view of the guidewire filter components located at the distal region of a second alternative embodiment.

FIG. 19 is an illustration similar to FIG. 2 and is an isometric view of the components located at the distal region of this second alternative embodiment of the present disclosure. Shown in particular is the relationship of the proximal filter 24b to the capture sleeve 14 and to the distal filter 26.

Figure 20:
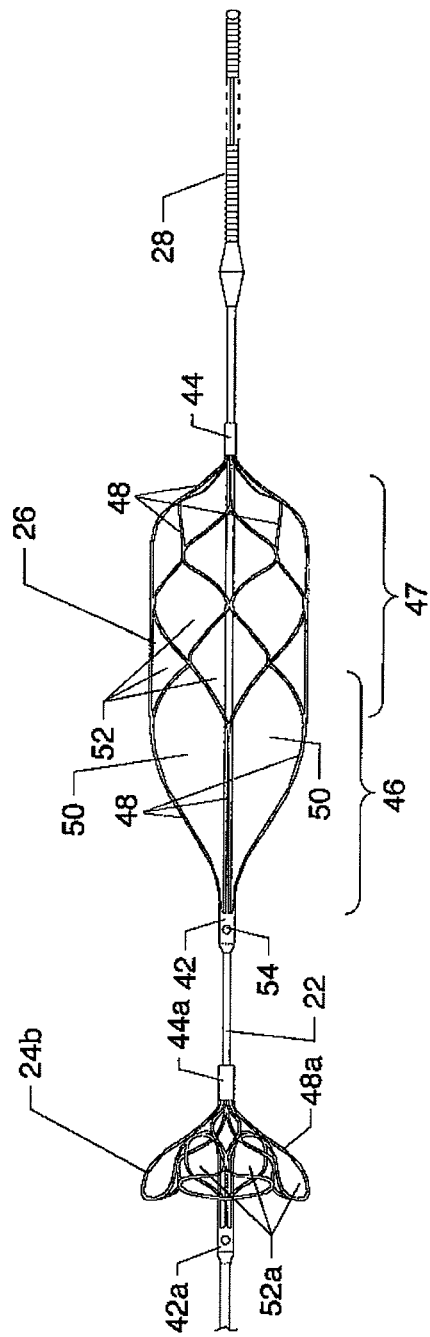
FIG. 20 is a full view illustration corresponding to FIG. 4 and is a side view of the distal end of the guidewire including the preformed memory shaped proximal filter and the preformed memory shaped distal filter.

FIG. 20 is a full view illustration corresponding to FIG. 4 and is a side view of the distal end of the guidewire 22 including the preformed memory shaped proximal filter 24b and the preformed memory shaped distal filter 26. The structure of the proximal filter 24b is related to that of the distal filter 26 but does not include large openings 50. Features of the proximal filter 24b include strands 48a which form small openings 52a corresponding for the most part to the small openings 52 of the distal filter 26 which openings are arranged and located between the proximal tube 42a and the distal tube 44a. The proximal tube 42a secures over and about the guidewire 22 in the same fashion as prescribed for the attachment of the proximal tube 42 of the preferred embodiment. The distal tube 44a is aligned over and about the guidewire 22 and is slidingly engaged therewith. The use of the fixed proximal tube 42a and the slideable distal tube 44a enables the proximal filter 24b to be flexibly and expandingly deployed and to be flexibly, compressingly, reversibly and elongatingly collapsed along and about the guidewire 22 whereby a lower filter profile is provided in order to facilitate removal.

Mode of Operation

The mode of operation of this second alternative embodiment of the intravascular guidewire filter system 10b for the filtering and removal of various sized pieces of organized embolic debris is now described with reference to FIGS. 21-25, as well as understood reference to previously described figures. Operation of the capture sleeve operator 20 and the capture/delivery sheath operator 18, used singly or together, are operated to position the capture sleeve 14 and the capture/delivery sheath 12, respectively, in cooperating operation including the movement or nonmovement of the guidewire 22 and the attached proximal filter 24b and distal filter 26 as required during various delivery and capture phases, such as previously described with reference to the preferred embodiment.

Engagement and entrapment of smaller pieces of the embolic debris 76 in the distal filter 26 can be accomplished by the distal blood flow containing smaller pieces of embolic debris 76, as previously described. Engagement and entrapment of large embolic debris 76 can be accomplished by the judicious placement of the proximal filter 24b and the distal filter 26 with respect to the large embolic debris 76. With respect to the large embolic debris 76, the guidewire 22 is deployed to position the proximal filter 24b distal to a large piece of embolic debris 76, as shown in FIG. 21 and used as described herein.

Figure 21:
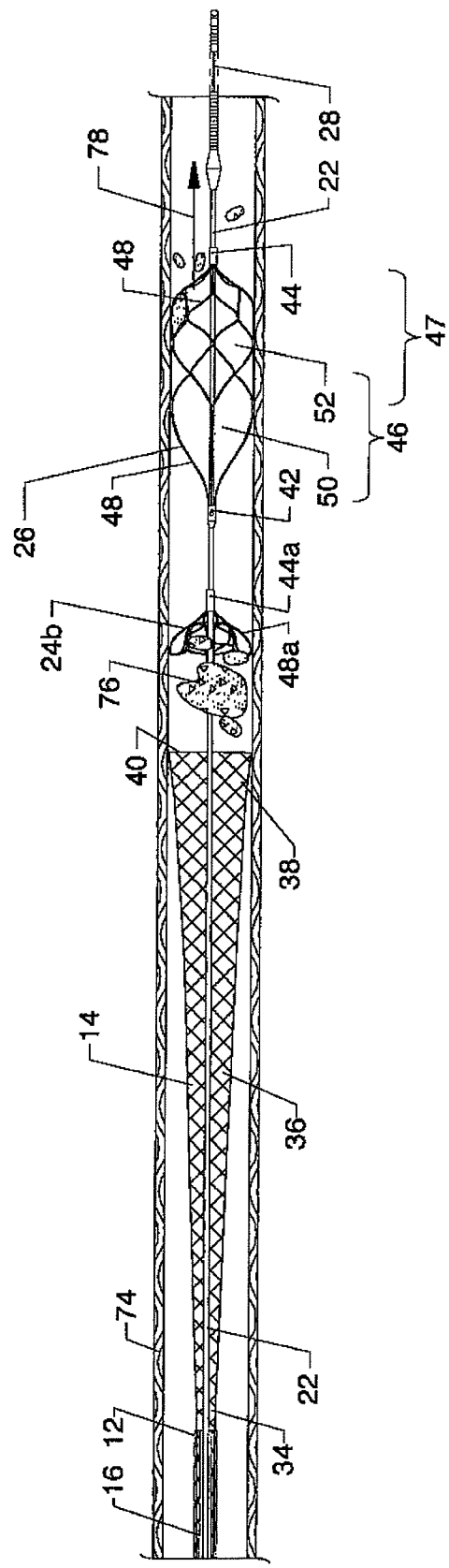
FIG. 21 is a cutaway view shown in partial cross section and partial cutaway view in the capture mode of the second alternative embodiment showing the proximal filter (in cutaway view), the distal filter and the guidewire deployed and aligned within a blood vessel.

As shown in FIG. 21 and with respect to this second alternative embodiment, a cutaway view is shown in partial cross section and partial cutaway view in the capture mode showing the proximal filter 24b (in cutaway view), the distal filter 26 and the guidewire 22 deployed and aligned within a blood vessel 74 showing a large piece of embolic debris 76 located proximal to the proximal filter 24b prior to an initial engagement of the filters by the flared distal section 38 of the capture sleeve 14. The capture sleeve 14 which has been expandingly deployed in the blood vessel 74, as previously described in the preferred embodiment, is shown immediately proximal to the proximal filter 24b and a short distance from the distal filter 26. Manual positioning of the guidewire 22 in a proximal direction causes the deployed proximal filter 24b to engage and urge the large piece of embolic debris 76 proximally to enter into the flared distal section 38 of the capture sleeve 14, the latter of which may be urged distally to cooperatingly accommodate the large piece of embolic debris 76. The large piece of embolic debris 76 encounters the filtering weave of the strands 48a located in the proximal filter 24b which weave initially and wholly engages the large piece of embolic debris 76 with minimum, if any, parting, dividing or macerating thereof. Also shown in the illustration is embolic debris 76 of smaller size which had not been engaged by the proximal filter 24b but which is engaged in the distally located filter end 47 of the distal filter 26.

Figure 22:
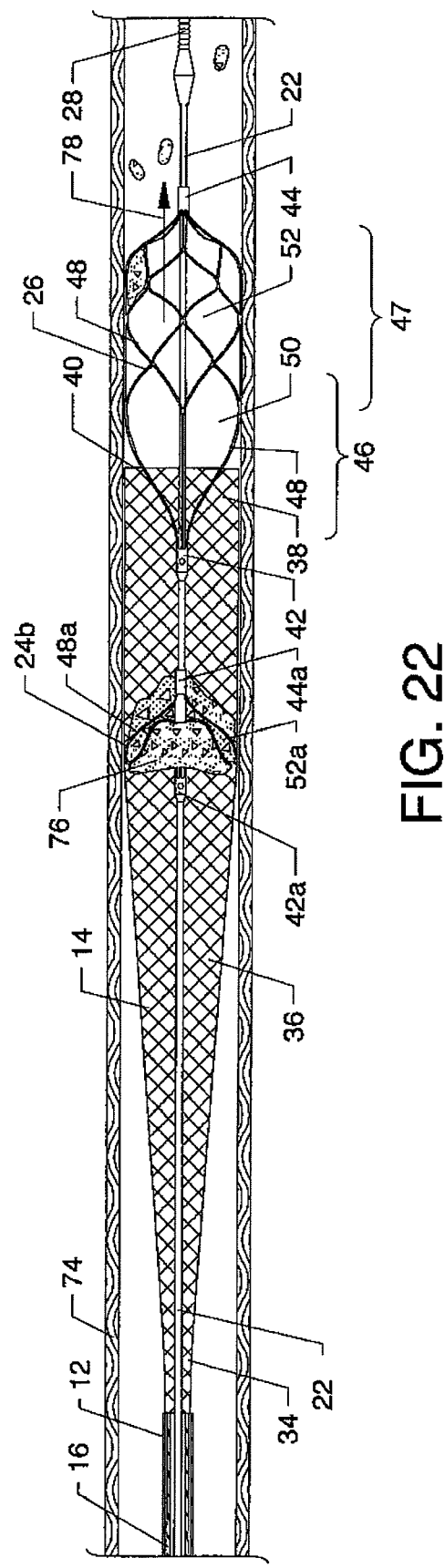
FIG. 22 is an illustration similar to FIG. 21 further showing the capture mode and demonstrating the engagement of the uncompressed capture sleeve over and about the proximal filter, over and about the proximal end of the distal filter, and over and about a large piece of embolic debris.

FIG. 22 is an illustration similar to FIG. 21 further showing the capture mode and demonstrating the engagement of the uncompressed capture sleeve 14 over and about the proximal filter 24b, over and about the proximal end of the distal filter 26 and over and about the large piece of embolic debris 76, the latter of which has been urged into the interior of the capture sleeve 14 and engaged therein by action of the proximally directed guidewire 22 and proximal filter 24b. Such engagement may be assistingly accomplished by advancing the capture sleeve 14 distally toward and over the proximal filter 24b and the distal filter 26 by operation of the capture sleeve operator 20 in order to position the flared distal section 38 and the annular edge 40 of the captive sleeve 14 in close proximity to the proximal filter 24b and the large piece of embolic debris 76, as shown in FIG. 21. The guidewire 22 is then actuated proximally in order to intimately contact, pull and urge the large piece of embolic debris 76 into the capture sleeve 14 as shown by the impingement of the large piece of embolic debris 76 by the proximally directed proximal filter 24b through the flared distal section 38 and the annular edge 40 of the capture sleeve 14 and into the flared midsection 36, i.e., the confines of the capture sleeve 14. During such proximally directed urging of the large piece of embolic debris 76, it can progressively impinge upon the flared distal section 38 and the flared midsection 36 of the capture sleeve 14 where the reduction of the flare of each section beneficially resists proximal movement of the impinging large piece of embolic debris 76. Such impingement and resistance to movement temporarily and wedgingly fixes the position of the large piece of embolic debris 76, whereby the proximally urged strands 48a of the proximally directed proximal filter 24b can then forcibly part, divide and macerate the large piece of embolic debris 76, as now shown in FIG. 22, resulting in several smaller pieces as shown in FIG. 23.

Figure 23:
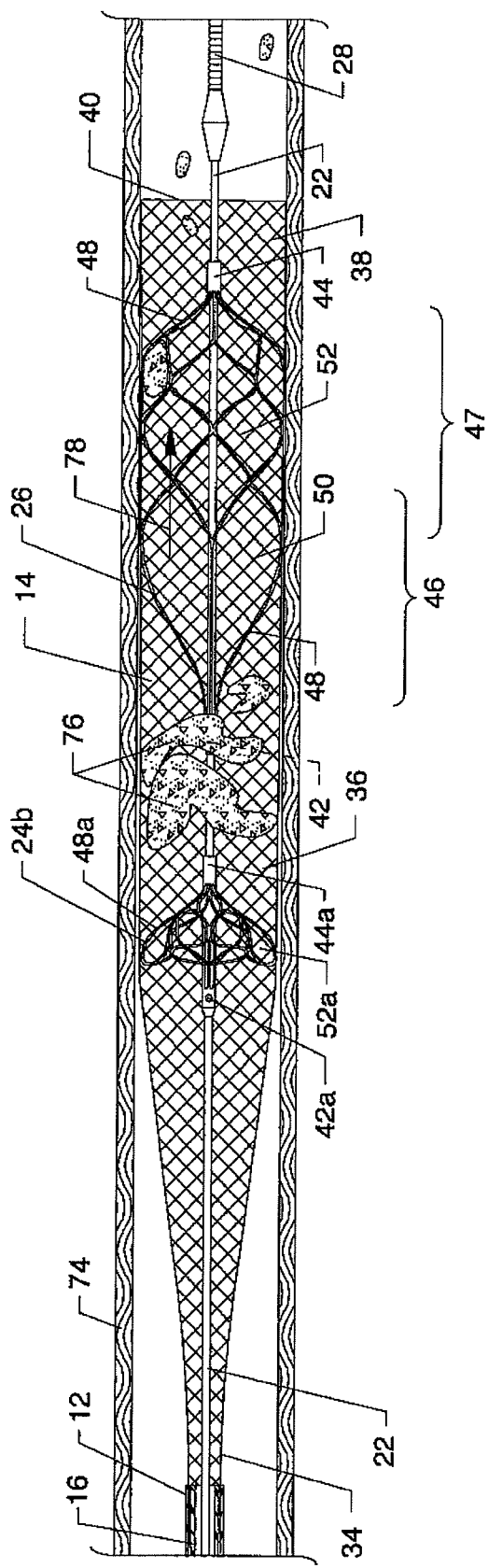
FIG. 23 is an illustration similar to FIG. 22 further showing the capture mode and demonstrating the full engagement of the uncompressed capture sleeve over and about the proximal filter, the distal filter and pieces of the large piece of embolic debris.
Figure 24:
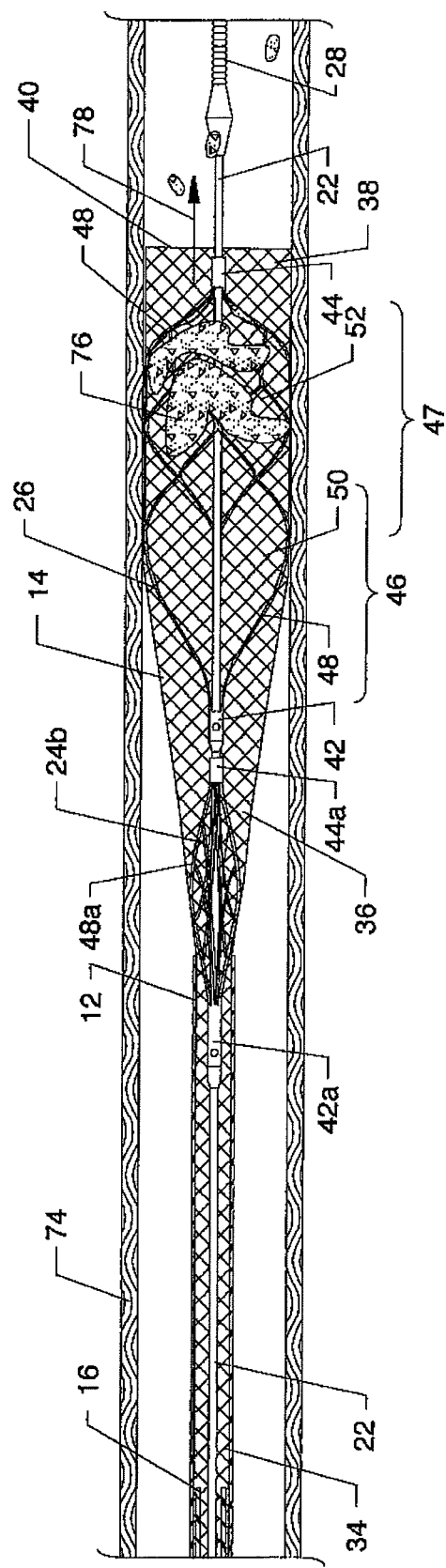
FIG. 24 is an illustration similar to FIG. 23 but where the distal filter is shown in cross section view further showing the capture mode and demonstrating the distal positioning of the capture/delivery sheath over and about capture sleeve.

FIG. 23 is an illustration similar to FIG. 22 further showing the capture mode and demonstrating full engagement of the uncompressed capture sleeve 14 over and about the proximal filter 24b, the distal filter 26 and pieces of the large piece of embolic debris 76, the latter of which have been forcibly parted, divided and macerated by passage through the strands 48a of the proximal filter 24b and subsequently contained in the interior of the capture sleeve 14. These smaller pieces of embolic debris 76 can be urged distally by blood flow or by proximal movement of the distal filter 26 to impinge upon or be impinged by the strands 48 of the large openings 50 to enter the large openings 50 of the distal filter 26. Subsequent trapping of such processed embolic debris 76 is provided by the strands 48 comprising the small openings 52 at the distally located filter end 47 of the distal filter 26, as shown in FIG. 24. Very small particles of embolic debris 76, which pass through the distally located filter end 47 of the distal filter 26, may be of insignificant consequence and can pass downstream.

FIG. 24 is an illustration similar to FIG. 23, but where the distal filter 26 is shown in cross section view further showing the capture mode and demonstrating the distal positioning of the capture/delivery sheath 12 further over and about the capture sleeve 14 in order to compress the flared midsection 36 of the capture sleeve 14 and to compress the underlying coaxially aligned proximal filter 24b. The positioning of the distal end of the capture/delivery sheath 12 over and about the proximal tube 42a and the proximal portion of the strands 48a causes the concave feature of the proximal filter 24a to reformingly elongate. The parted, divided and macerated embolic debris 76 is shown entrapped within the filter end 47 of the distal filter 26.

Figure 25:
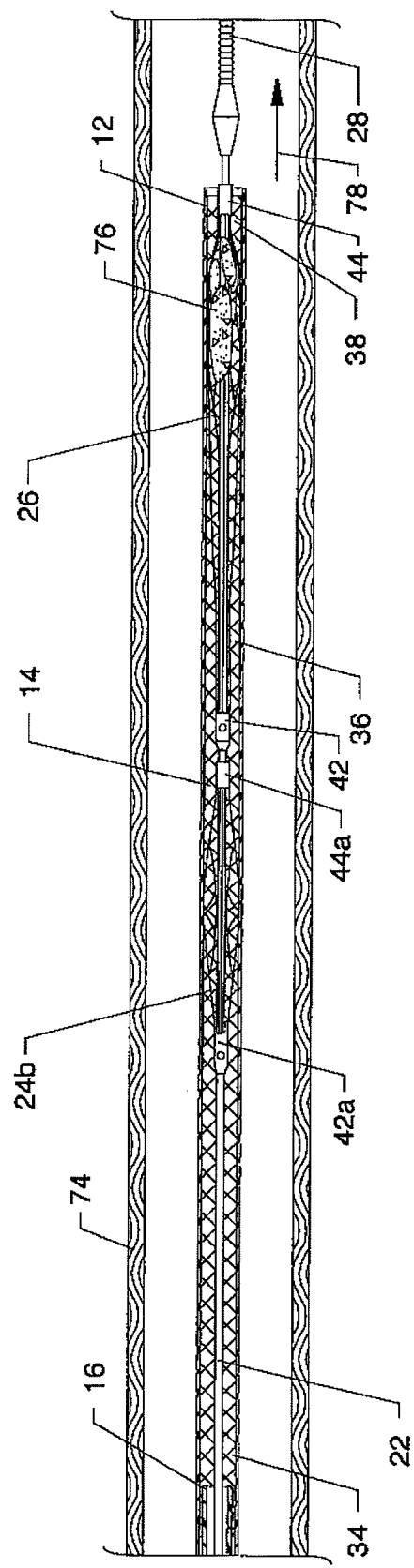
FIG. 25 is an illustration of the second alternative embodiment showing and demonstrating the use of the capture/delivery sheath in the full capture mode.

FIG. 25 is an illustration showing and demonstrating the use of the capture/delivery sheath 12 in a full capture mode. More specifically, collapsing of the proximal filter 24b and distal filter 26 is assisted by the full compressed engagement of the capture sleeve 14, full compressed engagement of the capture/delivery sheath 12, or both, in a manner as previously described in detail. In this illustration, the capture/delivery sheath 12 is directly and compressingly positioned over and about the entire capture sleeve 14 in order to provide complete compression thereof. Furthermore, the capture/delivery sheath 12 is indirectly and compressingly positioned over and about the coaxially aligned proximal filter 24b and any embolic debris 76 captured therein, indirectly and is compressingly positioned over and about the distal filter 26 and any embolic debris 76 captured therein in order to provide a compressed low profile structure of such components containing captured large or small embolic debris 76. Such a low profile structure of such components containing captured embolic debris 76 may be readily withdrawn, preferably in a manner and fashion as previously described with respect to the preferred embodiment.

Figure 26:
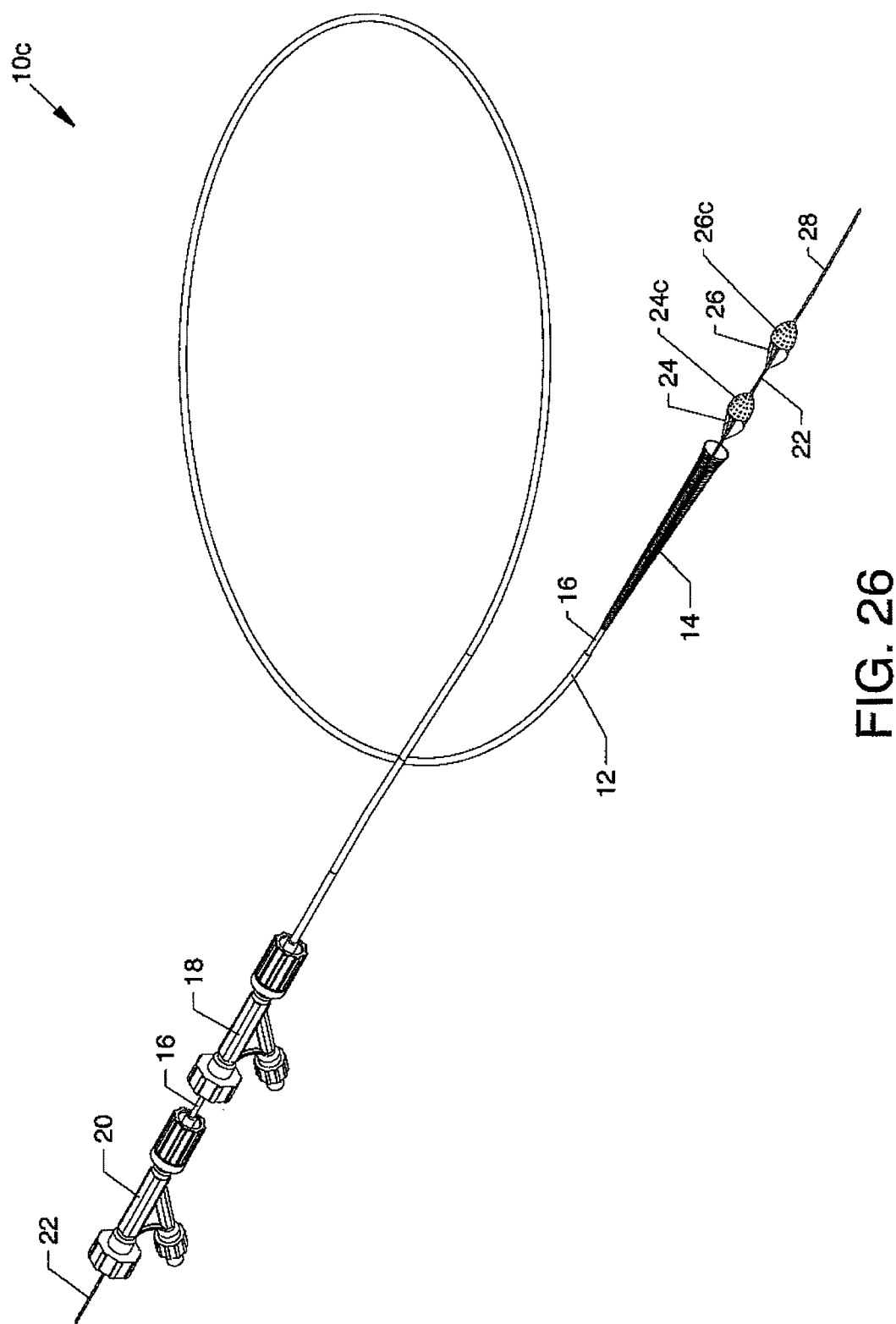
FIG. 26, a third alternative embodiment, is an isometric overview of the intravascular emboli capture and retrieval system for intravascular embolism protection and embolism removal or maceration.
Figure 27:
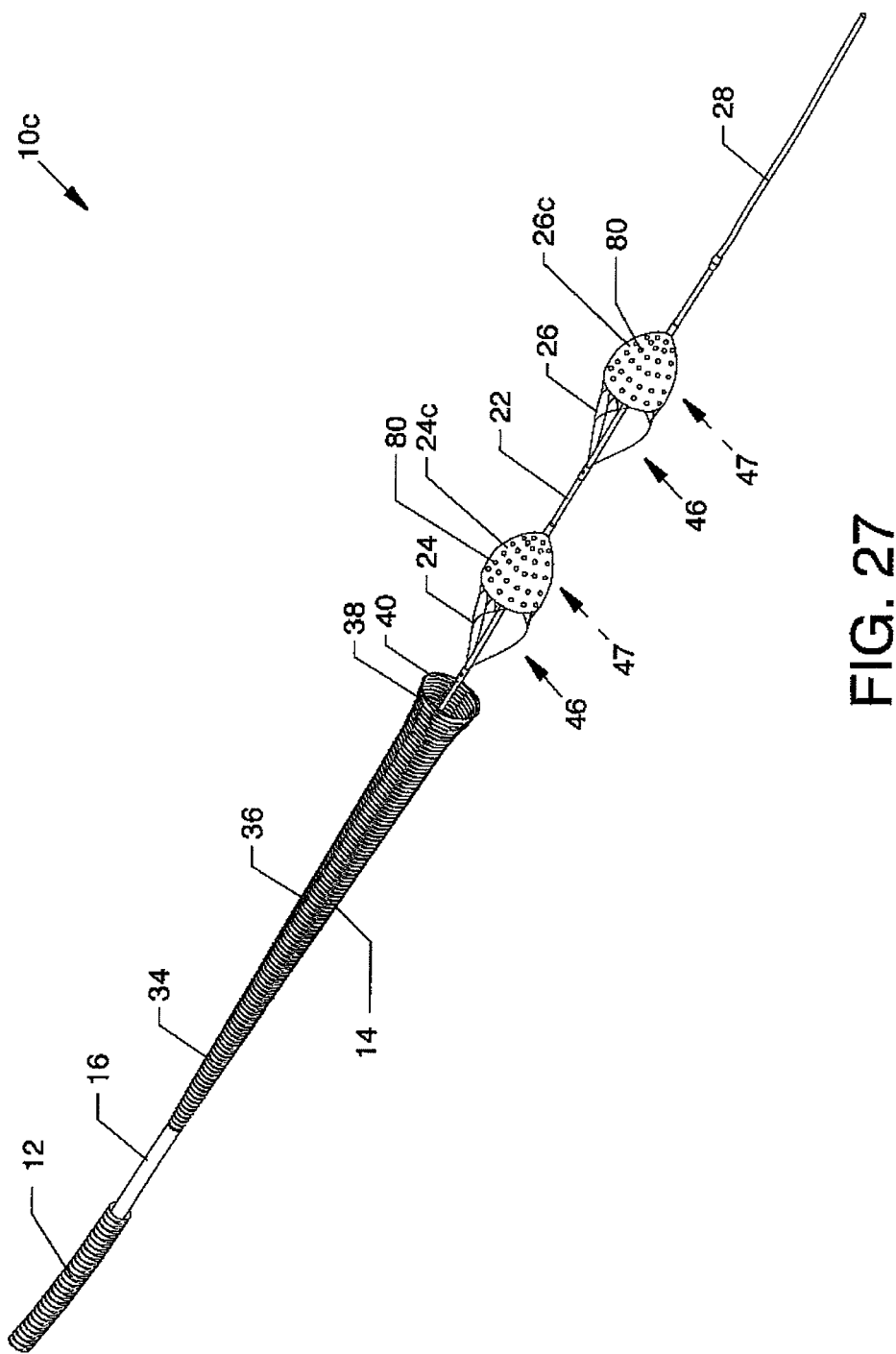
FIG. 27 is an illustration similar to FIG. 2 and is an isometric view of the guidewire filter components located at the distal region of a third alternative embodiment.

FIG. 26, a third alternative embodiment, is an isometric overview of the intravascular emboli capture and retrieval system for intravascular embolism protection and embolism removal or maceration, 10c. Generally, this alternative embodiment is useful in blood vessels of 8 mm or less to capture embolic debris, although maceration of such debris is also associated therewith and is used in much the same manner as described for the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This third alternative embodiment is similar to the preferred embodiment of FIG. 1 with the exception of the addition, arrangement, reorientation or modification of one or more filters and use thereof. As shown in FIG. 27, similarly constructed flexible proximal and distal fine filters 24c and 26c having a plurality of small orifices 80 and having generally the same shape and profile as the filter ends 47 are aligned and attached over and about filter ends 47 of the proximal filter 24 and the distal filter 26, respectively, in order to provide for a fine filtration and in order to allow for blood passage therethrough. Preferably, the proximal and distal fine filters 24c and 26c include a preformed memory shape.

FIG. 27 is an illustration similar to FIG. 2 and is an isometric view of the components located at the distal region of this third alternative embodiment of the present disclosure. Shown in particular is the addition of proximal and distal fine filters 24c and 26c over and about filter ends 47 of the proximal filter 24 and the distal filter 26.

Figure 28:
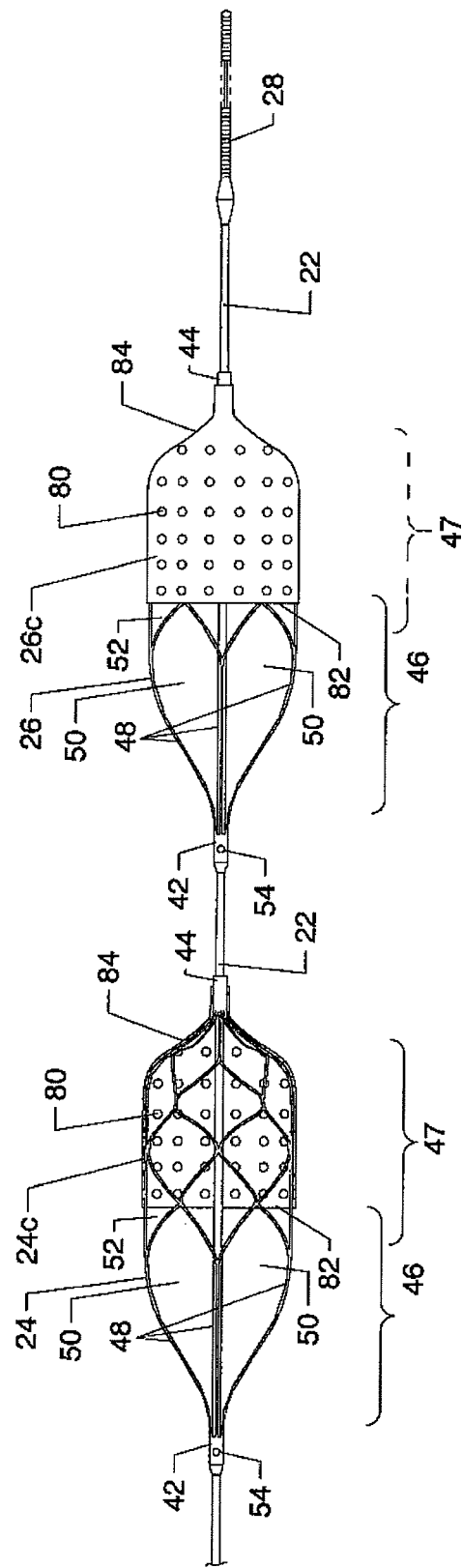
FIG. 28 is an illustration similar to FIG. 4 and is a side view of the distal end of the guidewire including the preformed memory shaped proximal filter, a preformed memory shaped distal filter and an overlying preformed memory shaped proximal fine filter and an overlying preformed memory shaped distal fine filter, respectively.
Figure 29:
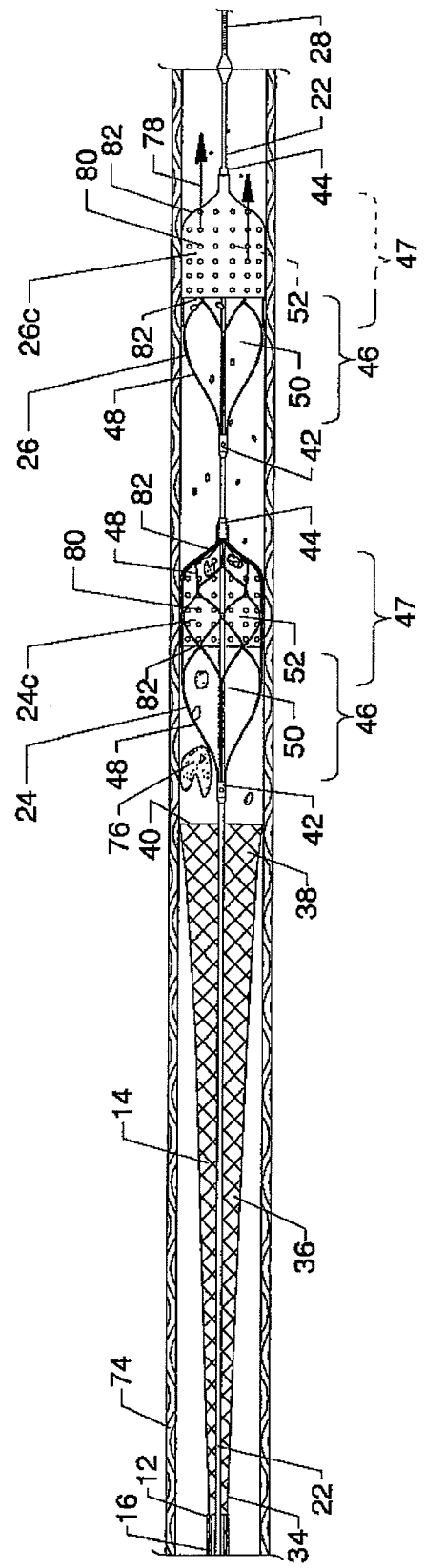
FIG. 29 is a cutaway view in partial cross section and partial cutaway view in the capture mode of the third alternative embodiment showing the proximal filter, the proximal fine filter (in cutaway view) overlying the proximal filter, the distal filter and the distal fine filter overlying the distal filter and the guidewire deployed and aligned within a blood vessel.
Figure 30:
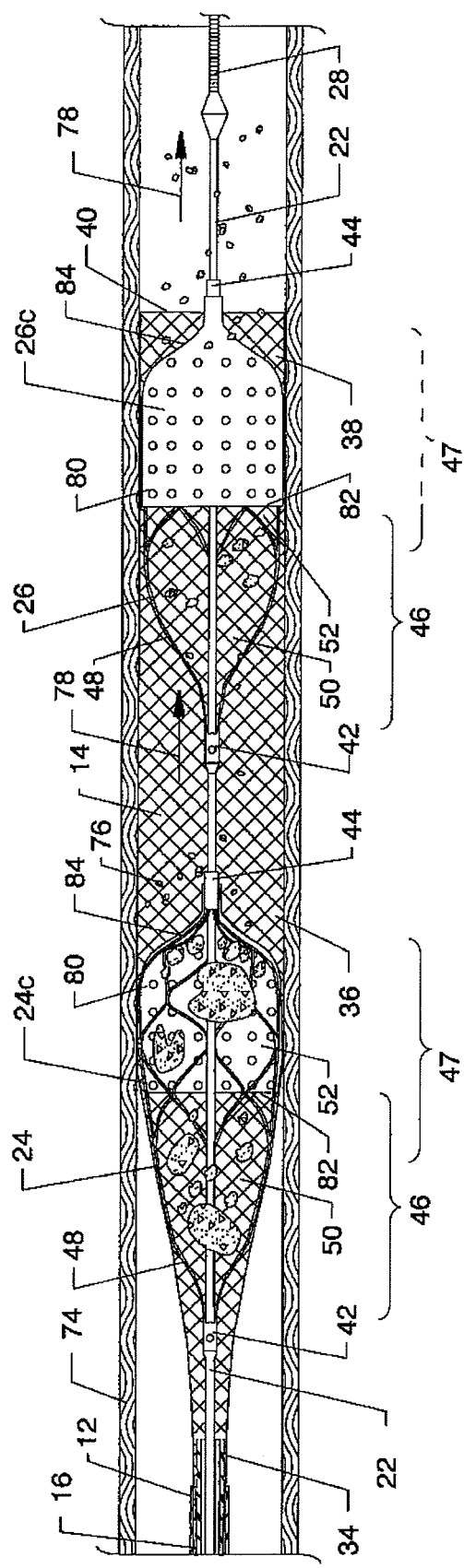
FIG. 30 is an illustration further showing the capture mode and demonstrating the full engagement of the uncompressed capture sleeve over and about the proximal filter, the overlying proximal fine filter, the distal filter, the overlying distal fine filter pieces of embolic debris and the guidewire.

FIG. 28 is an illustration similar to FIG. 4 and is a side view of the distal end of the guidewire 22 including the preformed memory shaped proximal 10 filter 24, the preformed memory shaped distal filter 26 and the overlying preformed memory shaped proximal fine filter 24c and overlying preformed memory shaped distal fine filter 26c, respectively. The shape of the proximal fine filter 24c and distal fine filter 26c resembles a short tube having an open proximal end 82 and a tapered distal end 84 where the proximal fine filter 24c and the distal fine filter 26c end. 15 Each fine filter includes a plurality of small filter orifices 80 distributed along and about the structure thereof whereby each fine filter allows for blood and small and insignificantly sized particles of embolic debris 76 to pass therethrough but traps larger pieces of embolic debris 76. The taper of the tapered distal ends 84 decreases to a suitable size in order to be secured over and about the distal tubes 44 and which 20 tapered distal ends 84 are attached to the distal tubes 44 at the ends of the proximal filter 24 and the distal filter 26. The bodies and the open proximal end 82 of the proximal fine filter 24c and distal fine filter 26c are not directly secured to the proximal filter 24 and distal filter 26 but maintain a close intimate relationship to the shape of the filter ends 47 whereby both fine filters can expand generally to the same 25 diameter size and shape as the filter ends. In FIGS. 28-30, proximal fine filter 24c is shown in cutaway view as an example to fully demonstrate its relation to proximal filter 24. The use of the fixed proximal tube 42 and the slideable distal tube 44 enables the proximal filter 24 and the distal filter 26 with the overlying attached proximal fine filter 24c and overlying attached distal fine filter 26c, respectively, to be flexibly and expandingly deployed and to be flexibly, compressingly, and elongatingly collapsed along and about the guidewire 22 whereby, in the latter condition, a lower filter profile is provided in order to facilitate their removal.

Mode of Operation

The mode of operation of the third alternative embodiment of the intravascular guidewire filter system 10c for the filtering and removal of various sized pieces of organized embolic debris is now described with reference to FIGS. 29-32, as well as understood reference to previously described figures to provide for fine filtration and to allow for blood passage therethrough. Operation of 10 the capture sleeve operator 20 and the capture/delivery sheath operator 18, used singly or together, are operated to position the capture sleeve 14 and the capture/delivery sheath 12, respectively, in cooperating operation including the movement or nonmovement of the guidewire 22 and the attached proximal filter 24, the overlying proximal fine filter 24c, the distal filter 26 and the overlying distal fine 15 filter 26c as required during various delivery and capture phases, such as previously described with reference to the preferred embodiment.

Engagement and entrapment of various pieces of the embolic debris 76, as previously described, with further and more complete fine filtration of embolic debris 76 is provided by this third alternative embodiment. Engagement and 20 entrapment of embolic debris 76 of various sizes can be accomplished by the judicious placement of the proximal filter 24 and the overlying proximal fine filter 24c and the distal filter 26 and the overlying proximal fine filter 24c. The guidewire 22 is deployed to position the proximal filter 24 and the overlying proximal fine filter 24c distal to or at a location where fine filtration is desired and then used as 25 described herein. Distal blood flow containing various sized pieces of embolic debris 76 are first encountered by the strands 48 of the large openings 50 of the proximal filter 24 to be forcibly parted, divided and macerated as previously described and thence are further urged into the combined closely associated filter end 47 and its overlying more restrictive proximal fine filter 24c. The size of the small filter orifices 80 is smaller than that of the underlying small openings 52 and therefore provides for better and more complete fine filtration than that filtration provided by the small openings 52.

As shown in FIG. 29 and with respect to this third alternate embodiment, a cutaway view is shown in partial cross section and partial cutaway view in the capture mode, the proximal filter 24, the proximal fine filter 24c (in cutaway view) overlying the proximal filter 24, the distal filter 26 and the distal fine filter 26c overlying the distal filter 26 and the guidewire 22 are deployed and aligned within a blood vessel 74 having various sized pieces of embolic debris 76 therein and located proximal and distal to the proximal filter 24 and proximal fine filter 24c. This illustration also shows the position of the flared distal section 38 of the capture sleeve 14 prior to its initial engagement with the proximal and distal filters. The capture sleeve 14, which has been expandingly deployed in the blood vessel 74 as previously described in the preferred embodiment, is shown immediately proximal to the proximal filter 24 and overlying the proximal fine filter 24c and a short distance from the distal filter 26 and overlying the distal fine filter 26c.

FIG. 30 is an illustration further showing the capture mode and demonstrating the full engagement of the uncompressed capture sleeve 14 over and about the proximal filter 24, the overlying proximal fine filter 24c, the distal filter 26, the overlying the distal fine filter 26c and pieces of embolic debris 76 some of which have been forcibly parted, divided and macerated by passage through the strands 48 of the proximal filter 24, entered through the large openings 50 and which have been captured within the proximal filter 24 and overlying the proximal fine filter 24c, as well as engagement over and about some particles of embolic debris 76 which are contained in or which are transiting the interior of the capture sleeve 14 to be further captured by the distal filter 26 and overlying distal fine filter 26c. Such engagement of the uncompressed capture sleeve 14 over and about the proximal filter 24, the overlying proximal fine filter 24c, the distal filter 26, the overlying distal fine filter 26c and pieces of embolic debris 76 may be accomplished by first advancing the capture sleeve 14 distally toward and over the proximal filter 24 and the overlying proximal fine filter 24c, the distal filter 26, and the overlying distal fine filter 26c by operation of the capture sleeve operator 20 in order to first position the flared distal section 38 and the annular edge 40 of the capture sleeve 14 in close proximity to the proximal filter 24 and overlying the proximal fine filter 24c and the pieces of embolic debris 76, such as shown in FIG. 29. The guidewire 22 can be cooperatively actuated proximally in order to urge any large pieces of embolic debris 76 into the capture sleeve 14 by impingement of the embolic debris 76 with the proximally directed proximal filter 24, thereby providing for an embolic debris entry through the flared distal section 38 and the annular edge 40 of the capture sleeve 14 and into the flared midsection 36, i.e., into the confines of the capture sleeve 14 and thence by the action of forcibly parting, dividing and maceration into the proximal filter 24 and the proximal fine filter 24c. Subsequent trapping of such processed embolic debris 76 can be provided by the distal filter 26 and the distal fine filter 26c the latter of which could include filter orifices 80 with a small radius. Very small fine particles of embolic debris 76 which pass through the proximal filter 24, the proximal fine filter 24c, the distal filter 26 and the distal fine filter 26c may be of insignificant consequence and can pass downstream.

Figure 31:
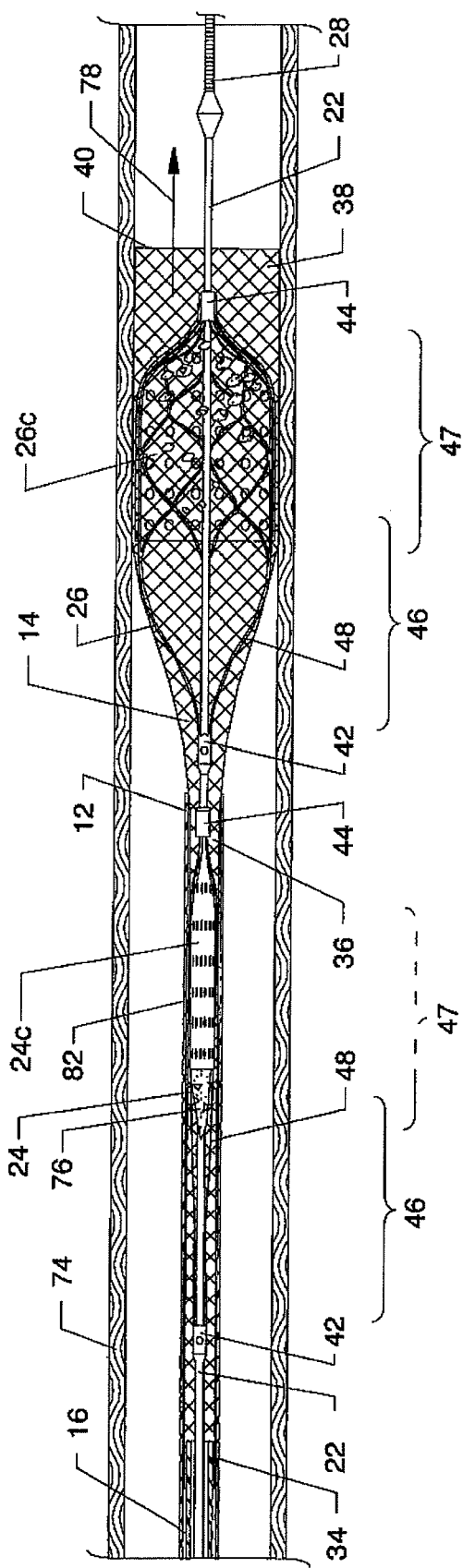
FIG. 31 is an illustration similar to FIG. 30 but where the distal filter and distal fine filter are shown in cross section view and where the proximal filter and proximal fine filter are shown in full view further showing the capture mode.

FIG. 31 is an illustration similar to FIG. 30, but where the distal filter 26 and distal fine filter 26c are shown in cross section view and where the proximal filter 24 and proximal fine filter 24c are shown in full view further showing the capture mode and demonstrating the distal positioning of the capture/delivery sheath 12 further over and about the capture sleeve 14 in order to compress the flared midsection 36 of the capture sleeve 14 and in order to compress the underlying coaxially aligned proximal filter 24 and underlying proximal fine filter 24c. Parted, divided and macerated embolic debris 76 is shown engaging the filter end 47 of the distal filter 26. The parted, divided and macerated embolic debris 76 is shown extending from the confines of the proximal fine filter 24c and the proximal filter 24 and extending into the open end 46 of the proximal filter 24.

Figure 32:
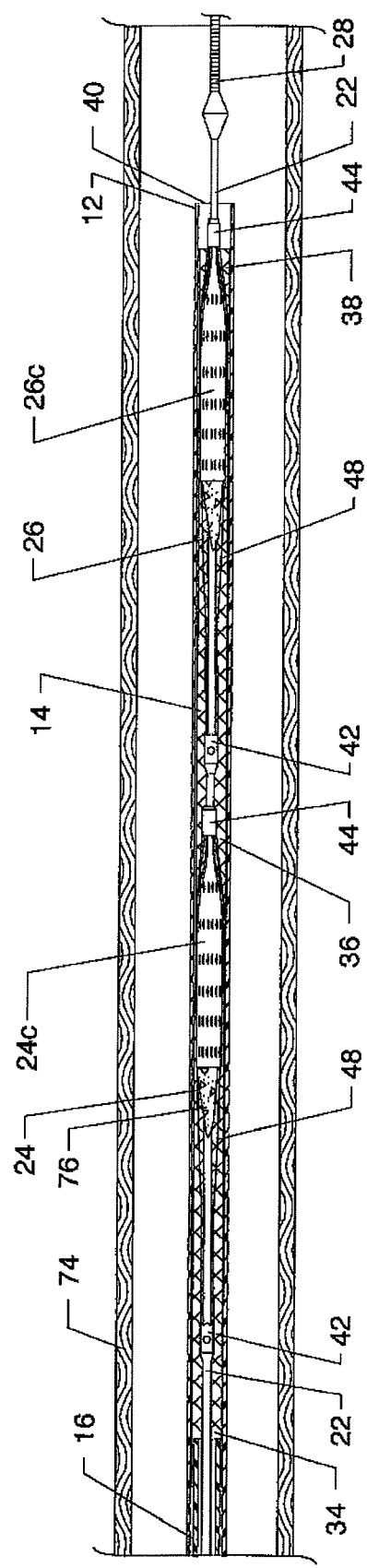
FIG. 32 is an illustration showing and demonstrating the use of the capture/delivery sheath in the full capture mode.

FIG. 32 is an illustration showing and demonstrating the use of the capture/delivery sheath 12 in the full capture mode. More specifically, collapsing of the proximal filter 24 and the underlying proximal fine filter 24c and distal filter 26 and the underlying distal fine filter 26c is assisted by the full compressed engagement 5 of the capture sleeve 14, full compressed engagement of the capture/delivery sheath 12, or both, in a manner as previously described in detail. In this illustration, the capture/delivery sheath 12 is directly and compressingly positioned over and about the capture sleeve 14 in order to provide for the complete compression of the capture sleeve 14 and is indirectly and compressingly positioned over and about the 10 coaxially aligned proximal filter 24 and the underlying proximal fine filter 24c, indirectly and compressingly positioned over and about the distal filter 26 and the distal fine filter 26c and any embolic debris 76 captured therein resulting in a compressed low profile structure of such components containing captured large or small embolic debris 76. Such a low profile structure of such components containing 15 captured embolic debris 76 may be readily withdrawn, preferably in a manner and fashion as previously described with respect to the preferred embodiment. In the alternative to the proximal fine filter 24c and the distal fine filter 26d, the filter ends 47 could be of a very fine weave which would allow the capture of very small particles of embolic debris but which would still allow passage of a sufficient amount 20 of blood flow therethrough.

Figure 33:
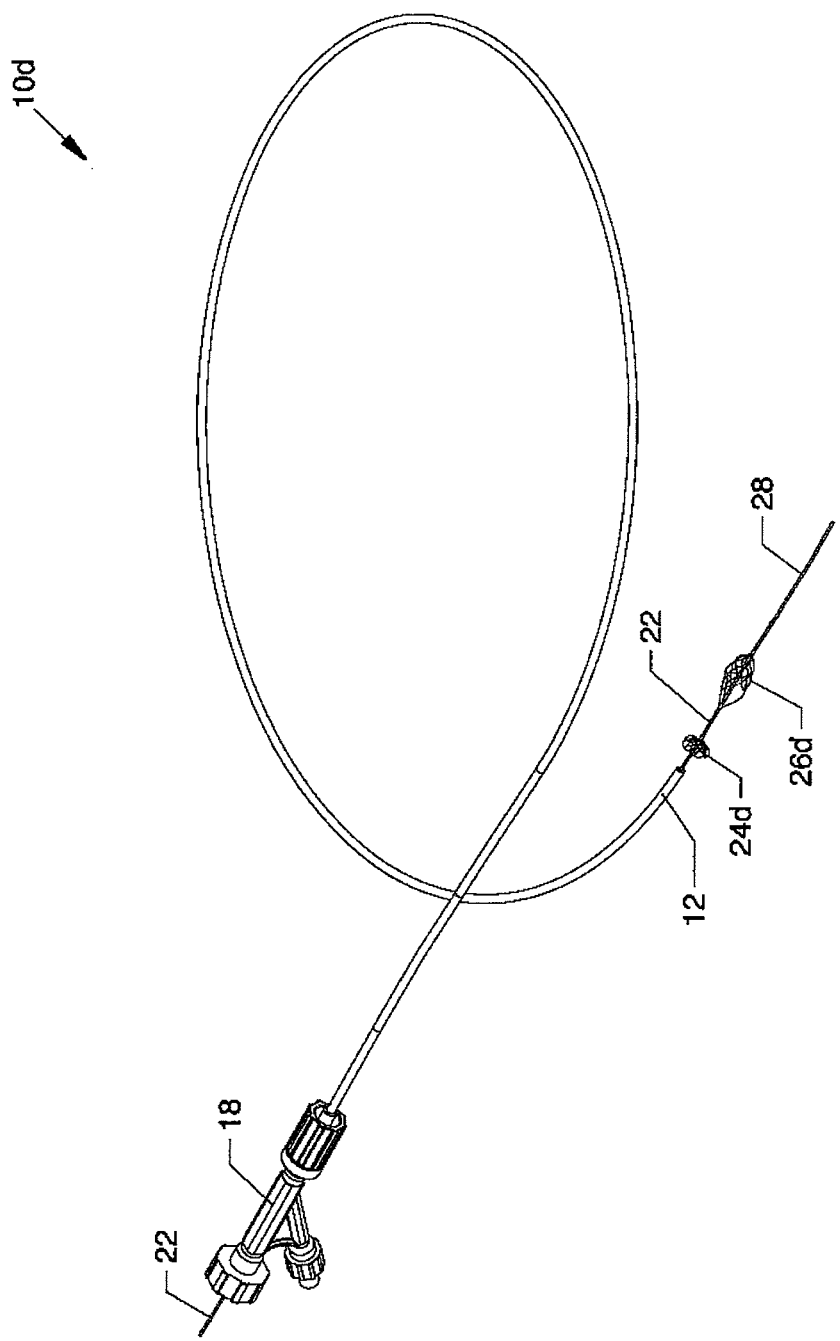
FIG. 33, a fourth alternative embodiment, resembles the second alternative embodiment and is an isometric illustration of the intravascular emboli capture and retrieval system for intravascular embolism protection and embolism removal or maceration.

FIG. 33 is a fourth alternative embodiment that resembles the second alternative embodiment and is an isometric illustration of the intravascular emboli capture and retrieval system for intravascular embolism protection and embolism removal or maceration, 10d. Generally, this alternative embodiment is 25 useful in blood vessels of 18 mm to 34 mm to part, divide and macerate large embolic debris or the removal of embolic debris 76 such as may be used by an AngioJet® thrombectomy device and catheter and does not include a capture sleeve 14, a capture sleeve operator 20 or a capture sleeve positioning tube 16 such as used and shown in the previous embodiments. Many components are constructed in a fashion similar to the preceding embodiments but are of an increased size in order to be used in femoral or other larger vessels. The proximal filter 24d is constructed using the same structure, principles and teachings of the proximal filter 24d but can be sized from 18 mm to 34 mm and the distal filter 26d is constructed using the same structure, principles and teachings of the distal filter 26 but can be sized from 18 mm to 34 mm. For purposes of example and demonstration, the capture/delivery sheath 12 can be sized at 3 mm. As can be appreciated by those of skill in the art, two or more preformed memory shaped filters can be utilized in configurations consistent with the scope of the present disclosure.

Figure 34:
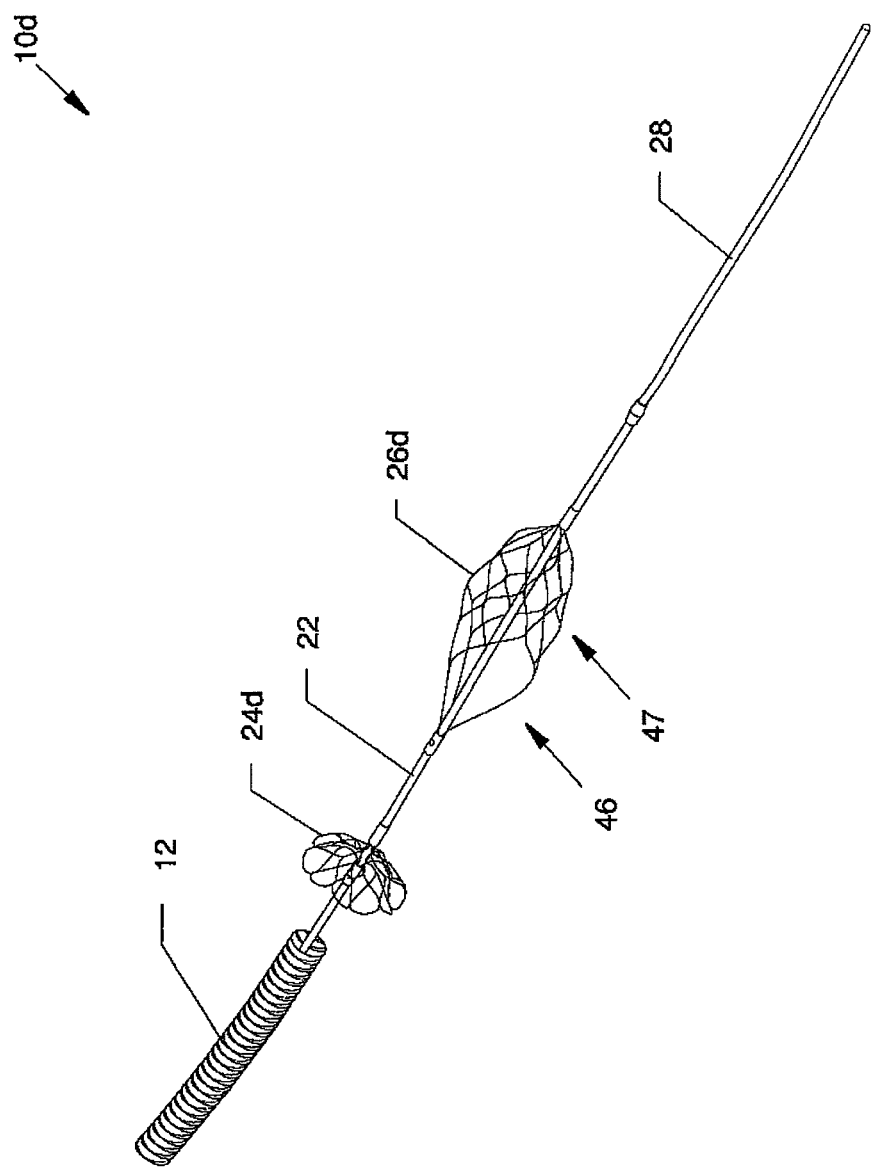
FIG. 34 is an illustration similar to FIG. 2 and is an isometric view of the components located at the distal region of this fourth alternative embodiment.

FIG. 34 is an illustration similar to FIG. 2 and is an isometric view of the components located at the distal region of this fourth alternative embodiment of the disclosure. Shown in particular is the relationship of the proximal filter 24d and the distal filter 26d to each other and to the distal end of the capture/delivery sheath 12.

Mode of Operation

The mode of operation includes expandingly deploying the proximal filter 24d and the distal filter 26d through and distal to a large embolic debris 76 and then using one or more operational modes. One mode is used to remove embolic debris 76 by the use of an AngioJet® thrombectomy device and catheter and another mode is used to part, divide and macerate the large embolic debris 76 into smaller manageable pieces. The modes of operation of this fourth alternative embodiment of the intravascular guidewire filter system 10d for the filtering and removal of various sized pieces of organized embolic debris is now described with reference to FIGS. 35 and 36, as well as understood reference to previously described figures. A larger sheath, as known in the art, is used to insert the flexible guidewire 22 and the proximal filter 24d and the distal filter 26d into the vasculature. Operation of the capture/delivery sheath operator 18 positions the capture/delivery sheath 12 in cooperating operation with the flexible guidewire 22 and the attached proximal filter 24d and distal filter 26d, as required. Engagement and treatment of large embolic debris 76 can be accomplished by the judicious placement of the proximal filter 24d and the distal filter 26d with respect to the large embolic debris 76.

Figure 35:
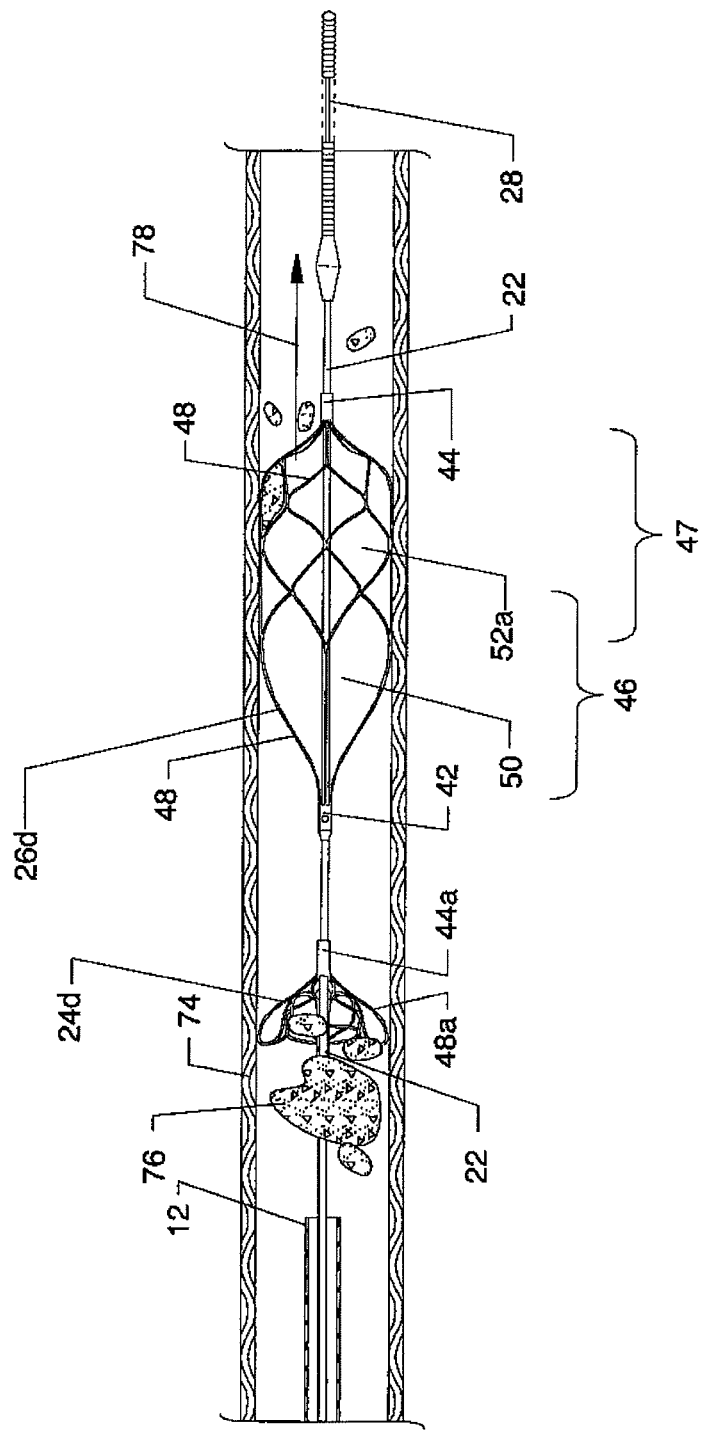
FIG. 35 is a cutaway view shown in partial cross section and partial cutaway view in the capture mode showing the proximal filter (in cutaway view), the distal filter, and the guidewire deployed and aligned in a blood vessel.

As shown in FIG. 35 and with respect to this fourth alternative embodiment, a cutaway view is shown in partial cross section and partial cutaway view in the capture mode showing the proximal filter 24d (in cutaway view), the distal filter 26d, and the guidewire 22 deployed and aligned in a blood vessel 74 and further showing a large piece of embolic debris 76 engaging the proximal filter 24d. The large piece of embolic debris 76 encounters the filtering weave of the strands 48a located on the proximal filter 24d which initially and wholly engages the large piece of embolic debris 76 with minimum, if any, parting, dividing or macerating. The capture/delivery sheath 12 can be retracted and then removed from about the guidewire 22 and an AngioJet® thrombectomy device and catheter can be engaged over and about the guidewire 22 and utilized to macerate and remove the embolic debris 76 which is in intimate contact with the proximal filter 24*d*.

Figure 36:
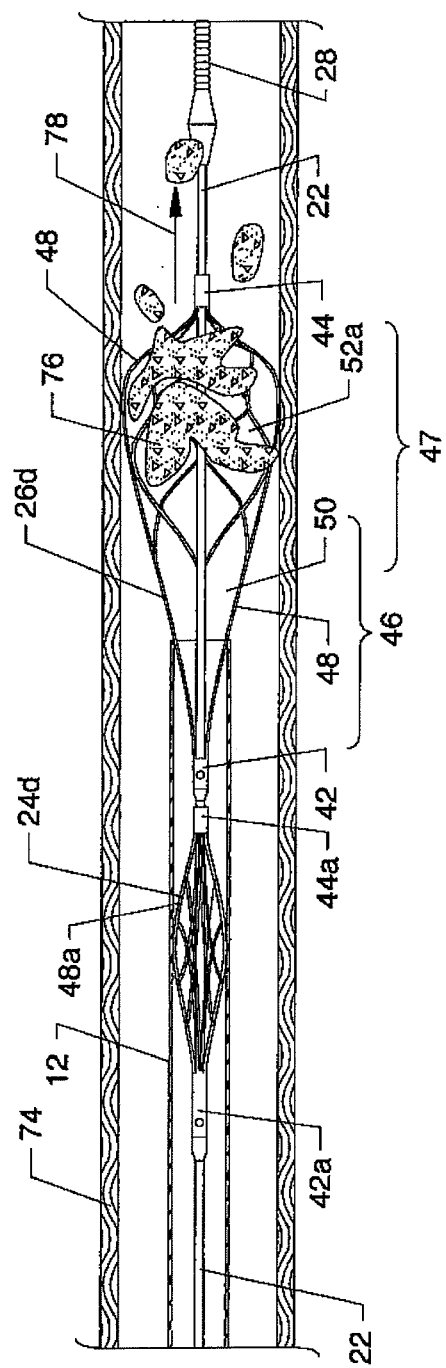
FIG. 36 is an illustration showing yet another operational mode but where the distal filter is shown in cross section view further showing the capture mode and demonstrating the full compression of the proximal filter.

FIG. 36 is an illustration showing yet another operational mode of the fourth alternative embodiment, but where the distal filter 26*d* is shown in cross section view and further showing the capture mode and demonstrating the full compression of the proximal filter 24*d* which is shown having been positioned proximally to be contained within the capture/delivery sheath 12, the latter of which is again positioned over and about the guidewire 22. Also shown is an embolic debris 76 which has been urged along the blood vessel 74 and along the exterior of the capture/delivery sheath 12 and which has entered the open end 46 of the distal filter 26*d*. The further distally directed positioning of the distal end of the capture/delivery sheath 12 over and about the distal filter 26*d* and the strands 48 causes the elongation and compression of the distal filter 26*d*. Such compression causes the parting, division and maceration of the embolic debris 76 engaging the open end 46 and the filter end 47 of the distal filter 26*d* as the distal filter 26*d* is retrieved into the capture/delivery sheath 12.

The capture/delivery sheath 12 is progressively, directly, compressingly, and distally positioned over and about the distal filter 26*d* and engaged with the embolic debris 76 in order to progressively part, divide and macerate the embolic debris 76 and force its passage through the small openings 52*a* in the form of relatively small pieces which can be carried downstream as urged by bloodflow. Finally, the capture/delivery sheath 12 fully compresses the distal filter 26*d* to a minimum profile, such as suggested with reference to FIG. 25. Such a low profile structure of such components may be readily withdrawn, preferably in the general manner and fashion as previously described with respect to the preferred embodiment. In the alternative, a guidewire 22 having either a proximal filter 24*d* or a distal filter 26*d* can be used to part, divide and macerate the large embolic debris 76 in the manner as described herein.

Figure 37:
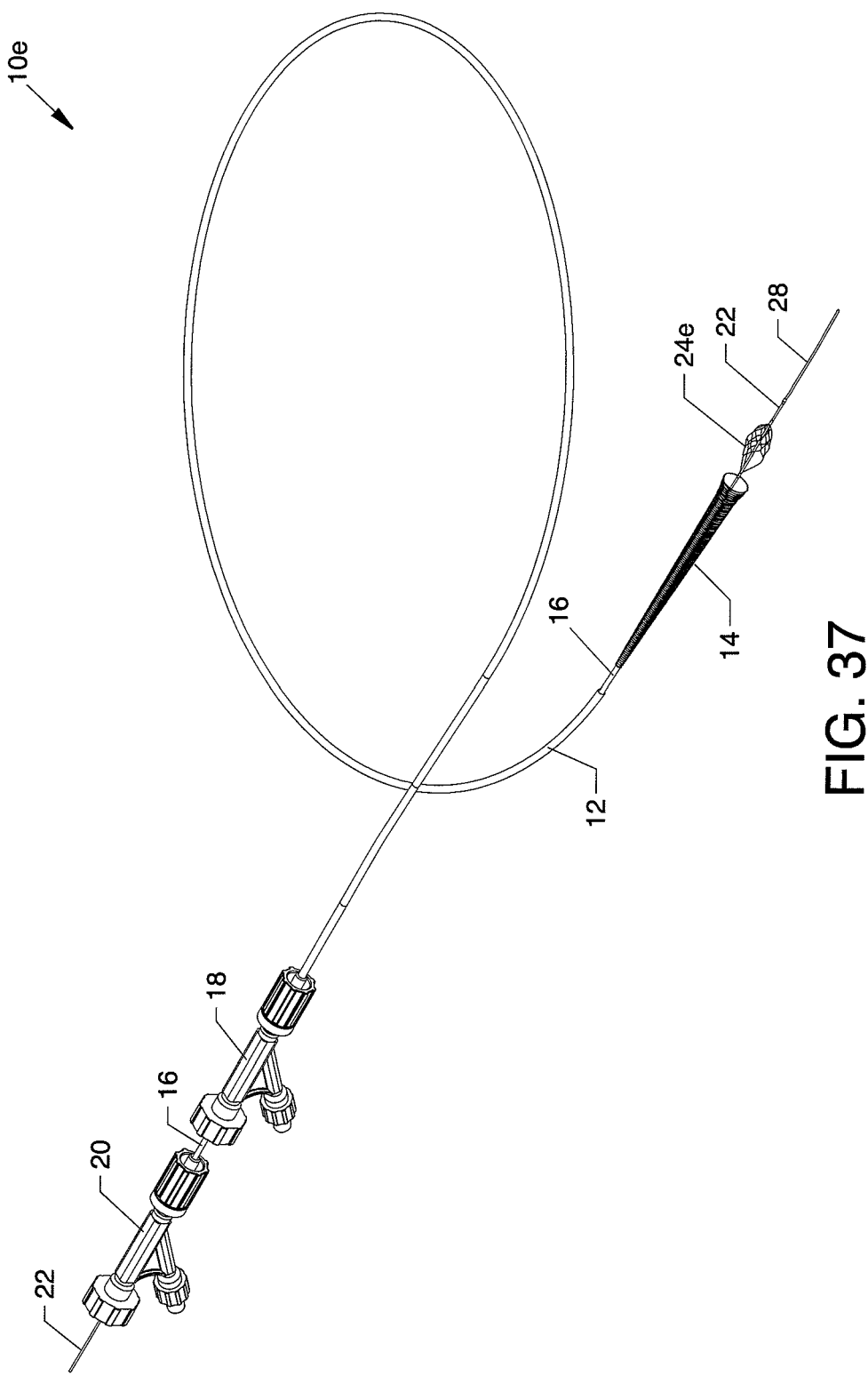
FIG. 37, a fifth alternative embodiment, is an isometric overview of the intravascular emboli capture and retrieval system for intravascular embolism protection and embolism removal or maceration.

FIG. 37, a fifth alternative embodiment, is an isometric overview of the intravascular embolic capture and retrieval system for intravascular embolism protection and embolism removal, 10*e*. Generally, this alternative embodiment is useful in blood vessels of 8 mm or less to capture embolic debris although maceration of such debris is also associated therewith and is used in a closely related manner as previously described for the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This fifth alternative embodiment is similar to and closely related to the preferred embodiment of FIG. 1 but instead of the proximal filter 24 and the distal filter 26 only one similarly constructed filter 24*e* which is not designated as distal or proximal is used. The flexible preformed memory shaped filter 24*e* of this fifth alternative embodiment which can be deployed distal to large embolic debris 76 is used in lieu of the preformed memory shaped distal filter 26 and the preformed memory shape proximal filter 24 of the preferred embodiment and is located on the guidewire 22 including the same shape and the same characteristics. As can be appreciated by those of skill in the art, one or more preformed memory shaped filters can be utilized in configurations consistent with the scope of the present disclosure.

Figure 38:
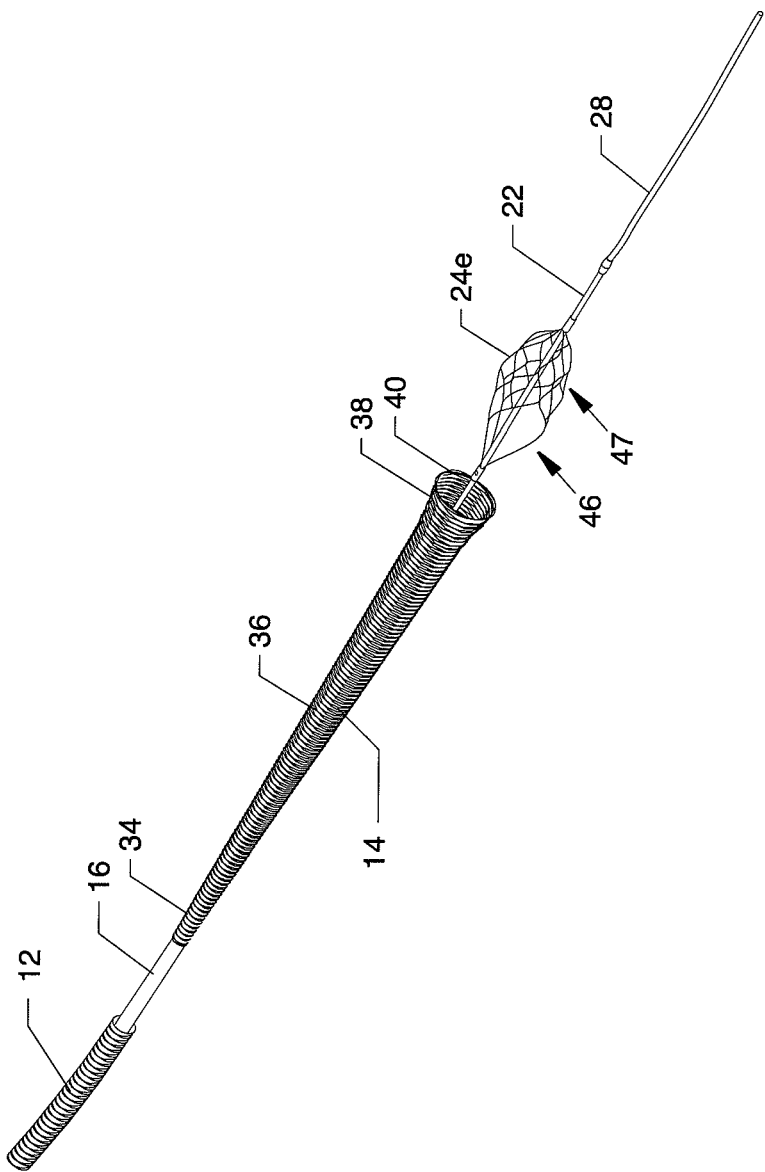
FIG. 38 is an illustration similar to FIG. 2 and is an isometric view of the components located at the distal region of the fifth alternative embodiment.

FIG. 38 is an illustration similar to FIG. 2 and is an isometric view of the components located at the distal region of the fifth alternative embodiment of the present disclosure. Shown, in particular, is the relationship of the filter 24*e* to the capture sleeve 14.

Mode of Operation

The mode of operation of the fifth alternative embodiment of the intravascular guidewire filter system 10*e* for the filtering and removal of various sized pieces of organized embolic debris is now described with reference to FIGS. 39-42 as well as understood reference to previously described figures. The capture sleeve operator 20 and the capture/delivery sheath operator 18, used singly or together, are operated to position the capture sleeve 14 and the capture/delivery sheath 12, respectively, in cooperating operation including the movement or nonmovement of the guidewire 22 and the attached filter 24*e* as required during various delivery and capture phases, such as previously described with reference to the preferred embodiment. Engagement and entrapment of the large embolic debris 76 can be accomplished by the judicious placement of the filter 24*e* with respect to the large embolic debris 76. With respect to the large embolic debris 76, the guidewire 22 is deployed to position the filter 24*e* distal to the large piece of embolic debris 76 and used as described herein.

Figure 39:
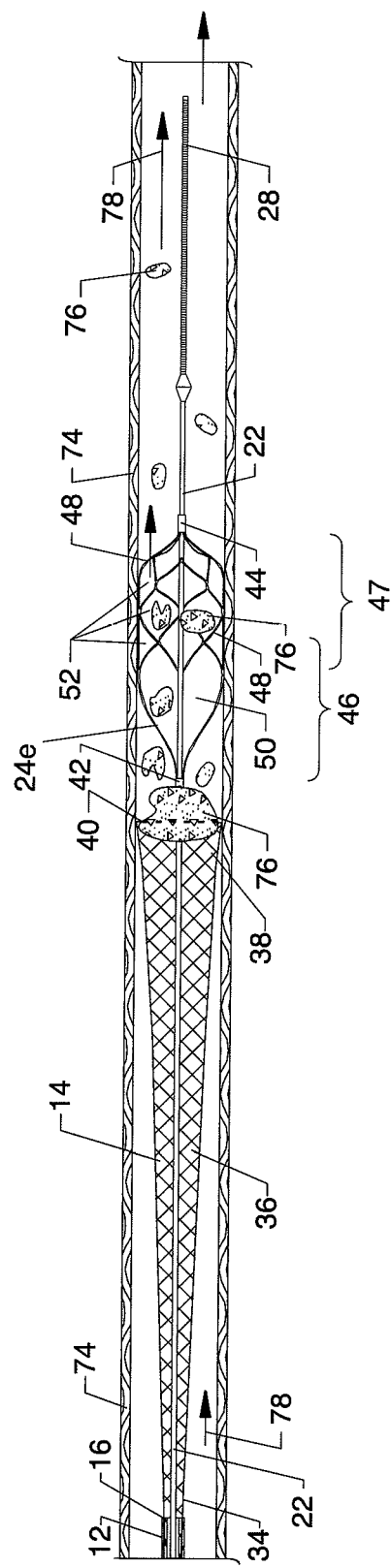
FIG. 39 is a cutaway view is shown in partial cross section and partial cutaway view in the capture mode.

As shown in FIG. 39 and with respect to the fifth alternative embodiment, a cutaway view is shown in partial cross section and partial cutaway view in the capture mode showing the filter 24*e* (in cutaway view) and the guidewire 22 deployed and aligned within a blood vessel 74 showing a large piece of embolic debris 76 located proximal to the filter 24*e* just prior to initial engagement of the filter 24*e* and during initial engagement of the embolic debris 76 by the flared distal section 38 of the capture sleeve 14. The capture sleeve 14 which has been expandingly deployed in the blood vessel 74, as previously described in the preferred embodiment, is shown immediately proximal to the filter 24*e*. Manual positioning of the guidewire 22 in a proximal direction first causes the open end 46 and then causes the deployed filter end 47 of the filter 24*e* to engage and urge the large piece of embolic debris 76 proximally into the flared distal section 38 of the capture sleeve 14, the latter of which may be urged distally to cooperatively accommodate the large piece of embolic debris 76.

Figure 40:
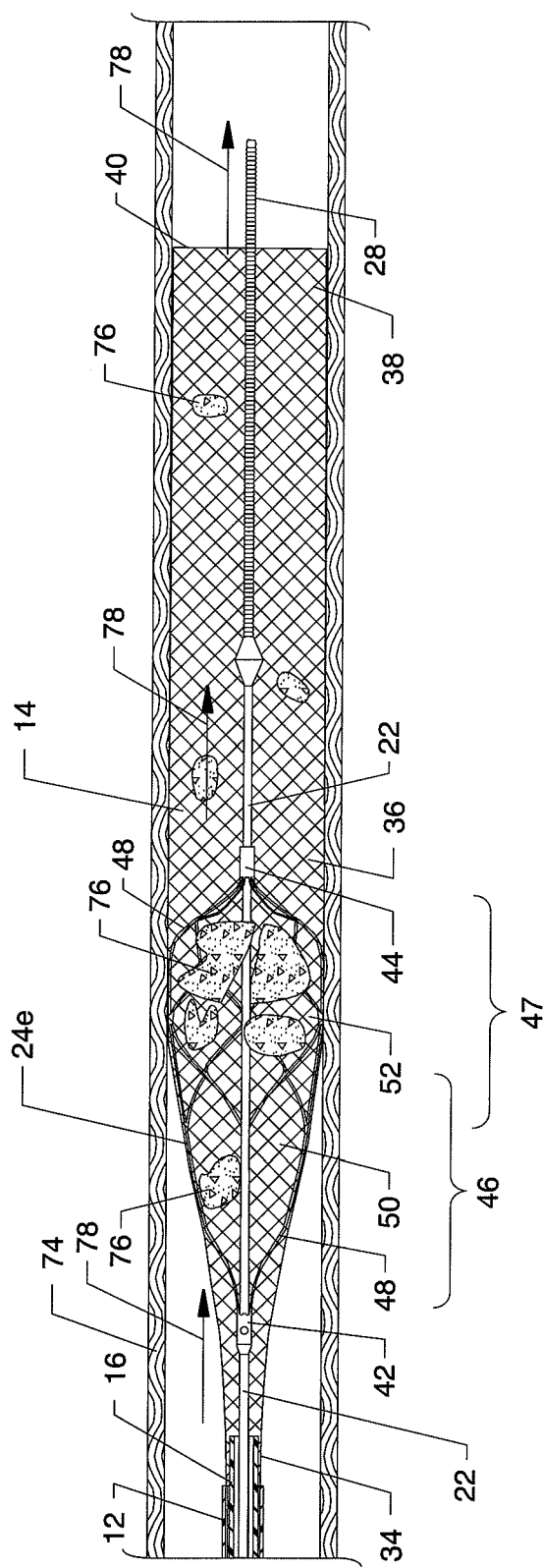
FIG. 40 is an illustration similar to FIG. 6 further showing the use of the capture sleeve in the capture mode by showing the engagement of the capture sleeve over and about the filter which has entrapped embolic debris therein.

Engagement and entrapment of embolic debris 76 can be accomplished either by the distal blood flow containing smaller pieces of embolic debris 76 into the proximal filter 24 and/or the distal filter 26, as previously described, or by the manual forcible urging of the guidewire 22 and the connected filter 24*e* proximally to forcibly and robustly engage, part, divide and macerate large pieces or collections of embolic debris 76 which can be temporarily urged into and temporarily fixed in place for parting in the capture sleeve 14 by contact caused by the proximal urging of the filter 24*e*. Some of the large pieces of embolic debris 76 can be engaged, parted, divided and macerated by blood flow induced forced contact with the strands 48 of the filter 24*e* and can gain entry into the interior of the filter 24*e* through the large openings 50 of the proximally located open end 46 during parting, dividing and macerating where entrapment is provided by the strands 48 at the small openings 52 in the distally located filter end 47 as shown in FIG. 40. Small particles of embolic debris 76 may pass directly through the large openings 50 for 2trapping by the strands 48 at the small openings 52 at the distally located filter end 47 of the filter 24e without contacting the strands 48 of the large openings 50. Very small particles of embolic debris 76 which pass through the located filter ends 47 of the filter 24e may be of insignificant consequence and can pass downstream.

FIG. 40 is an illustration similar to FIG. 6 further showing the use of the capture sleeve 14 in the capture mode by showing the engagement of the capture sleeve 14 over and about the filter 24e which has entrapped embolic debris 76 therein. Such engagement is accomplished by advancing the capture sleeve 14 distally toward and over the filter 24e by operation of the capture sleeve operator 20. The guidewire 22 can be cooperatively actuated proximally in order to cause intimate contacting and pulling and urging the large piece of embolic debris 76 into the capture sleeve 14 by impingement of the embolic debris 76 by the features of the proximally directed filter 24e, and thence through the flared distal section 38 and the annular edge 40 of the captive sleeve 14 and into the flared midsection 36, i.e., the confines of the capture sleeve 14.

Figure 41:
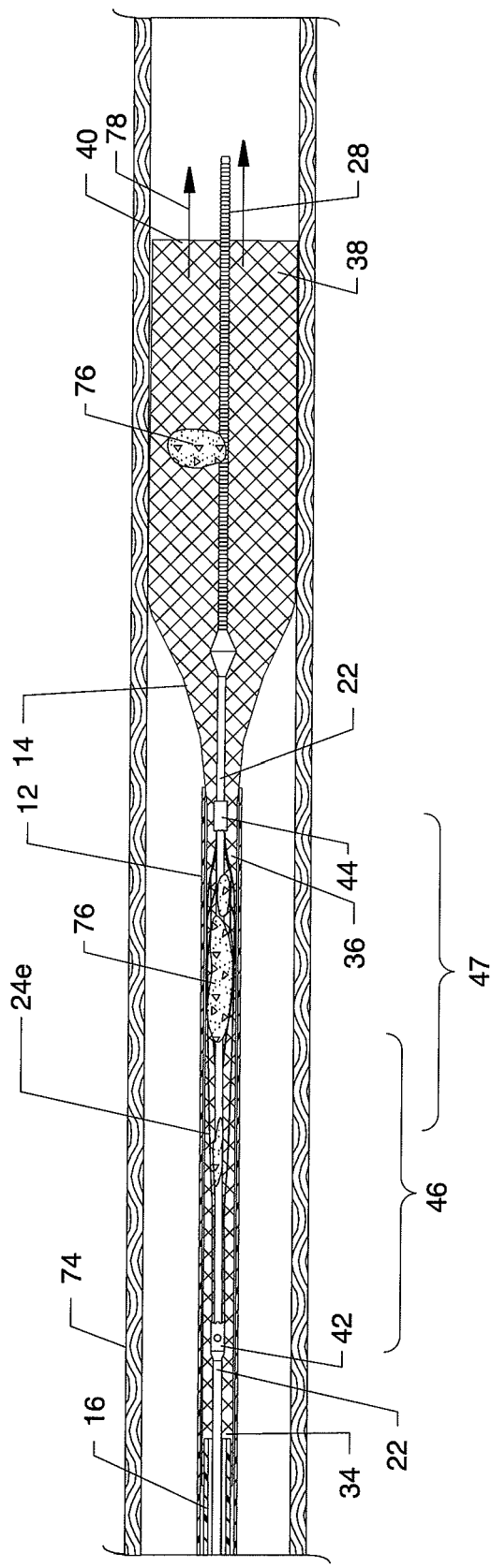
FIG. 41 is an illustration similar to FIG. 7 further showing the use of the capture sleeve and the capture/delivery sheath in the capture mode.

FIG. 41 is an illustration similar to FIG. 7 further showing the use of the capture sleeve 14 and the capture/delivery sheath 12 in the capture mode. Operation of the capture/delivery sheath operator 18 distally forces the capture/delivery sheath 12 distally, whereby the distal end of the capture/delivery sheath 12 is progressively positioned directly over and about the capture sleeve 14 and, simultaneously, is progressively and indirectly positioned over and about the filter 24e which is coaxially aligned within the capture sleeve 14. Such distal progressive distal positioning of the capture/delivery sheath 12 forcibly compresses the capture sleeve 14, the underlying filter 24e and the embolic debris 76 which has been captured within the filter 24e. During compression, the embolic debris 76 can also be elongated or may beneficially be further parted, divided and macerated into smaller pieces.

Figure 42:
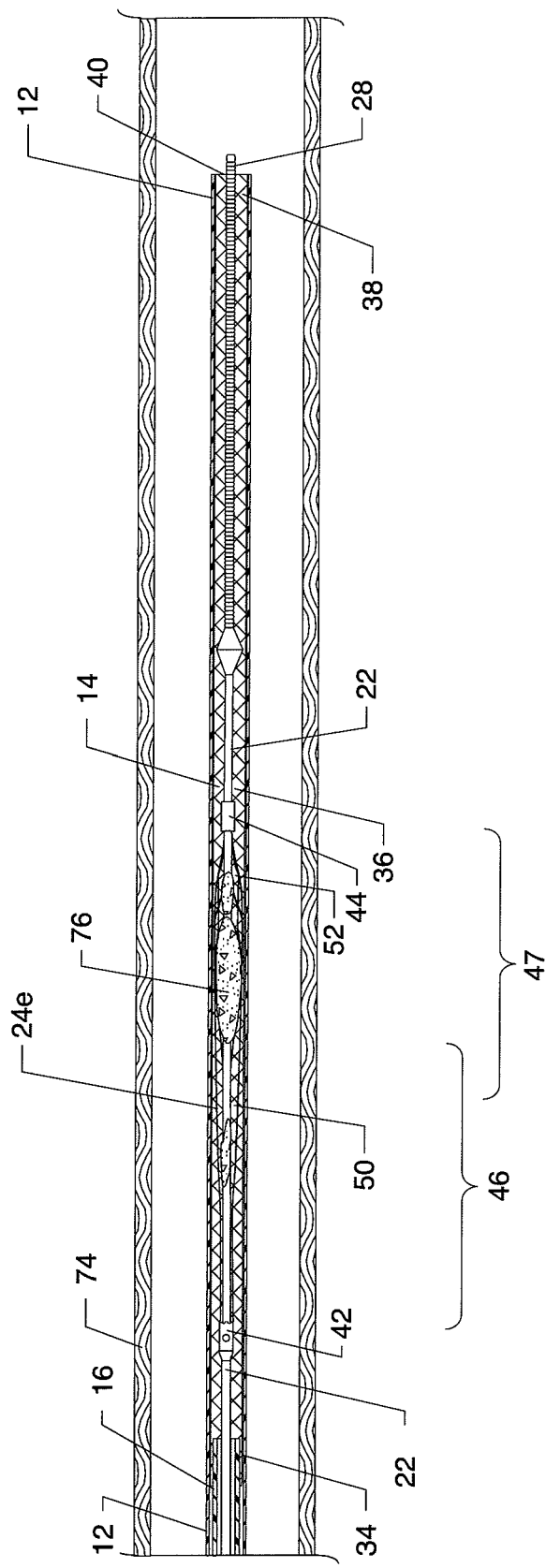
FIG. 42 is an illustration similar to FIG. 8 further showing the use of the capture sleeve and the capture/delivery sheath in the capture mode.

FIG. 42 is an illustration similar to FIG. 8 further showing the use of the capture sleeve 14 and the capture/delivery sheath 12 in the capture mode. In this illustration, the capture/delivery sheath 12 is positioned further and fully in a distal direction to force complete compression of the capture sleeve 14 where the capture/delivery sheath 12 is also in alignment directly over and about the distal portion of the capture sleeve 14 and simultaneously is indirectly and compressingly positioned over and about the filter 24e which is in coaxial alignment within the capture sleeve 14. Complete compression of the capture sleeve 14 indirectly over and about the filter 24e and the embolic debris 76 captured therein provides a low profile structure of such components containing captured embolic debris 76. Components of such low profile structure containing captured embolic debris 76 may be readily withdrawn, preferably in simultaneous fashion, proximally through the capture/delivery sheath 12 where the capture sleeve positioning tube 16, the embolic debris laden capture sleeve 14, the guidewire 22 and the compressed embolic debris laden filter 24e can be withdrawn in a proximally directed removal from the capture/delivery sheath 12 by a proximal and manual directed unitary movement of the capture/delivery sheath operator 18, the capture sleeve operator 20 and attached capture sleeve positioning tube 16, and the guidewire 22. In the alternative, the capture sleeve positioning tube 16, the embolic debris laden capture sleeve 14, the guidewire 22 and filter 24e and the capture/delivery sheath 12 may be entirely and unitarily withdrawn from the blood vessel 74 by the proximal and manually directed movement of the capture/delivery sheath operator 18, the capture sleeve operator 20 and the guidewire 22.

Figure 43:
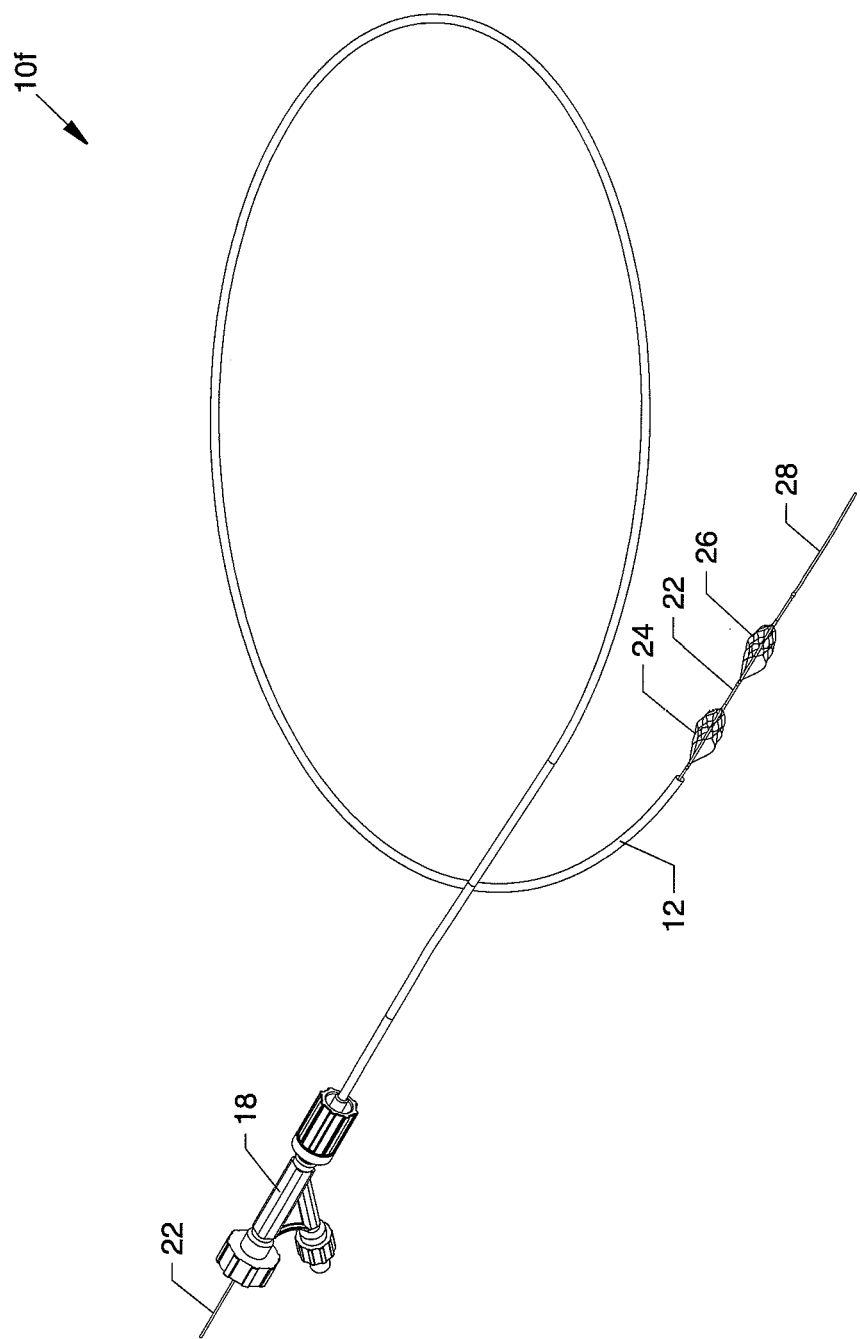
FIG. 43, a sixth alternative embodiment, is an isometric overview of the intravascular emboli capture and retrieval system for intravascular embolism protection and embolism removal or maceration.

FIG. 43, a sixth alternative embodiment, is an isometric overview of the intravascular emboli capture and retrieval system for intravascular embolism protection and embolism removal or maceration, 10f. Generally, this alternative embodiment is useful in blood vessels of 8 mm or less to capture embolic debris although maceration of such debris is also associated therewith and is used in a closely related manner as previously described for the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This sixth alternative embodiment is similar to and closely related to the preferred embodiment of FIG. 1 and the use thereof but does not use the capture sleeve 14. As can be appreciated by those of skill in the art, two or more preformed memory shaped filters can be utilized in configurations consistent with the scope of the present disclosure.

Figure 44:
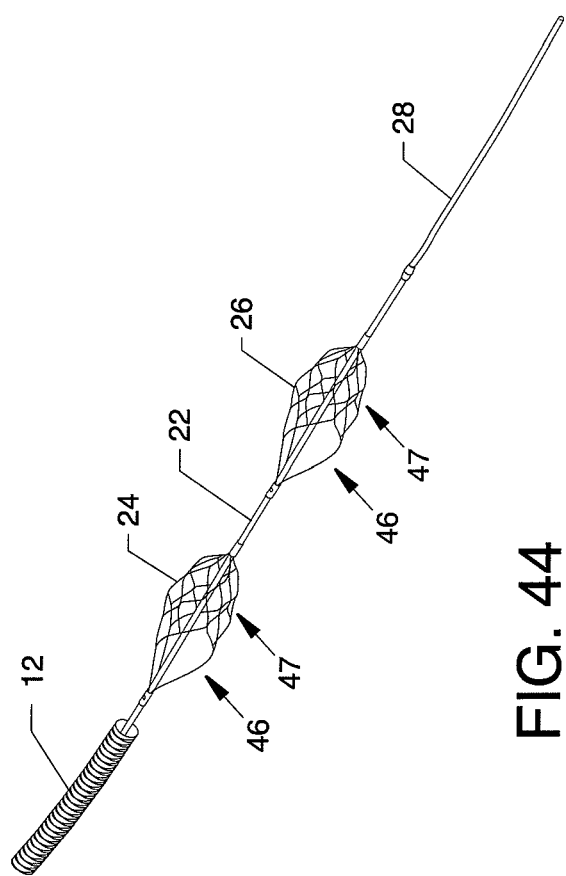
FIG. 44 is an illustration similar to FIG. 2 and is an an isometric view of the components located at the distal region of the sixth alternative embodiment of the present invention.

FIG. 44 is an illustration similar to FIG. 2 and is an isometric view of the components located at the distal region of the sixth alternative embodiment of the present disclosure. Shown, in particular, is the relationship of the proximal filter 24 and the distal filter 26 to the capture delivery sheath 12.

Mode of Operation

The mode of operation of the sixth alternative embodiment of the intravascular guidewire filter system 10f for the filtering and removal of various sized pieces of organized embolic debris is now described with reference to FIGS. 45-48, as well as understood reference to previously described figures. The capture/delivery sheath operator 18 is operated to position the capture/delivery sheath 12 preferably in cooperative operation including the movement or nonmovement of the guidewire 22 and the attached proximal filter 24 and distal filter 26 as required during various delivery and capture phases, such as previously described with reference to the preferred embodiment. Engagement and entrapment of the large embolic debris 76 can be accomplished by the judicious placement of the proximal filter 24 with respect to the large embolic debris 76. With respect to the large embolic debris 76, the guidewire 22 is deployed to position the proximal filter 24 distal to the large piece of embolic debris 76 and used as described herein.

Figure 45:
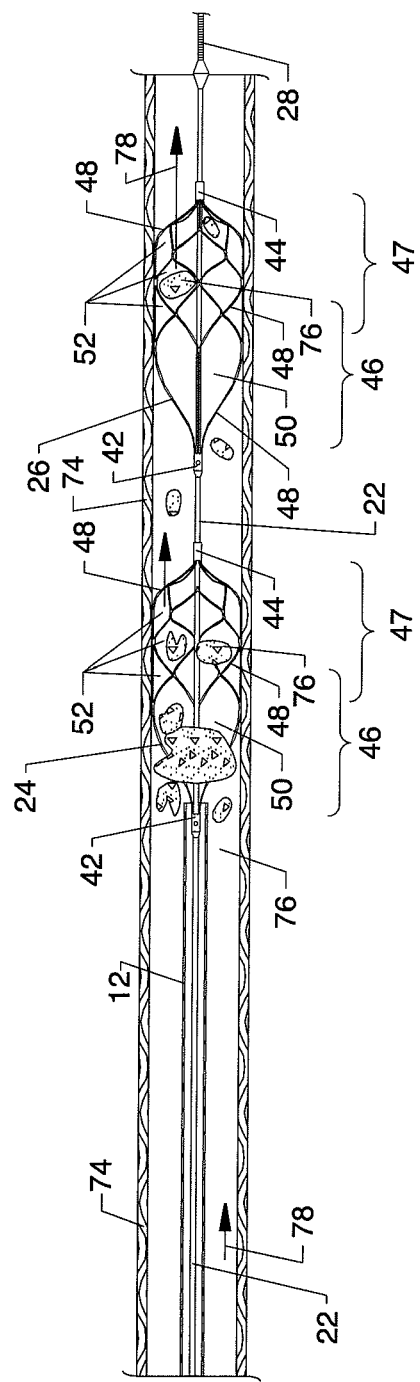
FIG. 45 is a cutaway view of the sixth alternative embodiment shown in partial cross section and partial cutaway view.

As shown in FIG. 45 and with respect to the sixth alternative embodiment, a cutaway view is shown in partial cross section and partial cutaway view in the capture mode showing the proximal filter 24 (in cutaway view), the distal filter 26 and the guidewire 22 deployed and aligned within a blood vessel 74 showing a large piece of embolic debris 76 in initial engagement with the proximal filter 24.

Figure 46:
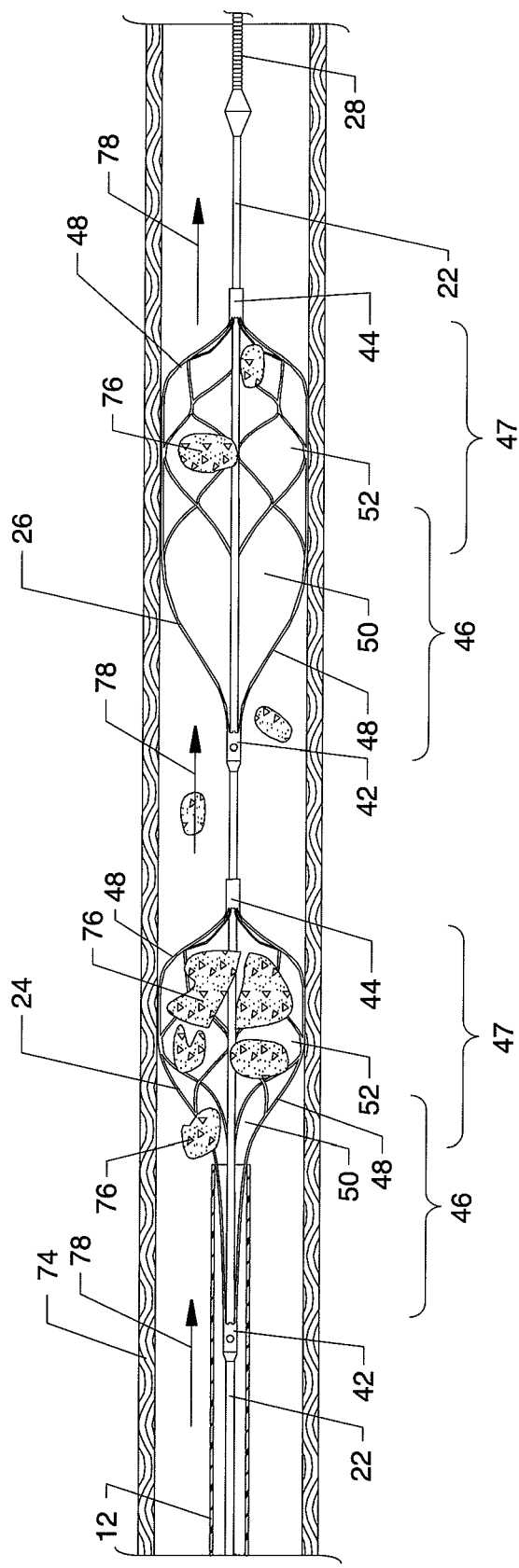
FIG. 46 is an illustration similar to FIG. 6 further showing the initial engagement of the capture/delivery sheath over and about the open end of the proximal filter, shown partially collapsed, which has embolic debris entrapped therein.
Figure 47:
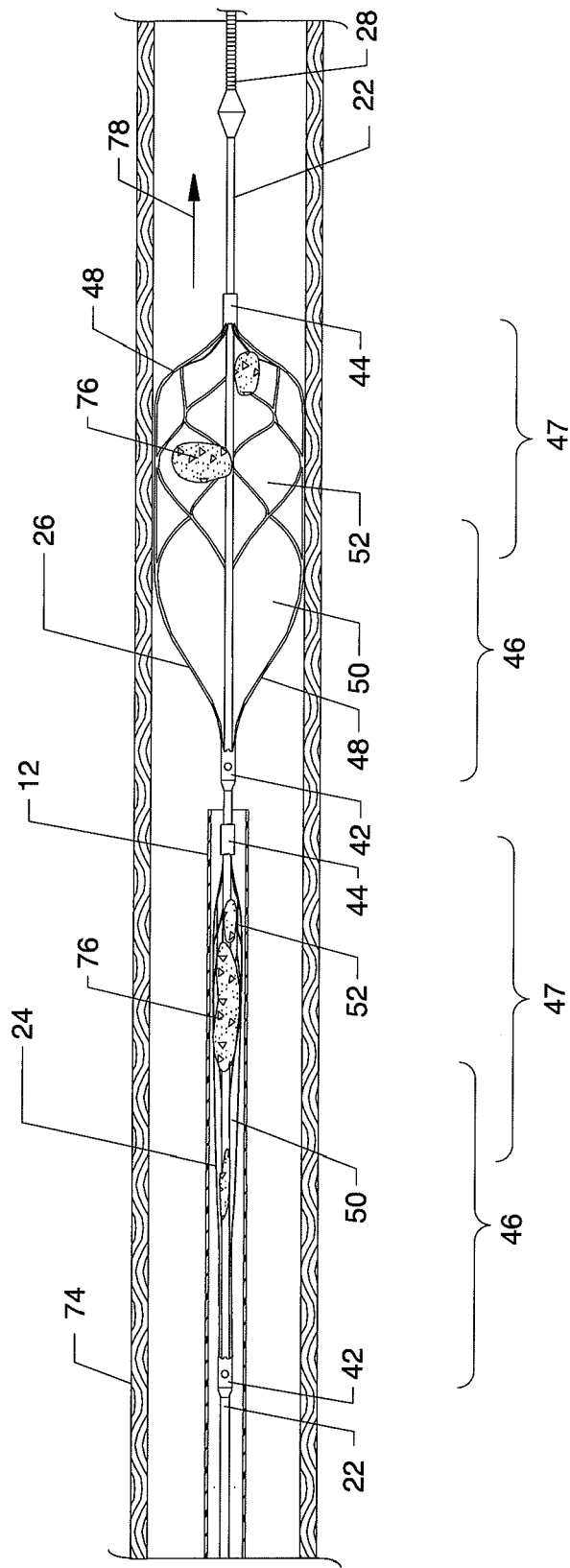
FIG. 47 is an illustration similar to FIG. 7 further showing the use of the capture/delivery sheath in the capture mode.

Engagement and entrapment of the embolic debris 76 can be accomplished either by the distal blood flow containing smaller pieces of embolic debris 76 into the proximal filter 24 and/or the distal filter 26 as previously described, or by the manual forcible urging of the guidewire 22 and the connected proximal filter 24 and the distal filter 26 proximally to forcibly and robustly engage, part, divide and macerate large pieces or collections of embolic debris 76 as described in FIG. 46. Some of the large pieces of embolic debris 76 which can be engaged, parted, divided and macerated by blood flow induced and forced contact with the strands 48 of the proximal filter 24 and can gain entry into the interior of the proximal filter 24 through the large openings 50 of the proximally located open end 46 during such engagement, parting, dividing and macerating where entrapment is provided by the strands 48 at the small openings 52 in the distally located filter end 47 as shown in FIG. 47. Small particles of embolic debris 76 may pass directly through the large openings 50 for trapping by the strands 48 at the small openings 52 at the distally located filter end 47 of the proximal filter 24 without contacting the strands 48 of the large openings 50. Very small particles of embolic debris 76 which pass through the located filter ends 47 of the proximal filter 24 (and the distal filter 26) may be of insignificant consequence and can pass downstream.

FIG. 46 is an illustration similar to FIG. 6 further showing the initial engagement of the capture/delivery sheath 12 over and about the open end 46 of the proximal filter 24, shown partially collapsed, which has embolic debris 76 entrapped therein. Such engagement is accomplished by advancing the capture/delivery sheath 12 distally toward and over the proximal filter 24 and then the distal filter 26 by operation of the capture/delivery sheath operator 18 in order to forcibly collapse the proximal filter 24 and then the distal filter 26 over and about any embolic debris which may be located within the open end 46 or the filter end 47 of the proximal filter 24 and then the open end 46 or the filter end 47 of the distal filter 26. The guidewire 22 can be cooperatively actuated proximally in order to assist in intimate contacting and collapsing of the proximal filter 24 and the distal filter 26 in order to accomplish destruction or reforming of the embolic debris 76 where the strands 48 forcibly and robustly engage, part, divide and macerate embolic debris 76 by impingement of the embolic debris 76 by the features of the proximal filter 24 and the distal filter 26.

FIG. 47 is an illustration similar to FIG. 7 further showing the use of the capture/delivery sheath 12 in the capture mode. Operation of the capture/delivery sheath operator 18 forces the capture/delivery sheath 12 distally whereby the distal end of the capture/delivery sheath 12 is progressively positioned directly over and about the proximal filter 24. Such distal progressive distal positioning of the capture/delivery sheath 12 forcibly compresses the underlying proximal filter 24 and the embolic debris 76 which has been captured within the proximal filter 24. During compression, the embolic debris 76 can also be elongated or may beneficially be further parted, divided and macerated into smaller pieces.

Figure 48:
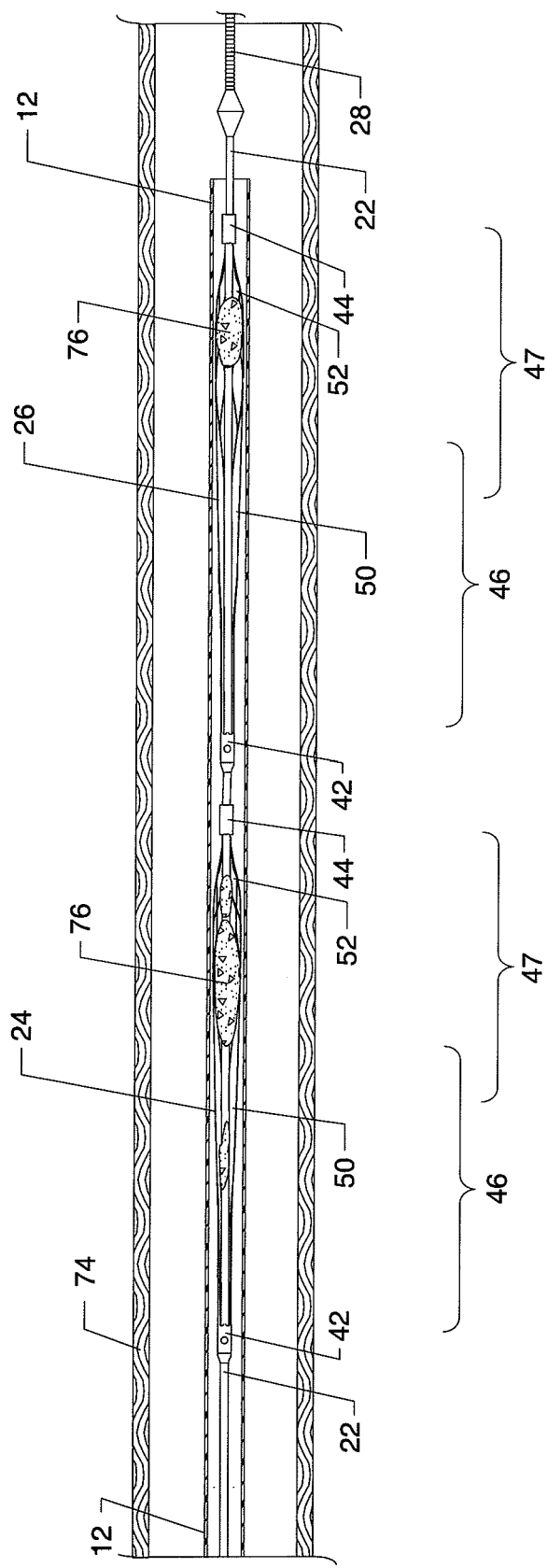
FIG. 48 is an illustration similar to FIG. 8 further showing the use of the capture/delivery sheath in the capture mode.

FIG. 48 is an illustration similar to FIG. 8 further showing the use of the capture/delivery sheath 12 in the capture mode. In this illustration, the capture/delivery sheath 12 is positioned further and fully in a distal direction where the capture/delivery sheath 12 is also in alignment directly over and about and compressingly positioned over and about the distal filter 26. Complete compression of the proximal filter 24 and the embolic debris 76 captured therein and the distal filter 26 and the embolic debris 76 captured therein provides a low profile structure of such components containing captured embolic debris 76. Components of such low profile structure containing captured embolic debris 76 may be readily withdrawn proximally through the capture/delivery sheath 12 where the guidewire 22 and the compressed embolic debris laden proximal filter 24 and distal filter 26 can be withdrawn in a proximally directed removal from the capture/delivery sheath 12 by a proximal and manual directed movement of the guidewire 22 and the attached and compressed proximal filter 24 and distal filter 26. In the alternative, the guidewire 22, the proximal filter 24, the distal filter 26 and the capture/delivery sheath 12 may be entirely and unitarily withdrawn from the blood vessel 74 by the proximal and manually directed unitary movement of the capture/delivery sheath operator 18 and the guidewire 22.

Figure 49:
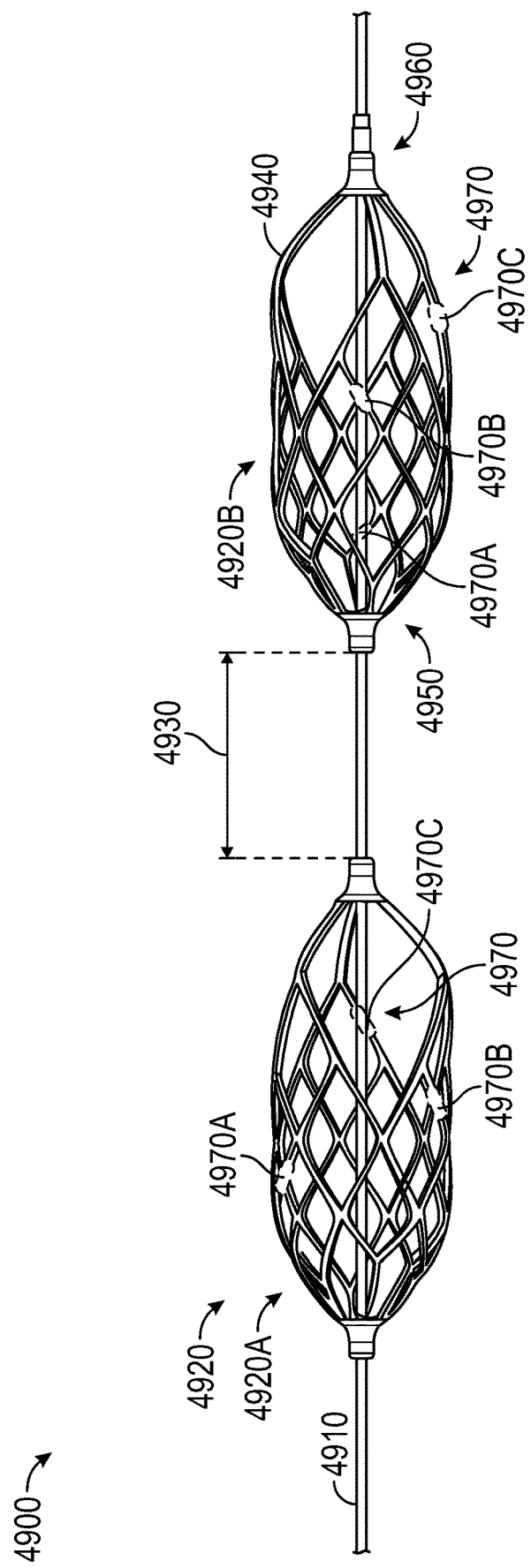
FIG. 49 illustrates a side view of an example catheter assembly.
Figure 50:
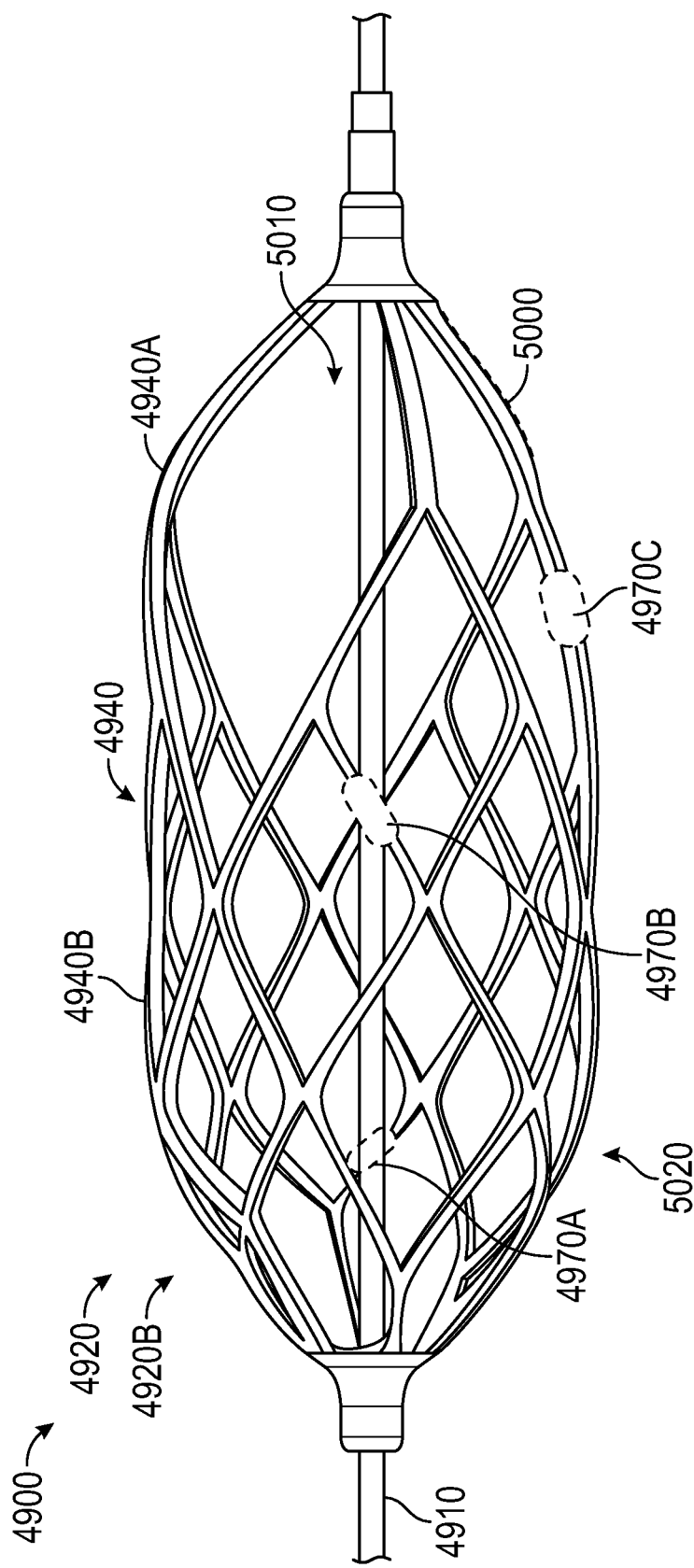
FIG. 50 illustrates a detailed side view of an example catheter assembly.

FIG. 49 and FIG. 50 illustrate a side view and a detailed side view (respectively) of an example catheter assembly 4900. In this example, the catheter assembly 4900 includes a guidewire 4910. One or more deployable filters 4920 are coupled with the guidewire 4910. As described in detail herein, in use the deployable filters 4920 engage with embolic debris (e.g., thrombus, particulate or the like) to capture and remove (e.g., macerate, dislodge, sever, separate, divide, or the like) the embolic debris from a patient.

In some examples, the deployable filters 4920 include a first deployable filter 4920A coupled with the guidewire 4910 at a first location, and a second deployable filter 4920B coupled with the guidewire 4910 at a second location. The deployable filters 4920 are, in this example, spaced by a filter gap 4930. In some examples, the deployable filters 4920 are misaligned (e.g., out of phase, staggered, offset, rotated, or the like). For instance, the first filter 4920A and its associated filaments are optionally rotated relative to the second filter 4920B and its respective filaments. As described herein, the misalignment between the filaments of the first and second filters 4920A, B enhances removal and capture of embolic debris by correspondingly increasing the engagement of debris through staggering of the filaments.

The deployable filters 4920 include one or more component strands 4940 (e.g., filaments, wires, filars, ribbons or the like). With the second deployable filter 4920B as an example, the strands 4940 extend from a proximal filter end 4950 toward a distal filter end 4960. One or more of the ends 4950, 4960 are moveably coupled along the guidewire 4910. With movement of one of the ends one or more of the component strands 4940 deflect. In one example, the filters 4920 (e.g., filters 4920A, B) transition between a compressed configuration (e.g., contracted, collapsed, squeezed, constricted, constrained, closed, compacted, stowed or the like) and a deployed configuration (e.g., expanded, open, spread, unfurled, released, distributed or the like). In the compressed configuration (e.g., as shown in FIG. 15) the filters 1920 have a first profile (e.g., one or more of cross-section, shape, size, dimensions, contour, radius, perimeter, circumference, diameter, outline, boundary, configuration, pattern, arrangement, thickness or the like). In the deployed configuration, the filters 4920 have a second larger profile.

As further shown in FIG. 49, the deployable filters 4920 include one or more imaging markers 4970 visible with imaging. For instance, the imaging markers 4970 are radiopaque, fluoroscopically visible or the like. In this example, the imaging markers 4970 are coupled with the component strands 4940. The imaging markers 4970 are readily observable through imaging techniques including, but not limited to, fluoroscopy, computer tomography, magnetic resonance imaging, ultrasound or the like. The imaging markers 4970 optionally provide contrast with the remainder of the filters 4920 to enhance the visibility of the markers. For example, a difference between a radiodensity of the imaging markers 4970 and a radiodensity of the component strands 4940 provides an observable contrast to enhance visibility of a portion of the filters 4920 and determine the relative orientation of the filters 4920. In an example, one or more of the imaging markers 4970 are observable when the filters 4920 are in the deployed configuration. Optionally, the radiodensity of the imaging markers 4970 is similar to (e.g., equal to, substantially equal to, within 10 percent, within 50 percent, or the like) a radiodensity of the guidewire 4910. Accordingly, an observable contrast between the guidewire 4910 and the imaging markers 4970 is not observable. For instance, the imaging markers 4970 are obscured (e.g., hidden, cloaked, concealed, covered, eclipsed, or the like) by the guidewire 4910 when the deployable filters 4920 are in the compressed configuration. Conversely, the imaging markers 4970, the guidewire 4910 and the position of the markers 4970 (and corresponding orientation of the filters 4920) are visible with the deployable filters in the deployed configuration.

In an example, the one or more imaging markers 4970 include a first imaging marker 4970A, a second imaging marker 4970B, and a third imaging marker 4970C. Each of the imaging markers 4970 are coupled to the strands 4940 at different locations. For example, the first imaging marker 4970A is coupled to the strands 4940 at a first location. The second imaging marker 4970B is coupled to the strands 4940 at a second location proximal to the first imaging marker 4970A and radially offset (e.g., by 120 degrees or the like). The third imaging marker 4970C is coupled to the strands 4940 at a third location proximal to the first and second imaging markers 4970A, B and radially offset (e.g. by 120 degrees or the like relative to each of the markers).

As described herein, and in some examples, the imaging markers 4970 are observable in some configurations (e.g., when the filters 4920 are deployed) and obscured in other configurations (e.g., when the filters 4920 are compressed or aligned with the guidewire). The varied longitudinal and circumferential locations of the imaging markers 4970 facilitates interpretation of a two-dimensional image of the filters 4920 with three-dimensional clarity including indications of degree of deployment of the filters 4920, longitudinal location of the filters and their rotational orientation. In contrast, other filters and therapeutic devices, when viewed through imaging techniques, have obscured configurations, orientations or both because of a common contrast across the device and overlaying of device portions when manipulated and navigated.

In an example, at least two of the imaging markers 4970 are unobscured in any orientation of the respective deployable filter 4920 (e.g., either or both of filters 4920A, B) when the filter 4920 is in a deployed configuration. For example, the imaging markers 4970B, 4970C of the filter 4920B shown in FIG. 49 are observable in the first orientation, and the imaging marker 4970A is unobservable in the first orientation. The imaging marker 4970A is optionally obscured by the guidewire 4910 when the filter 4920B is observed in the first orientation (e.g., a first location perpendicular to a length axis of the guidewire 4910). Accordingly, when observed from the first orientation, the first imaging marker 4970A of the filter 4920A is obscured, and the third imaging marker 4970C of the filter 4920B is obscured, for instance because the filter 4920A is misaligned relative to the filter 4920B.

Further, the imaging markers 4970 indicate the degree of deployment and orientation (rotationally and longitudinally) of the respective filter. For example, the imaging markers 4970A, 4970B of the filter 4920A shown in FIG. 49 are observable in a first orientation, and the imaging marker 4970C is obscured in the first orientation (e.g., because of the overlying guidewire 4910). Because each of the imaging markers 4970A-C has a discrete axial location along the filter different from the other markers visibility of two of the markers (and obscurement of the other marker) indicates the rotational orientation of the associated filter. Accordingly, with rotation to a second orientation the imaging markers 4790B, 4970C in the orientation are observed while the marker 4790A is obscured to indicate the rotational position (and optionally a degree of change in the rotational position and direction of change, such as clockwise, counter clockwise or the like).

In another example, the longitudinal position of the imaging markers 4970 is observed to indicate the degree of deployment and longitudinal position of the filters 4920 in vasculature and along the guidewire 4910. For instance, the imaging markers 4970A, B, C are positioned at discrete longitudinal locations along the filter 4920A. As the filter 4920A is deployed, in one example, with the end of the filter having the imaging marker 4970A revealed first and moving along the guidewire 4910, the imaging marker 4970A spreads away from the guidewire 4910. The second imaging marker 4970B then spreads as that portion of the filter is released, and the operator is thereby able to monitor the deployment including the degree of deployment (e.g., progression from contracted to deployed). Additionally, the observed location of the imaging markers 4970A, B, C indicates the position of the associated filter on the guidewire 4910 (e.g., relative to the guidewire itself or additional contrasting imaging markers on the guidewire).

Referring now to FIG. 50, in some examples, an adhesion layer 5000 (e.g., natural rubber, polynitrile, acrylic, isobutylene, silicone, styrene, caprolactone, PEG, or the like) is coupled to the component strands 4940 of the filters 4920. The adhesion layer 5000 promotes adhesion (e.g., stickiness, tackiness, gumminess, attraction or the like) of the component strands 4940 with respect to embolic debris. In an example, the adhesion layer 5000 enhances the engagement, capture and removal of embolic debris with the filters 4920.

Referring again to FIG. 50, in some examples, the filters 4920 include a filter mouth 5010 and a filter basket 5020. The filter mouth 5010 includes strands 4940, for instance one or more primary strands 4940A in a first 'open' density relative to the strands of the filter basket 5020. One or more secondary strands 4640B are included with the filter basket 5020 portion. In an example, a density (e.g., spacing, pitch, spread, gap, distribution, or the like) of the secondary strands 4940B is greater than a density of the primary strands 4940A. The primary strands 4940A optionally macerate embolic debris (e.g., part, divide, break up, shred or the like) and the debris enters the filter 4920 through the mouth 5010. In some examples, the (optionally larger profile and more dense) secondary strands 4940B engage with and capture the embolic debris in the basket 5020, and the debris is contained within the basket 5020 of the filters 4920, for instance to capture and remove the embolic debris from a patient.

Figure 51:
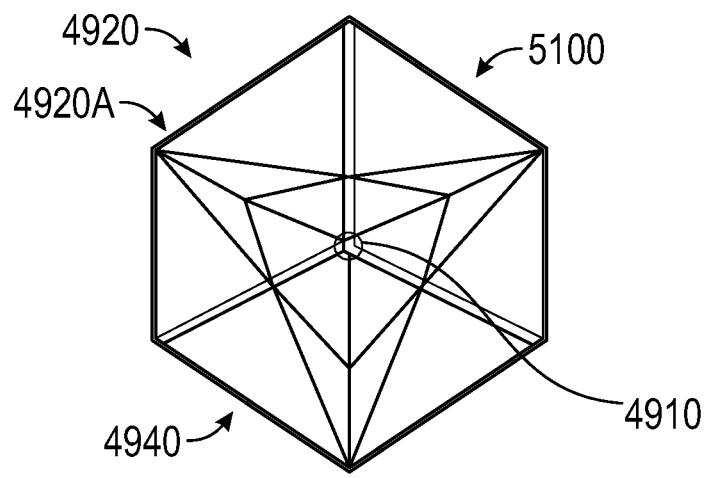
FIG. 51 illustrates a schematic view of an example of a first deployable filter.

FIG. 51 illustrates a schematic view of an example of the deployable filter 4920A. FIG. 51 shows the component strands 4940 of the deployable filter 4920A having a first filter strand profile 5100 (e.g., one or more of cross-section, shape, size, dimensions, contour, radius, perimeter, circumference, outline, boundary, configuration, pattern, arrangement, thickness or the like). The filter strand profile 5100 is shown in solid lines in FIG. 51. The component strands 4940 intersect and form a mesh of strands 4920 corresponding to the profile of the deployable filter 4920A.

Figure 52:
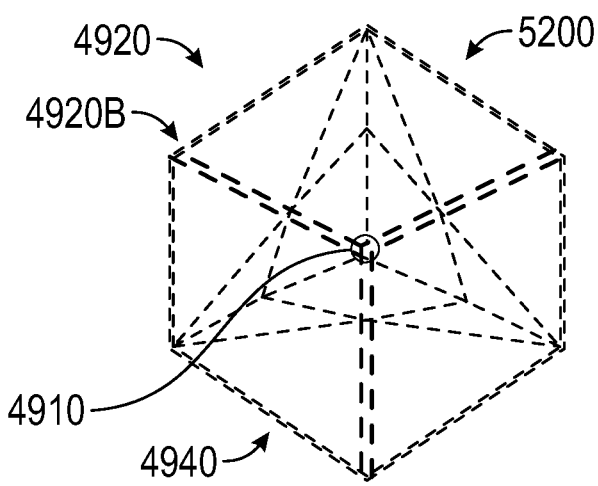
FIG. 52 illustrates a schematic view of a second deployable filter.

FIG. 52 illustrates a schematic view of the deployable filter 4920B. As shown in FIG. 49, the deployable filter 4920B is in one example the distal filter relative to the filter 4920A. FIG. 52 shows the component strands 4940 of the deployable filter 4920B having a second filter strand profile 5200 (e.g., one or more of cross-section, shape, size, dimensions, contour, radius, perimeter, circumference, outline, boundary, configuration, pattern, arrangement, thickness or the like). The filter strand profile 5200 is shown in dashed lines in FIG. 52.

Figure 53:
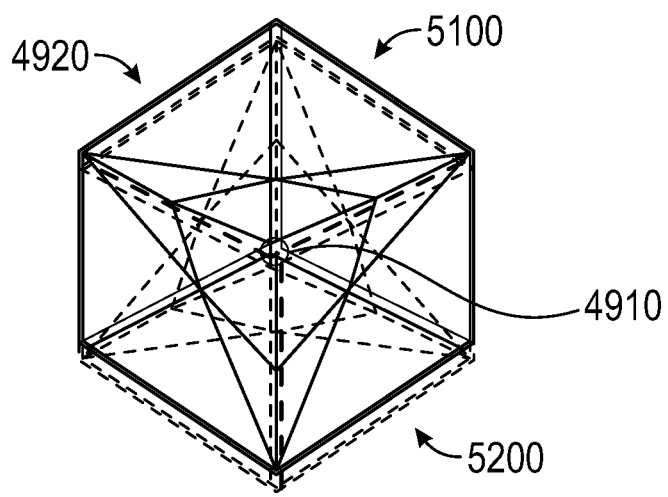
FIG. 53 illustrates a schematic view of misaligned deployable filters.

The second filter strand profile 5200 is misaligned relative to the first filter strand profile 5100 (shown in FIG. 51). As described herein, the misalignment of the filter strand profiles 5100, 5200 enhances engagement of the filters with embolic debris and enhances maceration and capture of the debris. In one example, the filter 4920A is optionally coupled with the guidewire 4910 (shown in FIG. 49) in a first configuration, such as a first angular orientation on the guidewire 4910. The second filter 4920B is coupled with the guidewire 4910 in a second configuration, such as a second, angular orientation offset from the first angular orientation. In an example, the filter 4920A is rotationally offset from the filter 4920B. For instance, the second filter strand profile 5200 is optionally 180 degrees out of alignment (e.g., misaligned) with respect to the second filter strand profile 5200 to increase the density of strands when viewed along the axis of the guide wire 4910 (as shown in FIG. 53). As described herein, the misalignment between the strands of the first and second filters 4920A, B enhances removal and capture of embolic debris by correspondingly increasing the engagement of debris through staggering of the strands.

FIG. 53 illustrates a schematic view of the misaligned deployable filters 4920A, 4920B. FIG. 53 shows the first filter strand profile 5100 in solid lines and the second filter strand profile 5200 in dashed lines. The primary strands 4940A of the filter 4920A have the filter strand profile 5100, and the primary strands 4940A of the filter 4920B have the filter strand profile 5200. As shown in FIG. 53, misaligning the filter strand profiles 5100, 5200 increases the density of filter strands in a direction corresponding to the axis of the guidewire 4910. The increased density of the filter strands enhances engagement, capture and removal of debris (e.g., the embolic debris 76 in the blood vessel 74 shown in FIG. 13). For example, the misaligned filter strand profiles 5100, 5200 increase the virtual distribution of strands 4940 as shown in FIG. 53 (relative to the strands if the filter profiles are aligned) when the filters 4920 are in a vessel. The increased distribution enhances engagement of the strands with debris in the vessel and carried by blood flow or mechanical movement of the filters toward a capture sleeve (as described herein). The increased distribution of strands 4940 facilitates capture and removal of the debris, for instance by increasing the probability that strands 4940 engage with debris. For example, the misalignment of the filters 4940 increases the coverage of the strands 4940 (e.g., the primary strands 4940A) as shown in FIG. 53 relative to the virtually less dense arrangements shown in FIGS. 51 and 52. Accordingly, the increased distribution of the strands 4940 enhances engagement with embolic debris, enhances maceration, and at the same time minimizes escape of the debris through the filters 4920. For example, particulate that is aligned with an opening in a proximal filter 4920B (and misaligned with the strands of the filter 4920B) is conversely aligned with an offset strand 4940 of the distal filter 4920A thereby increasing the likelihood of engagement, maceration and capture.

In an example, the strands 4940 macerate (e.g., break-up, disrupt, shred, dismember, or the like) embolic debris as the embolic debris moves into the filters 4920. In some examples, maceration of the embolic debris by the strands 4940 facilitates capture of the embolic debris contained in the filters 4920 as the filters 4920 are withdrawn into a catheter. For instance, the filters 4920 macerate debris into smaller, more easily compressible, particulate and facilitate collecting the debris in a capture sleeve (e.g., the capture sleeve 14 shown in FIG. 1, the capture sleeve 5300 shown in FIG. 53, or the like). In some examples, the strands 4940 engage with the captured debris with compression of the filters, and the compression drives the strands through the debris (e.g., macerates the debris). The subdivided and compressed debris is readily retained (and further compressed) by the filters and withdrawn with the filters into the capture sleeve.

The filter strand profiles 5100, 5200 optionally vary from the profiles 5100, 5200 shown in FIGS. 51, 52, and 53. For example, the strand profiles 5100, 5200 shown in FIGS. 51 and 52 are composed of a series of triangles. The strand profiles 5100, 5200 optionally include, but are not limited to squares, rectangles, polygons, amorphous shapes (including, but not limited to, curves and jagged lines), variations of the same or the like.

Figure 54:
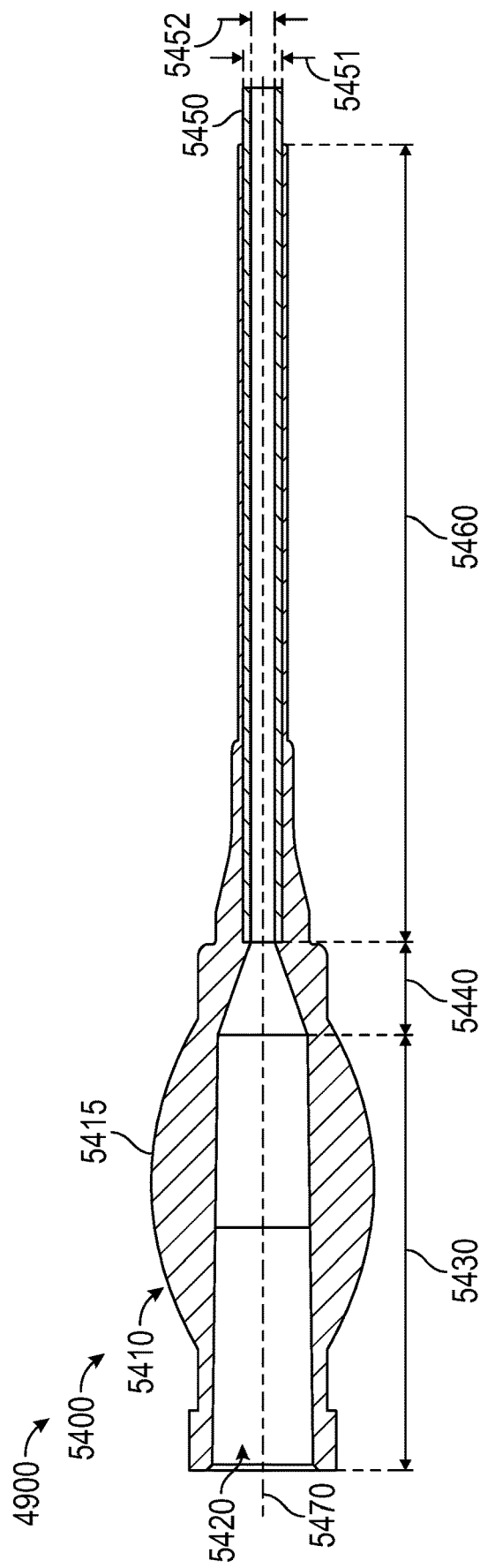
FIG. 54 illustrates an example of a filter delivery catheter.

FIG. 54 illustrates an example of a filter delivery catheter 5400. The catheter assembly 4900 includes the filter delivery catheter 5400, and the filter delivery catheter 5400 is moveably coupled with the guidewire 4910 (shown in FIG. 49). For instance, the guidewire 4910 and the filters are slideably coupled within the delivery catheter 5400. The filter delivery catheter 5400 facilitates the installation of the guidewire 4910 and the filters 4920 (shown in FIG. 49) within anatomy of a patient (e.g., the vessel 74 shown in FIG. 13). For example, the filter delivery catheter 5400 positions the filters 4920 distally relative embolic debris (e.g., in a similar manner to the configuration shown in FIG. 21), for instance downstream relative to the initial location of the debris. The filter delivery catheter 5400 is optionally removed from the patient after installation of the guidewire 4910 within the anatomy of the patient.

In an example, the filter delivery catheter 5400 includes a filter delivery operator 5410 and a hub 5415. The filter delivery operator 5410 optionally includes an interior socket 5420 surrounded by the hub 5415. In some examples, the interior socket 5420 includes a proximal section 5430 having a first dimension (e.g., diameter, or the like) and a distal section 5440 having a second dimension. The dimension of the distal section 5440 is optionally smaller than the dimension of the proximal section 5430.

A filter delivery tube 5450 extends from the filter delivery operator 5410 and provides a lumen for delivery of the filters, guidewire and the like to a specified location. The filter delivery tube 5450 is optionally received in a delivery tube section 5460 of the filter delivery operator 5410. The delivery tube section 5460 is in communication with the distal section 5440 and the proximal section 5430 of interior socket 5420. In an example, the guidewire 4910 and the associated filters are moveably coupled within the filter delivery catheter 5400. For example, the guidewire 4910 (shown in FIG. 49) is received in one or more of the proximal section 5430, the distal section 5440, the delivery tube section 5460 and the filter delivery tube 5450. While within the filter delivery catheter 5400 the filters 4920 are in the compressed configuration (e.g., within the filter delivery tube 5450).

As shown in FIG. 54, sections 5430, 5440, 5460 and the filter delivery tube 5450 are coaxial, for example along the axis 5470, to facilitate the delivery of the guidewire 4910 and the associated filters. Optionally, the filter delivery tube 5450 proximate to the filter delivery operator 5410 has an outside dimension 5451 (e.g., diameter, or the like) within a range of approximately 0.060 inches to approximately 0.080 inches. The filter delivery tube 5450 proximate to the filter delivery operator 5410 optionally has an inside dimension 5452 within a range of approximately 0.025 inches to approximately 0.050 inches. In some examples, the filter tube 5450 includes a high-density polyethylene polymeric material ("HDPE"). In one example, the filter tube 5450 does not include Polytetrafluoroethylene ("PTFE"). In such an example, the filter tube 5450 including HDPE has improved strength (e.g., tear resistance, or the like) with respect to PTFE.

Figure 55:
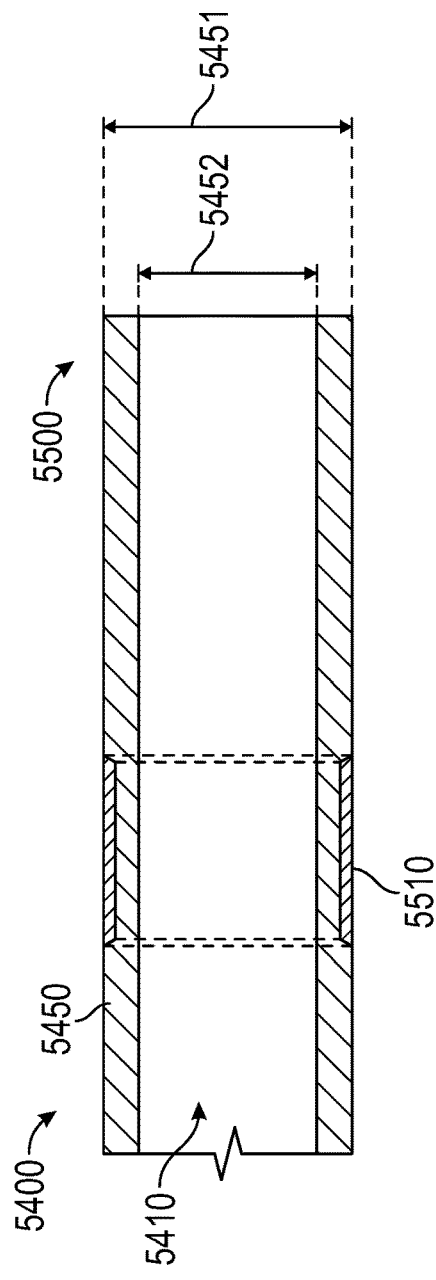
FIG. 55 illustrates an example of a filter delivery tube distal portion.

FIG. 55 illustrates an example of a filter delivery tube distal portion 5500. The filter delivery tube 5450 extends from the filter delivery operator 5410 to the filter delivery tube distal portion 5500. The filter delivery catheter 5400 facilitates delivery of the filters 4920 proximate to embolic debris. For example, the tube distal portion 5500 is located proximate to (e.g., distally from) embolic debris. The filters 4920 are deployed from the filter delivery catheter 5400. The filter delivery catheter 5400 is optionally removed from the patient (e.g. proximally), and the filters 4920 and the guidewire 4910 remain located proximate to the embolic debris.

Optionally, the filter delivery tube 5450 tapers from the filter delivery operator 5410 to the tube distal portion 5500. The tube distal portion 5500 has the outside dimension 5451, for instance within a range of approximately 0.040 inches to approximately 0.080 inches. The distal portion 5500 has the inside dimension 5452 (e.g., a lumen diameter) within a range of approximately 0.025 inches to approximately 0.050 inches or the like.

In some examples, the tube distal portion 5500 of the filter delivery tube 5450 includes a marker band 5510. The marker band 5510 is radio-opaque, and is optionally swaged onto the filter delivery tube. For instance, the marker band 5510 includes a material (e.g., metal) dissimilar to other portions of the filter delivery tube 5450 (e.g., HDPE, or the like). The marker band 5510 facilitates identification of the tube distal portion 5500 relative to other portions of the filter delivery tube 5450.

Figure 56:
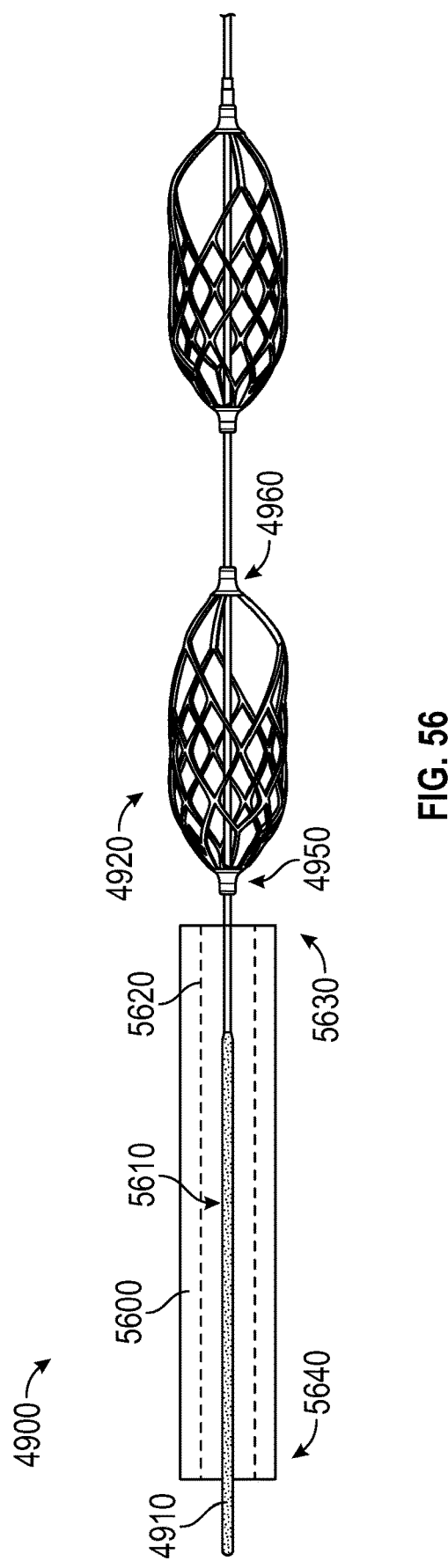
FIG. 56 illustrates an example of the catheter assembly including an installation brace

FIG. 56 illustrates an example of the catheter assembly 4900 including an installation brace 5600 that facilitates delivery of the guidewire 4910 and the compressed filters 4920 to the filter delivery catheter 5400 and the associated filter delivery tube 5450 while minimizing unintentional deployment of the filters. The installation brace 5600 includes a filter cavity 5610 surrounded by a brace wall 5620 of the installation brace 5600. The installation brace 5600 retains one or more of the deployable filters 4920 in the compressed configuration and provides an interface for delivery of the compressed filters 4920 to the filter delivery tube 5450.

For example, the installation brace 5600 facilitates compression of the filters for delivery to the filters (and the guidewire) to the filter delivery catheter 5400 and the associated filter delivery tube 5450. For instance, the guidewire 4910 is inserted into a distal end 5630 of the installation brace 5600. The guide wire 4910 is translated toward a proximal end 5640 of the installation brace 5600. The proximal end 4950 of the filters 4920 engage with the installation brace 5600, and the engagement optionally compresses the filters to transition the filters 4920 to the compressed configuration. In some examples, the proximal end 4950 of the filters 4920 is easier to compress than the distal end 4960 of the filters 4920. Accordingly, the installation brace 5600 optionally compresses the filters 4920 and retains the filters 4920 in the compressed configuration for delivery to the filter delivery catheter 5400 and the associated filter delivery tube 5450.

FIG. 57A illustrates an example of the catheter assembly 4900 with the installation brace 5600 of FIG. 56 received in the interior socket 5420. The interior socket 5420 of the filter delivery catheter 5400 receives the installation brace 5600 (with the deployable filters 4920 retained therein). The installation brace 5600 delivers the filters 4920 to the filter delivery tube 5450 in the compressed configuration and facilitates delivery of the guidewire 4910 and the compressed filters 4920 to the filter delivery catheter 5400 and the associated filter delivery tube 5450 while minimizing unintentional deployment of the filters. In some examples, the installation brace 5600 is separable from (e.g., detachable from, or the like) the interior socket 5420 of the filter delivery catheter 5400 when the guidewire 4910 and the deployable filters 4920 are installed in the filter delivery tube 5450 of the filter delivery catheter 5400. Accordingly, the installation brace 5600 provides an interface for delivery of the compressed filters 4920 to the filter delivery tube 5450.

In an example, the installation brace 5600 is received in the proximal section 5430 of the interior socket 5420. The installation brace 5600 optionally aligns the guidewire 4910 with the axis 5470 (shown in FIG. 54). The installation brace 5600 facilitates installation of the guidewire 4910 (and the filters 4920) into the filter delivery tube 5450. For instance, the installation brace 5600 delivers the filters 4920 in the compressed configuration to the distal section 5440 of the interior socket 5420 (e.g., when the guidewire 4910 is translated from the proximal end 5640 of the installation brace 5600 toward the distal end 5630 of the installation brace 5600).

Delivering the filters 4920 in the compressed state facilitates installation of the guidewire 4910 (and the filters 4920) into the filter delivery tube 5450, for instance because the filters 4920 have a similar profile (e.g., diameter, or the like) to the filter delivery tube 5450 in the compressed state. In some examples, compressing the filters 4920 from the distal end 4960 is more difficult than compressing the filters 4920 from the proximal end 4950. Accordingly, compressing the filters 4920 prior to installing the distal end 4960 of the filters into the filter delivery catheter 5400 decreases the difficulty of installing the guidewire 4910 (and the deployable filters 4920) into the filter delivery catheter 5400 with the distal end 4960 located distally of the proximal end 4950.

FIG. 57B illustrates an example of the catheter assembly 4900 with another example of the installation brace 5600 received in the interior socket 5420. In some examples, the installation brace 5600 has a tapered profile that corresponds to a tapered profile of the interior socket 5420. The tapered profiles of the socket 5420 and the installation brace 5600 facilitates insertion of the installation brace 5600 into the interior socket 5420 (e.g., by easing alignment of the brace 5600 with the socket 5420. In an example, the proximal section 5430 has a first (e.g., light, small, or the like) taper. A middle section 5700 of the interior socket 5420 has a second (e.g., medium, transition, or the like) taper. The distal section 5440 has a third (e.g., heavy, large, or the like) taper. The tapered profile of the transition tool optionally corresponds with the tapered profile of one or more of the sections 5430, 5440, 5700 to facilitate insertion of the installation brace 5600 into the interior socket 5420.

Figure 58:
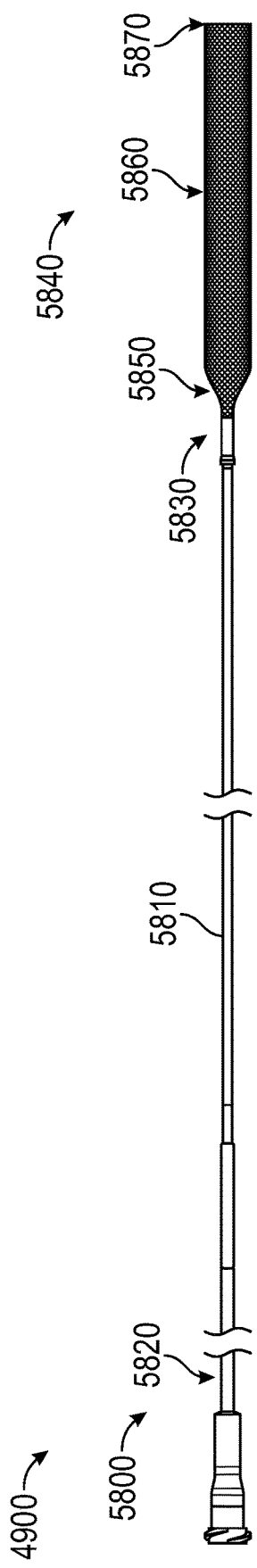
FIG. 58 illustrates an example of the catheter assembly including a capture sleeve catheter.

FIG. 58 illustrates an example of the catheter assembly 4900 including a capture sleeve catheter 5800. The capture sleeve catheter 5800 is movably coupled along the guidewire 4910 (shown in FIG. 56) and facilitates capture and removal of debris from a patient. For example, the capture sleeve catheter 5800 includes a positioning tube 5810, and the positioning tube 5810 extends from a tube proximal portion 5820 to a tube distal portion 5830. The guidewire 4910 is slidable received within one or more components of the catheter assembly 4900 such as the positioning tube 5810.

The capture sleeve catheter 5800 includes a capture sleeve 5840 coupled with the tube distal portion 5830. For instance, the capture sleeve 5840 optionally includes a tapered proximal section 5850 and a cylindrical barrel 5860 that extends distally from the tapered proximal section 5850. The capture sleeve 5840 transitions between a compressed capture sleeve configuration and a deployed capture sleeve configuration. The tapered proximal section 5850 facilitates compression of the capture sleeve 5840 and contents therein (e.g., embolic debris, the filters 4920, or the like), for instance by providing a transition between the positioning tube 5810 and the barrel 5860.

Figure 59:
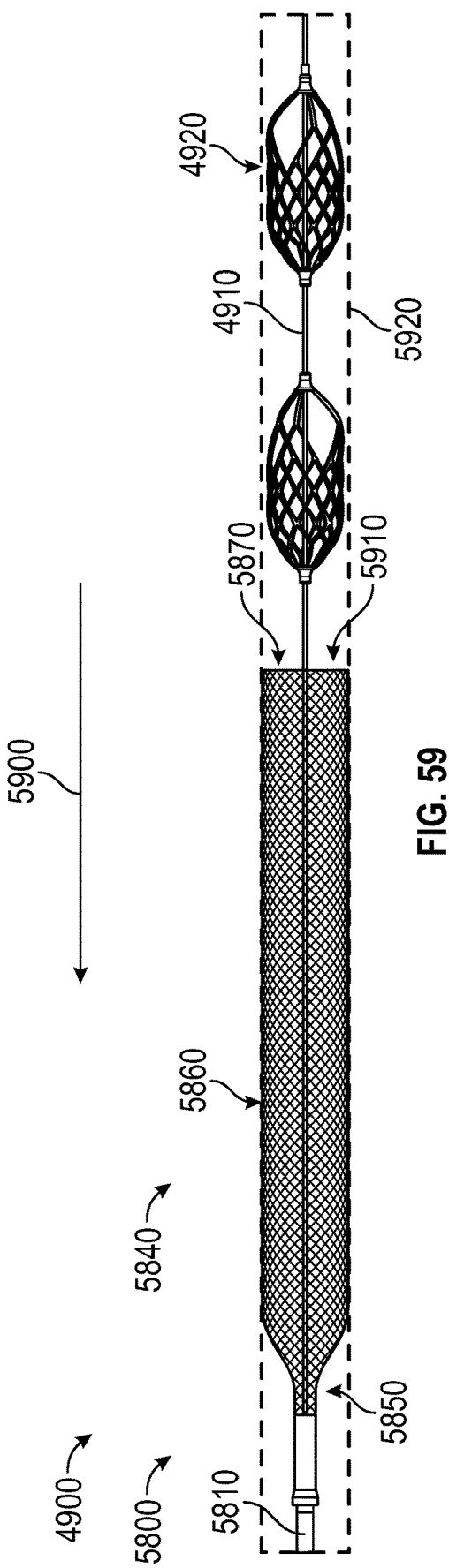
FIG. 59 illustrates an example of the catheter assembly including the guidewire, the filters, and the capture sleeve catheter.

FIG. 59 illustrates an example of the catheter assembly 4900 including the guidewire 4910, the filters 4920, and the capture sleeve catheter 5800. In some examples, the capture sleeve 5840 receives (e.g., sheathes, contains, houses, captures, accommodates entry of, or the like) one or more of the guidewire 4910, the filters 4920 and embolic debris in the filters (e.g., the embolic debris 76 shown in FIG. 13). For example, the guidewire 4910 is translated (e.g., moved, pulled, drawn, pushed, rotated, twisted, or the like) proximally in the direction indicated by arrow 5900. The proximal movement of the guidewire 4910 (or distal movement of the capture sleeve 5840) translates the guidewire 4910 (and the filters 4920) relative to the capture sleeve catheter 5800, and the capture sleeve 5840 receives the filters 4920. For instance, a mouth 5910 of the cylindrical barrel 5860 receives the filters 4920. The capture sleeve 5840 surrounds the filters 4920 and engages with the filters, for instance to compress the filters 4920 to facilitate removal of the filter 4920 (and captured debris) from the vessel. In some examples, engagement of the capture sleeve 5840 with the filters 4920 macerates embolic debris including, but not limited to, compressing the debris, squeezing out fluid while retaining solid matter or the like.

As described herein, the capture sleeve 5840 transitions between a compressed capture sleeve configuration and a deployed capture sleeve configuration. In the deployed capture sleeve configuration, the cylindrical barrel 5860 conforms to a vessel profile 5920 (e.g., the vessel 74, shown in FIG. 13) between the tapered proximal section 5850 and a capture sleeve distal tip 5870. In an example, the cylindrical barrel 5860 interfaces with a wall of a blood vessel, and the cylindrical barrel 5860 enhances the removal of embolic debris from the vessel, for instance by receiving an entirety of the one or more deployable filters 4920. Configuring the cylindrical barrel 5860 to receive the entirety of the deployable filters 4920 improves the collection of embolic debris by the catheter assembly 4900, for example by inhibiting the escape of macerated embolic debris from the capture sleeve 5840. In some examples, the cylindrical barrel 5860 has a constant outer dimension (e.g., within a range of approximately 6 millimeters to 7 millimeters) to enhance conformance of the cylindrical barrel 5860 with the vessel profile 5920. In an example, the conformance of the cylindrical barrel 5860 with the vessel profile 5920 facilitates capture of embolic debris within the cylindrical barrel 5860 by inhibiting embolic debris from passing between the cylindrical barrel 5860 and surrounding vasculature of a patient.

Figure 60:
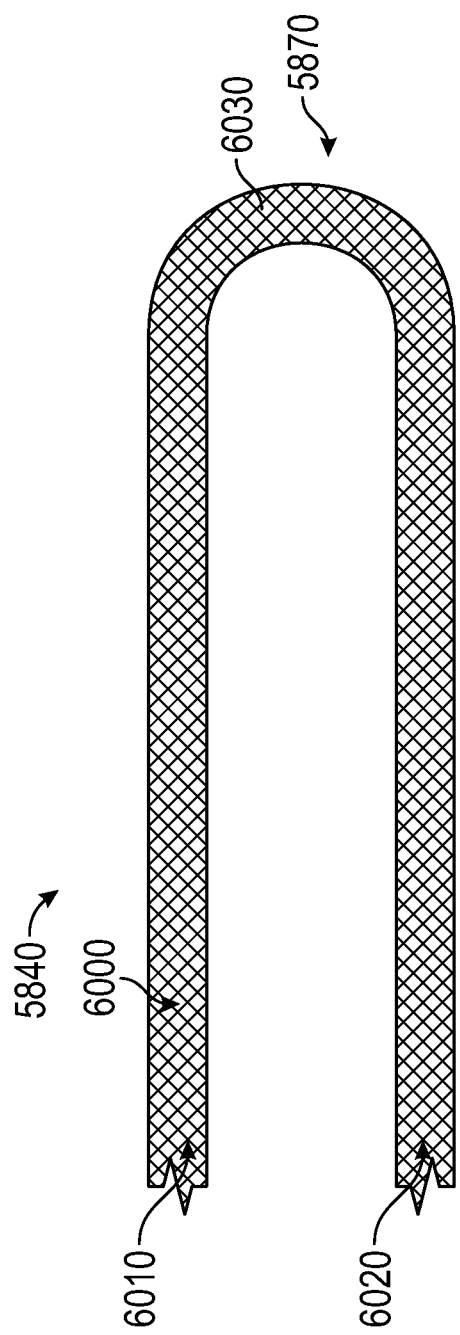
FIG. 60 illustrates an example of the capture sleeve.

FIG. 60 illustrates an example of the capture sleeve 5840. In an example, the capture sleeve 5840 includes braided filaments 6000. For instance, the filaments 6000 are braided with a herringbone pattern, chevron pattern, checker pattern, or the like. In some examples, the filaments 6000 are braided onto a sacrificial tube, mandrel or similar intermediate assembly component.

In some examples, the capture sleeve 5840 includes a first stacked layer 6010 of braided filaments 6000 and a second stacked layer 6020 of braided filaments 6000. The layer 6020 is optionally stacked (e.g., layered, lapped, folded, laminated, or the like) on the first layer 6010. Stacking the layers 6020 inhibits exposure of ends of the filaments 6000 at the capture sleeve distal tip 5870 (shown in detail in FIG. 60 and shown generally in FIG. 61) and facilitates the movement of the catheter assembly 4900 while minimizing snagging. An elbow 6030 extends between the layers 6010, 6020 proximate to the capture sleeve distal tip 5870. Optionally, the capture sleeve distal tip 5870 is bent, folded, crimped, creased, pressed, flattened, or the like to provide the elbow 6030 with the stacked layers 6010, 6020. As shown in FIG. 60, and shown at the distal tip in FIG. 61, the first stacked layer 6010 optionally folds or lays over the second stacked layer 6020.

Figure 61:
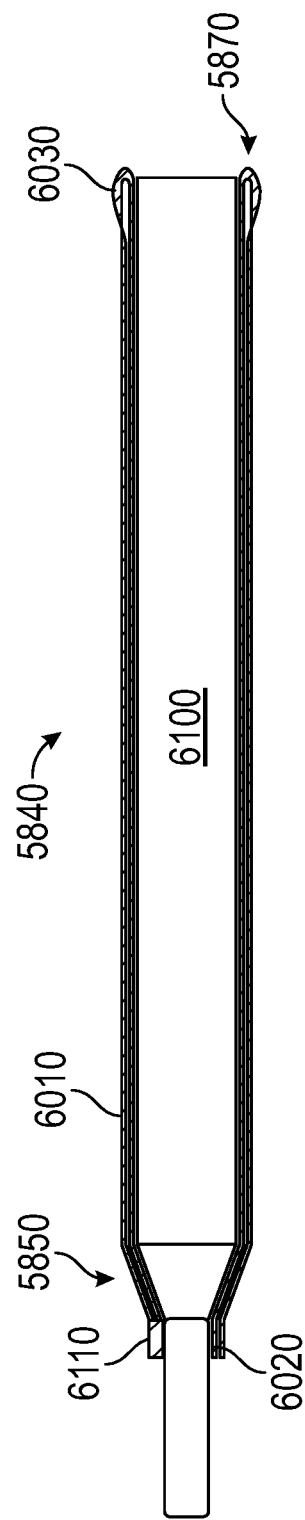
FIG. 61 illustrates the capture sleeve and the layers of braided filaments in detail.

FIG. 61 illustrates the capture sleeve 5840 and the layers 6010, 6020 of braided filaments 6000 in detail. The stacked configuration of layers 6010, 6020 minimizes (e.g., decreases or eliminates) fringes at the distal tip 5870. For instance, because the layers 6010, 6020 are formed through folding or reversal of the braids the elbow 6030 is a continuous braid and incidental fringed ends of the layers 6010, 6020 are located at the proximal portion 5850 (e.g., remote from the leading distal tip 5870). The ends of the layers 6010, 6020 are readily secured at the proximal location.

In some examples, the capture sleeve 5840 is engaged with a sacrificial tube 6100 or mandrel during a manufacturing operation (e.g., braiding, or the like) for the capturing sleeve 5840. The second stacked layer 6020 extends from the tapered proximal section 5850 to the elbow 6030 proximate to the distal tip 5870. The first stacked layer 6010 is optionally formed by continuing the braiding operation in a reversed direction from the elbow 6030 toward the tapered proximal portion 5850. In one example, a bond 6110 couples the braided filaments 6000 at the tapered proximal portion 5850 to secure the ends of the layers 6010, 6020. The bond 6110 includes one or more of a chemical bond (e.g., an adhesive, an epoxy, or the like) or a mechanical bond (e.g., a crimp, a fastener, a weld, or the like) and extends along the ends of the layers to capture the layers and minimize any incidental fringes.

FIG. 62 illustrates an example of the catheter assembly 4900, including capture sleeve 5840 and the filters 4920. As described herein, the capture sleeve 5840 receives the one or more of the deployable filters 4920 while in their deployed configurations. Reception of the deployed filters 4920 by the capture sleeve 5840 enhances capture of debris in the filters 4920 and minimizes (e.g., reduces or eliminates) escape of debris from the filters. In some examples, the capture sleeve 5840 compresses the filters 4920 when the filters 4940 are received within the capture sleeve 5840 (e.g., when the filters 4920 are fully contained within the capture sleeve 5840). Compressing the filters 4920 while the filters 4920 are received in the capture sleeve 5840 inhibits the escape of debris from the filters (e.g., escape due to the compression of the filters, for example because the strands move during expansion and compression). For example, FIG. 62 is a schematic representation of the filters 4920 in a fully deployed configuration (e.g., as shown in FIG. 59) represented by rectangles within the capture sleeve 5840 (another rectangle). The capture sleeve 5840 includes a sleeve profile 6200 (e.g., corresponding to an interior of the cylindrical barrel 5860 of the sleeve as shown in FIG. 59). Each of the one or more deployable filters 4920 (e.g., the filter 4920A shown in FIG. 49) include a filter profile 6210. In some examples, the sleeve profile 6200 corresponds with the filter profile 6210 to allow the capture sleeve 5840 to receive each of the one or more of the filters 4920 while in the fully deployed configurations. In an example, the sleeve profile 6200 corresponds (e.g., is complementary, or the like) with the filter profile 6210 to allow the capture sleeve 5840 to receive the entirety of the one or more deployed filters 4920.

After reception of the deployed filters 4920 within the capture sleeve 5840 (the schematic configuration shown in FIG. 62) the capture sleeve 5840 compresses the filters 4920 with the debris fully within the filters 4920 as well as the surrounding capture sleeve 5840 to facilitate withdrawal of the assembly from the vasculature. Compression squeezes fluid from the debris while compressing the debris (e.g., dividing, parting or crushing the debris) to a profile readily received within the capture sheath 6310. Compression of the filters 4920 by the capture sleeve 5840 further inhibits escape of embolic debris from the capture sleeve 5840 in some examples. The filaments of the filters 4920 and the filaments of the capture sleeve 5840 are drawn closer during compression while intervening spaces between the filaments are closed. Further, the filters 4920 containing debris are nested within the capture sleeve 5840 and their respective filaments overlap. Accordingly, filaments of the filters 4920 and the capture sleeve 5840 extend across openings between the filaments of the other component to provide a web that readily engages and captures the debris before, during and after compression even with dividing, party or crushing of the debris by the filaments to facilitate compression. Further, the optional stacked configuration of the layers of the capture sleeve 5840 shown in FIGS. 60 and 61 enhances engagement and capture of the debris.

FIG. 63 illustrates an example of the catheter assembly 4900 including a capture sleeve delivery catheter 6300. In an example, the capture sleeve delivery catheter 6300 includes a capture sheath 6310 extending from a sheath operator 6320 (and within the delivery catheter 6300), and in some examples the capture sheath 6310 is moveably coupled along the guidewire 4910 (shown in FIG. 49). In one example, after the capture sleeve 5840 has fully received the deployed filters 4920 and their debris, the capture sheath 6310 is advanced with the operator 6320 to move over the capture sleeve 5840 and compress the capture sleeve 5840 along with the captured filters 4920 and debris. Because of the nested components, capture of the filters in the deployed configuration (in contrast to compression prior to capture), overlapping filaments and the optional stacked braided configuration the debris is securely retained within the filters 4920 and the capture sleeve 5840 during compression to ensure liquids are released (e.g., through the filaments of the capture sleeve 5840 and filters 4920) while the solid debris remains captured within one or more of the filters 4920 or the capture sleeve 5840.

As previously discussed, the capture sheath 6310 transitions the capture sleeve 5840 and the deployable filters 4920 between deployed and compressed configurations (e.g., while the filters are received in the capture sleeve). For instance, the capture sheath 6310 is sized and shaped to receive one or more of the capture sleeve catheter 5800 (e.g., the capture sleeve 5840, the positioning tube 5810, or the like), the filters 4920, and compressed embolic debris. In an example, with the filters 4920 received in the capture sleeve catheter 5800, translation of the capture sleeve catheter 5800 with respect to the capture sheath 6310 (e.g. proximal movement of the sleeve and filters into the sheath) transitions the capture sleeve 5840 to the compressed capture sleeve configuration, and transitions the filters 4920 to the compressed configuration. The transition to the compressed capture sleeve configuration compresses embolic debris contained within the capture sleeve 5840. Accordingly, reception of the capture sleeve catheter 5800 and the filters 4920 by the capture sheath 6310 facilitates removal of embolic debris from a patient (e.g., by a doctor, surgeon, technician, nurse, healthcare provider, or the like).

FIG. 64 illustrates an example of the catheter assembly 4900. As described herein, the catheter assembly 4900, in this example, includes each of the capture sleeve catheter 5800 and the capture sleeve delivery catheter 6300 (and the filter delivery catheter 5400, shown in FIG. 54). In an example, the capture sleeve catheter 5800 includes one or more of the positioning tube 5810 and the capture sleeve 5840 (shown in FIG. 58). As described herein, the capture sleeve catheter 5800 receives the guidewire 4910 and the filters 4920. For instance, the guidewire 4910 (with the filters 4920) are inserted into a capture sheath operator 6400 of the capture sleeve catheter 5800. The capture sheath operator 6400 is, in one example, configured to selectively fix the location of one or more components of the catheter assembly 4900 (e.g., the guidewire 4910, shown in FIG. 49 coupled with filters 4920) with a clamp or the like to facilitate relative movement of the positioning tube 5810 relative to each of the guidewire 4910 (and the filters 4920).

In an example, the delivery catheter 6300 receives the capture sleeve catheter 5800 (and the guidewire 4910 and filters 4920). For instance, a delivery operator 6410 receives the capture sleeve catheter 5800 and other components of the assembly 4900. The operator 6410 is configured to selectively fix the location of one or more components of the catheter assembly 4900. For example, the operator 6410 facilitates relative movement the capture sheath 6310 relative to one or more of the capture sleeve 5840 and other components of the assembly 4900 (e.g., the guidewire 4910 and filters 4920).

Various modifications can be made to the devices set forth in the present disclosure without departing from the apparent scope thereof.

Various Notes and Aspects

Aspect 1 is a catheter assembly comprising: a guidewire extending from a guidewire proximal portion to a guidewire distal portion; first and second deployable filters coupled with the guidewire, each of the first and second deployable filters include: a proximal filter end, and a distal filter end, wherein at least one of the proximal or distal filter ends is movably coupled along the guidewire; and component strands extending between the proximal and distal filter ends; wherein the first and second deployable filters include respective first and second filter strand profiles including the respective component strands, and the first filter strand profile is misaligned relative to the second filter strand profile.

In Aspect 2, the subject matter of Aspect 1 optionally includes a capture sheath moveably coupled along the guidewire, wherein the capture sheath is configured to transition the first and second deployable filters between compressed and deployed configurations.

In Aspect 3, the subject matter of Aspect 2 optionally includes wherein the first and second strand profiles are misaligned at least in the deployed configuration.

In Aspect 4, the subject matter of any one or more of Aspects 1-3 optionally include a capture sleeve catheter movably coupled along the guidewire, the capture sleeve catheter includes: a positioning tube extending from a tube proximal portion to a tube distal portion, and the guidewire is slidably received within the positioning tube; and a capture sleeve coupled with the tube distal portion; and wherein the capture sleeve includes a tapered proximal section and a cylindrical barrel extending distally from the tapered proximal section, and in a deployed capture sleeve configuration the cylindrical barrel is configured to conform to a vessel profile between the tapered proximal section and a capture sleeve distal tip.

In Aspect 5, the subject matter of any one or more of Aspects 1-4 optionally include wherein misalignment of the first and second filter strand profiles includes the first deployable filter rotationally offset from the second deployable filter.

In Aspect 6, the subject matter of any one or more of Aspects 1-5 optionally include wherein at least one of the first or second deployable filters include at least first, second and third imaging markers, wherein: the first imaging marker is coupled at a first location along the component strands; the second imaging marker is coupled at a second location along the component strands; and the third imaging marker is coupled at a third location along the component strands, and at least two of the first, second or third imaging markers is unobscured in any orientation of the respective deployable filter in a deployed configuration.

In Aspect 7, the subject matter of Aspect 6 optionally includes wherein: the second imaging marker and the third imaging marker are observable from a first orientation; and the guidewire obscures the first imaging marker and the first imaging marker is unobservable in the first orientation.

In Aspect 8, the subject matter of Aspect 7 optionally includes wherein: the first imaging marker and the third imaging marker are observable from a second orientation; the guidewire obscures the second imaging marker and the second imaging marker is unobservable from the second orientation.

In Aspect 9, the subject matter of any one or more of Aspects 6-8 optionally include wherein at least one of the first, second, and third imaging markers are obscured in any orientation of the respective deployable filter in a compressed configuration.

Aspect 10 is a catheter assembly comprising: a guidewire extending from a guidewire proximal portion to a guidewire distal portion; one or more deployable filters coupled with the guidewire, the one or more deployable filters includes: a proximal filter end, and a distal filter end, wherein at least one of the proximal or distal filter ends is movably coupled along the guidewire; and component strands extending between the proximal and distal filter ends; and a capture sleeve catheter movably coupled along the guidewire, the capture sleeve catheter includes: a positioning tube extending from a tube proximal portion to a tube distal portion, and the guidewire is slidably received within the positioning tube; and a capture sleeve coupled with the tube distal portion; and wherein the capture sleeve includes a tapered proximal section and a cylindrical barrel extending distally from the tapered proximal section, and in a deployed capture sleeve configuration the cylindrical barrel is configured to conform to a vessel profile between the tapered proximal section and a capture sleeve distal tip.

In Aspect 11, the subject matter of Aspect 10 optionally includes wherein the capture sleeve includes braided filaments.

In Aspect 12, the subject matter of Aspect 11 optionally includes wherein the braided filaments are coupled at the tapered proximal portion with one or more of a chemical bond or a mechanical bond.

In Aspect 13, the subject matter of any one or more of Aspects 10-12 optionally include wherein the capture sleeve includes first and second stacked layers of braided filaments.

In Aspect 14, the subject matter of Aspect 13 optionally includes wherein the first stacked layer extends from the tapered proximal section to an elbow proximate the capture sleeve distal tip, and the second stacked layer extends from the elbow to the tapered proximal section.

In Aspect 15, the subject matter of any one or more of Aspects 10-14 optionally include wherein the capture sleeve is sized and shaped to receive a portion of the one or more deployable filters when the capture sleeve is deployed and the deployable filters are deployed.

In Aspect 16, the subject matter of any one or more of Aspects 10-15 optionally include wherein: the capture sleeve includes a sleeve profile; each of the one or more deployable filters include a filter profile; the sleeve profile corresponds with the filter profile to allow the capture sleeve to receive a portion of one or more of the filters.

In Aspect 17, the subject matter of Aspect 16 optionally includes wherein the sleeve profile corresponds with the filter profile to allow the capture sleeve to receive the entirety of the one or more deployable filters.

In Aspect 18, the subject matter of any one or more of Aspects 10-17 optionally include wherein the cylindrical barrel has a constant outer dimension to improve the conformance of the cylindrical barrel with the to the vessel profile.

In Aspect 19, the subject matter of any one or more of Aspects 10-18 optionally include a delivery catheter sized and shaped to receive the capture sleeve catheter.

Aspect 20 is a catheter assembly comprising: a guidewire extending from a guidewire proximal portion to a guidewire distal portion; one or more deployable filters coupled with the guidewire, each of the one or more deployable filters includes: a proximal filter end, and a distal filter end, wherein at least one of the proximal or distal filter ends is movably coupled along the guidewire; and component strands extending between the proximal and distal filter ends; a filter delivery catheter configured for movable coupling along the guidewire, the filter delivery catheter includes: a filter delivery operator including a hub having an interior socket, wherein the interior socket includes: a proximal section having a first dimension; and a distal section having a second dimension smaller than the first dimension; a filter delivery tube extending from the filter delivery operator to a filter delivery tube distal portion; and an installation brace configured for reception with the interior socket, the installation brace includes a brace wall surrounding a filter cavity, wherein the installation brace is configured to: retain the one or more deployable filters in a compressed configuration; align the one or more deployable filters with the distal section; and deliver the one or more deployable filters in the compressed configuration to the distal section of the filter delivery operator.

In Aspect 21, the subject matter of Aspect 20 optionally includes wherein the installation brace facilitates installation of the guidewire and the deployable filters into the filter delivery tube of the filter delivery catheter.

In Aspect 22, the subject matter of any one or more of Aspects 20-21 optionally include wherein the installation brace is separable from the interior socket when the guidewire and the deployable filters are installed in the filter delivery tube of the filter delivery catheter.

In Aspect 23, the subject matter of any one or more of Aspects 20-22 optionally include a capture sleeve catheter configured for movable coupling along the guidewire, the capture sleeve catheter includes: a positioning tube extending from a tube proximal portion to a tube distal portion and the guidewire is slidably received within the positioning tube; and a capture sleeve coupled with the tube distal portion; and wherein the capture sleeve includes a tapered proximal section and a cylindrical barrel extending distally from the tapered proximal section, and in a deployed capture sleeve configuration the cylindrical barrel is configured to conform to a vessel profile between the tapered proximal section and a capture sleeve distal tip.

In Aspect 24, the subject matter of any one or more of Aspects 20-23 optionally include wherein the capture sleeve is sized and shaped to receive a portion of the one or more deployable filters when the capture sleeve is deployed and the deployable filters are deployed.

In Aspect 25, the subject matter of any one or more of Aspects 20-24 optionally include wherein the first and second deployable filters include respective first and second filter strand profiles including the respective component strands, and the first filter strand profile is misaligned relative to the second filter strand profile.

Aspect 26 may include or use, or may optionally be combined with any portion or combination of any portions of any one or more of Aspects 1 through 25 to include or use, subject matter that may include means for performing any one or more of the functions of Aspects 1 through 25.

Each of these non-limiting aspects can stand on its own, or can be combined in various permutations or combinations with one or more of the other aspects.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A catheter assembly comprising:
 a guidewire extending from a guidewire proximal portion to a guidewire distal portion;
 first and second self-expanding deployable filters coupled with the guidewire, each of the first and second deployable filters include:
  a proximal filter end, and a distal filter end, wherein one of the proximal or distal filter ends is slidably coupled along the guidewire and the other of the proximal or distal filter ends is fixed to the guidewire; and component strands extending between the proximal and distal filter ends;
wherein the first and second deployable filters include respective first and second filter strand profiles including the respective component strands, and the first filter strand profile is statically misaligned relative to the second filter strand profile according to fixing of the one of the proximal or distal filter ends to the guidewire;
wherein the first and second deployable filters each have a cylindrical shape having proximal, distal and medial cylindrical portions;
wherein at least one of the first or second deployable filters include at least first, second and third imaging markers, wherein:
the first imaging marker is coupled at the proximal cylindrical portion of the cylindrical shape of the first or second deployable filters;
the second imaging marker is coupled at the medial cylindrical portion of the cylindrical shape of the first or second deployable filters; and
the third imaging marker is coupled at the distal cylindrical portion of the cylindrical shape of the first or second deployable filters, and at least two of the first, second or third imaging markers are unobscured in any orientation of the respective deployable filter in a deployed configuration; and
a capture sleeve catheter movably coupled along the guidewire, the capture sleeve catheter includes:
a positioning tube extending from a tube proximal portion to a tube distal portion, and the guidewire is slidably received within the positioning tube;
a capture sleeve coupled with the tube distal portion;
wherein the capture sleeve includes a tapered proximal section and a cylindrical barrel extending distally from the tapered proximal section, and in a deployed capture sleeve configuration the cylindrical barrel is configured to conform to a vessel profile between the tapered proximal section and a capture sleeve distal tip; and
wherein the capture sleeve includes first and second stacked layers of braided filaments, and the first stacked layer extends from the tapered proximal section to an elbow proximate the capture sleeve distal tip, and the second stacked layer extends from the elbow toward the tapered proximal section.

2. The catheter assembly of claim 1, further comprising a delivery sheath configured to transition the first and second deployable filters between compressed and deployed configurations, and wherein in the deployed configuration the delivery sheath is withdrawn and the first and second deployable filters self-expand.

3. The catheter assembly of claim 2, wherein the first and second strand profiles are misaligned at least in the deployed configuration.

4. The catheter assembly of claim 1, wherein misalignment of the first and second filter strand profiles includes the first deployable filter rotationally offset from the second deployable filter and statically fixing the one of the proximal or distal filter ends to the guidewire is configured to maintain the rotational offset between the first deployable filter and the second deployable filter.

5. The catheter assembly of claim 1, wherein:
the second imaging marker and the third imaging marker are observable from a first orientation; and
the guidewire obscures the first imaging marker and the first imaging marker is unobservable in the first orientation.

6. The catheter assembly of claim 5, wherein:
the first imaging marker and the third imaging marker are observable from a second orientation;
the guidewire obscures the second imaging marker and the second imaging marker is unobservable from the second orientation.

7. The catheter assembly of claim 1, wherein at least one of the first, second, and third imaging markers are obscured in any orientation of the respective deployable filter in a compressed configuration.

8. A catheter assembly comprising:
a guidewire extending from a guidewire proximal portion to a guidewire distal portion;
one or more deployable filters coupled with the guidewire, the one or more deployable filters includes:
a proximal filter end, and a distal filter end, wherein at least one of the proximal or distal filter ends is movably coupled along the guidewire; and
component strands extending between the proximal and distal filter ends; and
a capture sleeve catheter movably coupled along the guidewire, the capture sleeve catheter includes:
a positioning tube extending from a tube proximal portion to a tube distal portion, and the guidewire is slidably received within the positioning tube;
a capture sleeve coupled with the tube distal portion;
wherein the capture sleeve includes a tapered proximal section and a cylindrical barrel extending distally from the tapered proximal section, and in a deployed capture sleeve configuration the cylindrical barrel is configured to conform to a vessel profile between the tapered proximal section and a capture sleeve distal tip; and
wherein the capture sleeve includes first and second stacked layers of braided filaments, and the first stacked layer extends from the tapered proximal section to an elbow proximate the capture sleeve distal tip, and the second stacked layer extends from the elbow toward the tapered proximal section.

9. The catheter assembly of claim 8, wherein the capture sleeve includes braided filaments.

10. The catheter assembly of claim 9, wherein the braided filaments are coupled at the tapered proximal portion with one or more of a chemical bond or a mechanical bond.

11. The catheter assembly of claim 8, wherein the capture sleeve is sized and shaped to receive a portion of the one or more deployable filters when the capture sleeve is deployed and the one or more deployable filters are deployed.

12. The catheter assembly of claim 8, wherein:
the capture sleeve includes a sleeve profile;
each of the one or more deployable filters include a filter profile;
the sleeve profile corresponds with the filter profile to allow the capture sleeve to receive a portion of one or more of the one or more deployable filters.

13. The catheter assembly of claim 12, wherein the sleeve profile corresponds with the filter profile to allow the capture sleeve to receive the entirety of the one or more deployable filters.

14. The catheter assembly of claim 8, wherein the cylindrical barrel has a constant outer dimension to improve the conformance of the cylindrical barrel with the to the vessel profile.

15. The catheter assembly of claim 8, further comprising a delivery catheter sized and shaped to receive the capture sleeve catheter.

16. A catheter assembly comprising:
- a guidewire extending from a guidewire proximal portion to a guidewire distal portion;
- one or more self-expanding deployable filters coupled with the guidewire, each of the one or more deployable filters includes:
  - a proximal filter end, and a distal filter end, wherein one of the proximal or distal filter ends is slidably coupled along the guidewire and the other of the proximal or distal filter ends is fixed to the guidewire;
  - component strands extending between the proximal and distal filter ends; and
  - wherein the first and second deployable filters include respective first and second filter strand profiles including the respective component strands, and the first filter strand profile is statically misaligned relative to the second filter strand profile according to fixing of the one of the proximal or distal filter ends to the guidewire;
- wherein the first and second deployable filters each have a cylindrical shape having proximal, distal, and medial cylindrical portions;
- wherein at least one of the first or second deployable filters include at least first, second and third imaging markers, wherein:
  - the first imaging marker is coupled at the proximal cylindrical portion of the first or second deployable filters;
  - the second imaging marker is coupled at the medial cylindrical portion of the first or second deployable filters; and
  - the third imaging marker is coupled at a distal location along the cylindrical profile of the first or second deployable filters, and at least two of the first, second or third imaging markers are unobscured in any orientation of the respective deployable filter in a deployed configuration;
- a filter delivery catheter configured for movable coupling along the guidewire, the filter delivery catheter includes:
  - a filter delivery operator including a hub having an interior socket, wherein the interior socket includes:
    - a proximal section having a first dimension; and
    - a distal section having a second dimension smaller than the first dimension; and
  - a filter delivery tube extending from the filter delivery operator to a filter delivery tube distal portion;
  - an installation brace configured for reception with the interior socket, the installation brace includes a brace wall surrounding a filter cavity, wherein the installation brace is configured to:
    - retain the one or more deployable filters in a compressed configuration;
    - align the one or more deployable filters with the distal section; and
    - deliver the one or more deployable filters in the compressed configuration to the distal section of the filter delivery operator; and
- a capture sleeve catheter movably coupled along the guidewire, the capture sleeve catheter includes:
  - a positioning tube extending from a tube proximal portion to a tube distal portion, and the guidewire is slidably received within the positioning tube;
  - a capture sleeve coupled with the tube distal portion;
  - wherein the capture sleeve includes a tapered proximal section and a cylindrical barrel extending distally from the tapered proximal section, and in a deployed capture sleeve configuration the cylindrical barrel is configured to conform to a vessel profile between the tapered proximal section and a capture sleeve distal tip; and
  - wherein the capture sleeve includes first and second stacked layers of braided filaments, and the first stacked layer extends from the tapered proximal section to an elbow proximate the capture sleeve distal tip, and the second stacked layer extends from the elbow toward the tapered proximal section.

17. The catheter assembly of claim 16, wherein the installation brace facilitates installation of the guidewire and the one or more deployable filters into the filter delivery tube of the filter delivery catheter.

18. The catheter assembly of claim 16, wherein the installation brace is separable from the interior socket when the guidewire and the one or more deployable filters are installed in the filter delivery tube of the filter delivery catheter.

19. The catheter assembly of claim 16, wherein the one or more deployable filters include first and second deployable filters, and the first and second deployable filters include respective first and second filter strand profiles including the respective component strands, and the first filter strand profile is misaligned relative to the second filter strand profile.

* * * * *